(12) United States Patent
Lin et al.

(10) Patent No.: US 9,180,107 B2
(45) Date of Patent: Nov. 10, 2015

(54) COMBINATION TREATMENT OF CANCER WITH CETUXIMAB AND TETRAC

(75) Inventors: Hung-Yun Lin, Schenectady, NY (US); Faith B. Davis, West Sand Lake, NY (US); Paul J. Davis, West Sand Lake, NY (US); Shaker A. Mousa, Wynantskill, NY (US)

(73) Assignee: NANOPHARMACEUTICALS LLC, Rensselaer, NY (US)

( * ) Notice: Subject to any disclaimer, the term of this patent is extended or adjusted under 35 U.S.C. 154(b) by 308 days.

(21) Appl. No.: 12/751,375

(22) Filed: Mar. 31, 2010

(65) Prior Publication Data

US 2010/0255108 A1    Oct. 7, 2010

Related U.S. Application Data

(60) Provisional application No. 61/165,119, filed on Mar. 31, 2009.

(51) Int. Cl.
| | |
|---|---|
| *A01N 59/22* | (2006.01) |
| *A61K 9/14* | (2006.01) |
| *A61K 9/16* | (2006.01) |
| *A61K 9/50* | (2006.01) |
| *A61K 39/00* | (2006.01) |
| *A61K 39/395* | (2006.01) |
| *C07K 16/00* | (2006.01) |
| *C12P 21/08* | (2006.01) |
| *A61K 31/192* | (2006.01) |
| *A61K 45/06* | (2006.01) |
| *A61K 47/48* | (2006.01) |

(52) U.S. Cl.
CPC ............ *A61K 31/192* (2013.01); *A61K 39/3955* (2013.01); *A61K 45/06* (2013.01); *A61K 47/48853* (2013.01); *A61K 47/48907* (2013.01); *A61K 47/48915* (2013.01)

(58) Field of Classification Search
None
See application file for complete search history.

(56) References Cited

U.S. PATENT DOCUMENTS

| | | |
|---|---|---|
| 3,625,214 A | 12/1971 | Higuchi |
| 4,205,058 A | 5/1980 | Wagner et al. |
| 4,650,751 A | 3/1987 | Siegel et al. |
| 4,789,734 A | 12/1988 | Pierschbacher |
| 4,801,504 A | 1/1989 | Burdick et al. |
| 4,801,575 A | 1/1989 | Pardridge |
| 4,906,474 A | 3/1990 | Langer et al. |
| 4,925,673 A | 5/1990 | Steiner et al. |
| 4,968,590 A | 11/1990 | Kuberasampath et al. |
| 5,011,486 A | 4/1991 | Aebischer et al. |
| 5,091,513 A | 2/1992 | Huston et al. |
| 5,104,895 A | 4/1992 | Spinelli et al. |
| 5,225,204 A | 7/1993 | Chen et al. |
| 5,231,000 A | 7/1993 | Majocha et al. |
| 5,304,121 A | 4/1994 | Sahatjian |
| 5,410,016 A | 4/1995 | Hubbell et al. |
| 5,438,126 A | 8/1995 | DeGroot et al. |
| 5,482,719 A | 1/1996 | Guillet et al. |
| 5,571,840 A | 11/1996 | Mayor |
| 5,591,709 A | 1/1997 | Lindenbaum |
| 5,593,688 A | 1/1997 | Baldeschwieler |
| 5,648,506 A | 7/1997 | Desai et al. |
| 5,766,635 A | 6/1998 | Spenleuhauer et al. |
| 6,139,870 A | 10/2000 | Verrecchia |
| 6,316,412 B1 | 11/2001 | Ginsberg et al. |
| 6,414,037 B1 | 7/2002 | Pezzuto et al. |
| 6,482,406 B1 | 11/2002 | Stewart |
| 6,677,473 B1 | 1/2004 | Madison et al. |
| 6,740,680 B1 * | 5/2004 | Danforth, Jr. et al. ........ 514/570 |
| 6,818,620 B2 | 11/2004 | Bhatnagar |
| 6,821,947 B2 | 11/2004 | Iozzo |
| 7,166,155 B2 | 1/2007 | Ishikawa |
| 7,638,558 B2 * | 12/2009 | Breitenkamp et al. ..... 514/772.1 |
| 7,785,632 B2 | 8/2010 | Mousa et al. |
| 7,807,621 B2 | 10/2010 | Mazar et al. |
| 8,026,209 B2 * | 9/2011 | Gaillard et al. ................ 514/1.2 |
| 8,071,134 B2 | 12/2011 | Mousa et al. |
| 8,242,171 B2 | 8/2012 | Sinclair et al. |
| 8,518,451 B2 | 8/2013 | Mousa et al. |
| 8,668,926 B1 | 3/2014 | Davis et al. |
| 8,802,240 B2 | 8/2014 | Davis et al. |
| 2001/0021763 A1 | 9/2001 | Harris |
| 2001/0046521 A1 | 11/2001 | Zasloff et al. |
| 2002/0049247 A1 | 4/2002 | Chen |
| 2002/0137676 A1 | 9/2002 | Hsiang et al. |
| 2002/0151594 A1 | 10/2002 | Morkin et al. |
| 2003/0027940 A1 | 2/2003 | Lang et al. |
| 2003/0138557 A1 | 7/2003 | Allison |
| 2003/0157098 A1 | 8/2003 | Laug |
| 2003/0162758 A1 | 8/2003 | Schwartz et al. |
| 2003/0165576 A1 | 9/2003 | Fujii et al. |
| 2004/0013728 A1 | 1/2004 | Oh et al. |

(Continued)

FOREIGN PATENT DOCUMENTS

| | | |
|---|---|---|
| CA | 2673133 A1 | 11/2008 |
| CN | 1126589 | 7/1996 |

(Continued)

OTHER PUBLICATIONS

ADAM Medical encyclopedia, 2012, www.ncbi.nlm.nih.gov/pubmedhealth/PMH0001308/, downloaded Jul. 11, 2012.*

(Continued)

*Primary Examiner* — Shulamith H Shafer
(74) *Attorney, Agent, or Firm* — Schmeiser, Olsen & Watts, LLP

(57) ABSTRACT

Provided herein are compositions and methods for treating cancer by increasing the inhibitory effect of cetuximab on HIF1α expression by administering cetuximab in combination with anti-angiogenic thyroid hormone analogs such as tetrac or triac.

21 Claims, 27 Drawing Sheets

(56) References Cited

U.S. PATENT DOCUMENTS

| | | | |
|---|---|---|---|
| 2004/0033259 | A1 | 2/2004 | Hanshew, Jr. et al. |
| 2005/0124862 | A1* | 6/2005 | Mousa et al. ............... 600/300 |
| 2005/0158376 | A1 | 7/2005 | Sardi et al. |
| 2005/0171027 | A1 | 8/2005 | Sinclair et al. |
| 2005/0222387 | A1 | 10/2005 | Debatin et al. |
| 2005/0249721 | A1 | 11/2005 | Houston et al. |
| 2005/0272817 | A1 | 12/2005 | Heino |
| 2006/0166303 | A1 | 7/2006 | Spanuth |
| 2006/0210539 | A1 | 9/2006 | Zhang |
| 2007/0117841 | A1 | 5/2007 | Ozes et al. |
| 2007/0190160 | A1 | 8/2007 | Turos et al. |
| 2008/0124280 | A1 | 5/2008 | Mousa et al. |
| 2008/0193377 | A1 | 8/2008 | Line et al. |
| 2009/0022806 | A1 | 1/2009 | Mousa et al. |
| 2009/0175862 | A1* | 7/2009 | Silverio et al. ............. 424/133.1 |
| 2010/0112079 | A1 | 5/2010 | Mousa et al. |
| 2010/0159021 | A1 | 6/2010 | Davis et al. |
| 2010/0209382 | A1 | 8/2010 | Alexander-Bridges et al. |
| 2011/0052715 | A1 | 3/2011 | Davis et al. |
| 2011/0142941 | A1 | 6/2011 | Davis et al. |
| 2012/0258069 | A1 | 10/2012 | Alexander-Bridges et al. |
| 2012/0315320 | A1 | 12/2012 | Davis et al. |
| 2014/0072635 | A1 | 3/2014 | Mousa et al. |
| 2014/0072646 | A1 | 3/2014 | Mousa et al. |
| 2014/0199375 | A1 | 7/2014 | Mousa et al. |

FOREIGN PATENT DOCUMENTS

| | | | |
|---|---|---|---|
| KR | 100830889 B1 * | 5/2008 | |
| WO | 9500135 | 1/1995 | |
| WO | 9640048 | 12/1996 | |
| WO | 9833942 | 8/1998 | |
| WO | 9856771 | 12/1998 | |
| WO | 9958119 A1 | 11/1999 | |
| WO | 9962549 | 12/1999 | |
| WO | 0064431 A1 | 11/2000 | |
| WO | 0078815 A1 | 12/2000 | |
| WO | 0113031 A2 | 2/2001 | |
| WO | 0113936 A1 | 3/2001 | |
| WO | 0176589 A1 | 10/2001 | |
| WO | 0203914 A2 | 1/2002 | |
| WO | 0249501 A2 | 6/2002 | |
| WO | 02060389 A2 | 8/2002 | |
| WO | 03075741 A2 | 9/2003 | |
| WO | 2004013728 A2 | 2/2004 | |
| WO | 2004069201 A2 | 8/2004 | |
| WO | 2005027895 A2 | 3/2005 | |
| WO | 2006003014 A2 | 1/2006 | |
| WO | 2006031922 A2 | 3/2006 | |
| WO | 2007035612 A2 | 3/2007 | |
| WO | 2008051291 A2 | 5/2008 | |
| WO | WO-2008140507 A2 | 11/2008 | |
| WO | 2010120506 A1 | 10/2010 | |
| WO | 2010148007 A2 | 12/2010 | |

OTHER PUBLICATIONS

Lameloise et al. 2001. European J of Endoc. 144:145-154.*
Panyam et al. Advanced Drug Delivery Reviews 2003. 55:329-347.*
Ma et al. 1998. J. Pharm Sci. 87:1375-1378.*
NCI Cancer Drug Information, Cetuximab, 2006, http://www.cancer.gov/cancertopics/druginfo/cetuximab, downloaded Jul. 18, 2014.*
Yalcin et al. 2010. J. Clin Endoc Metab. 95:1972-1980.*
Yalcin et al. 2009. Anticancer Res. 29:3825-3832.*
Gu et al. 2007. Nanotoday 2:14-21).*
Davis et al. (2006), "Cell-slime receptor for thyroid hormone and tumor cell proliferation", Expert Reviews in Endicrinology and Metabolism, 1(6):753-761.
Luidens et al. (2010), "Thyroid hormone and angiogenesis", Vascular Pharmacology, 52(3-4):142-145.
Moeller et al. (2006), "Thyroid hormone mediated changes in gene expression can be initiated by cytosolic action of the thyroid hormone receptor beta through the phosphatidylinositol 3-kinase pathway", Nuclear Receptor Signaling, 4: E020.
Shaker et al. (2006), "Proangiogenesis Action of the Thyroid Hormone Analog 3,5-Diiodothyropropionic Acid (DITPA) Is Initiated at the Cell Surface and Is Integrin Mediated", Endocrinology, 147(4):1602-1607.
Davis, et al., "Cell-surface receptor for thyroid hormone and tumor cell proliferation", Expert Reviews in Endocrinology and Metabolism 1(6):753-761 (2006).
Balin-Gauthier et al., "In vivo and in vitro antitumor activity of oxaliplatin in combination with cetuximab in human colorectal tumor cell lines expressing different level of EGFR", Cancer Chemother. Pharmacol., 57:709-718 (2006).
Baur et al., "Resveratrol improves health and survival of mice on a high-calorie diet", Nature, 444:337-342 (2006).
Baur et al., "Therapeutic potential of resveratrol: the in vivo evidence", Nat. Rev. Drug Discov., 5:493-506 (2006).
Bergh et al., "Integrin $\alpha_v\beta3$ Contains a Cell Surface Receptor Site for Thyroid Hormone that Is Linked to Activation of Mitogen-Activated Protein Kinase and Induction of Angiogenesis", Endocrinol., 146(7):2864-2871 (2005).
Beum et al., "Binding of Rituximab, Trastuzumab, Cetuximab, or mAb T101 to Cancer Cells Promotes Trogocytosis Mediated by THP-1 Cells and Monocytes", J. Immunol., 181:8120-8132 (2008).
Bilello et al., "Effect of 2',3'-Didehydro-3'-Deoxythymidine in an in Vitro Hollow-Fiber Pharmacodynamic Model System Correlates with Results of Dose-Ranging Clinical Studies", Antimicrob Agents Chemother., 38(6):1386-1391 (1994).
Bokemeyer et al., "Fluorouracil, Leucovorin, and Oxaliplatin With and Without Cetuximab in the First-Line Treatment of Metastatic Colorectal Cancer", J. Clin. Oncol., 27(5):663-671 (2009).
Brachmann et al., "The SIR2 gene family, conserved from bacteria to humans, functions in silencing, cell cycle progression, and chromosome stability", Genes Dev., 9:2888-2902 (1995).
Brockhoff et al., "Differential impact of Cetuximab, Pertuzumab and Trastuzumab on BT474 and SK-BR-3 breast cancer cell proliferation", Cell Prolif., 40:488-507 (2007).
Bulitta et al., "Development and Qualification of a Pharmacodynamic Model for the Pronounced Inoculum Effect of Ceftazidime against Pseudomonas aeruginosa", Antimicrob. Agents Chemother., 53(1):46-56 (2009).
D'Arezzo et al., "Rapid Nongenomic Effects of 3,5,3'-Triiodo-L-Thyronine on the Intracellular pH of L-6 Myoblasts are Mediated by Intracellular Calcium Mobilization and Kinase Pathways", Endocrinol., 145(12):5694-5703 (2004).
Davis et al., "Acting via a Cell Surface Receptor, Thyroid Hormone is a Growth Factor for Glioma Cells", Cancer Res., 66(14):7270-7275 (2006).
Davis et al., "Mechanisms of nongenomic actions of thyroid hormone", Front. Neuroendocrinol., 29:211-218 (2008).
Davis et al., "Proangiogenic Action of Thyroid Hormone Is Fibroblast Growth Factor-Dependent and Is Initiated at the Cell Surface", Circ. Res., 94:1500-1506 (2004).
Davis et al., "Translational implications of nongenomic actions of thyroid hormone initiated at its integrin receptor", Am. J. Physiol. Endocrinol. Metab., 297:E1238-E1246 (2009).
Drusano et al.,"Pharmacodynamics of Abacavir in an In Vitro Hollow-Fiber Model System", Antimicrob. Agents Chemother., 46(2):464-470 (2002).
Frye, R. A., "Characterization of Five Human cDNAs with Homology to the Yeast SIR2 Gene: Sir2-like Proteins (Sirtuins) Metabolize NAD and May Have Protein ADP-Ribosyltransferase Activity", Biochem. Biophys. Res. Comm., 260:273-279 (1999).
GenBank Accession No. AF083106, dated Apr. 14, 2000.
GenBank Accession No. AF083107, dated Mar. 21, 2001.
GenBank Accession No. NM_012238, dated Apr. 25, 2010.
GenBank Accession No. NM_030593, dated Mar. 14, 2010.
GenBank Accession No. NP_036370, dated Apr. 25, 2010.
GenBank Accession No. NP_501912, dated Nov. 13, 2008.
GenBank Accession No. P53685, dated Apr. 20, 2010.
Jain et al., "Strategies and technologies for drug delivery systems", TIPS, 19:155-157 (1998).
Jonker et al., "Cetuximab for the Treatment of Colorectal Cancer", N. Engl. J. Med., 357(20):2040-2048 (2007).

(56) References Cited

OTHER PUBLICATIONS

Kalofonos et al., "Monoclonal Antibodies in the Management of Solid Tumors", *Curr. Top. Med. Chem.*, 6:1687-1705 (2006).
Koutras et al., "Antiproliferative effect of exemestane in lung cancer cells", *Mol. Cancer*, 8(1):109 (2009) (12 pages).
Lameloise et al., "Differences between the effects of thyroxine and tetraiodothyroacetic acid on TSH suppression and cardiac hypertrophy", *Eur. J. Endocrinol.*, 144:145-154 (2001).
Li et a., "Requirement of hypoxia-inducible factor-1α down-regulation in mediating the antitumor activity of the anti-epidermal growth factor receptor monoclonal antibody cetuximab", *Mol. Cancer Ther.*, 7(5):1207-1217 (2008).
Lin et al., "Integrin αvβ3 contains a receptor site for resveratrol", *FASEB J.*, 20:E1133-E1138 (2006).
Lin et al., "L-Thyroxine vs. 3,5,3'-triiodo-L-thyronine and cell proliferation: activation of mitogen-activated protein kinase and phosphatidylinositol 3-kinase", *Am. J. Physiol. Cell Physiol.*, 296:C980-C991 (2009).
Lin et al., "Resveratrol Causes COX-2- and p53-Dependent Apoptosis in Head and Neck Squamous Cell Cancer Cells", *J. Cell. Biochem.*, 104:2131-2142 (2008).
Lin et al., "Resveratrol Induced Serine Phosphorylation of p53 Causes Apoptosis in a Mutant p53 Prostate Cancer Cell Line", *J. Urol.*, 168:748-755 (2002).
Lin et al., "Resveratrol is pro-apoptotic and thyroid hormone is anti-apoptotic in glioma cells: both actions are integrin and ERK mediated", *Carcinogenesis*, 29(1):62-69 (2008).
Lin et al., "Thyroid hormone is a MAPK-dependent growth factor for thyroid cancer cells and is anti-apoptotic", *Steroids*, 72:180-187 (2007).
Louie et al., "Pharmacodynamics of Levofloxacin in a Murine Pneumonia Model of *Pseudomonas aeruginosa* Infection: Determination of Epithelial Lining Fluid Targets", Antimicrob Agents Chemother., 53(8):3325-3330 (2009).
Martens et al., "Inhibition of Glioblastoma Growth in a Highly Invasive Nude Mouse Model Can Be Achieved by Targeting Epidermal Growth Factor Receptor but not Vascular Endothelial Growth Factor Receptor-2", *Clin. Cancer Res.*, 14(17):5447-5458 (2008).
Moreno et al., "Metabolic Effects of Thyroid Hormone Derivatives", *Thyroid*, 18(2):239-253 (2008).
Mousa et al., "Tetraiodothyroacetic acid, a small molecule integrin ligand, blocks angiogenesis induced by vascular endothelial growth factor and basic fibroblast growth factor", *Angiogenesis*, 11:183-190 (2008).
Oak et al., "Antiangiogenic properties of natural polyphenols from red wine and green tea", *J. Nutr. Biochem.*, 16:1-8 (2005).
Patel, D. K., "Clinical Use of Anti-Epidermal Growth Factor Receptor Monoclonal Antibodies in Metastatic Colorectal Cancer", *Pharmacotherapy*, 28(11 Pt.2):31S-41S (2008).
Plow et al., "Ligand Binding to Integrins", *J. Biol. Chem.*, 275(29):21785-21788 (2000).
Rebbaa et al., "Novel function of the thyroid hormone analog tetraiodothyroacetic acid: a cancer chemosensitizing and anti-cancer agent", *Angiogenesis*, 11:269-276 (2008).
Shih et al., "Inhibitory effect of epidermal growth factor on resveratrol-induced apoptosis in prostate cancer cells is mediated by protein kinase C-α", *Mol. Cancer Ther.*, 3:1355-1363 (2004).
Stefani et al., "The Effect of Resveratrol on a Cell Model of Human Aging", *Ann. NY Acad. Sci.*, 1114:407-418 (2007).
Tang et al., "Resveratrol-induced cyclooxygenase-2 facilitates p53-dependent apoptosis in human breast cancer cells", *Mol. Cancer Ther.*, 5(8):2034-2042 (2006).
Tol et al., "Chemotherapy, Bevacizumab, and Cetuximab in Metastatic Colorectal Cancer", *N. Engl. J. Med.*, 360(6):563-572 (2009).
Tzirogiannis et al., "Enhanced Proliferation of Human Lung Adenocarcinoma and Small Cell Lung Carcinoma Cells Directed from the Cell Surface by Thyroid Hormone", in *89th Annual Meeting, The Endocrine Society* (2007) (Abstract Only).
Van Cutsem et al., "Cetuximab and Chemotherapy as Initial Treatment for Metastatic Colorectal Cancer", *N. Engl. J. Med.*, 360:1408-1417 (2009).
Yalcin et al., "Tetraidothyroacetic Acid (Tetrac) and Tetrac Nanoparticles Inhibit Growth of Human Renal Cell Carcinoma Xenografts", *Anticancer Res.*, 29:3825-3832 (2009).
Yalcin et al., "Tetraiodothyroacetic Acid and Tetraiodothyroacetic Acid Nanoparticle Effectively Inhibit the Growth of Human Follicular Thyroid Cell Carcinoma", *Thyroid*, 20(3):281-286 (2010).
Yonkers et al., "Sensory Neuron Sodium Current Requires Nongenomic Actions of Thyroid Hormone During Development", *J. Neurophysiol.*, 100:2719-2725 (2008).
Zhang et al., "Oestrogen inhibits resveratrol-induced post-translational modification of p53 and apoptosis in breast cancer cells", *Br. J. Cancer*, 91:178-185 (2004).
Avgoustakis, et al., "PLGA-mPEG nanoparticles of cisplatin: in vitro nanoparticle degradation, in vitro drug release and in vivo drug residence in blood properties" J. Contr. Rel. 2002, 79, 123-135. 13 pages.
Office Action (Mail Date Sep. 4, 2014) for U.S. Appl. No. 12/947,389, filed Nov. 16, 2010.
Office Action (Mail Date Oct. 24, 2013) for U.S. Appl. No. 12/816,287, filed Jun. 15, 2010.
Office Action (Mail Date May 8, 2014) for U.S. Appl. No. 12/816,287, filed Jun. 15, 2010.
Office Action (Mail Date May 23, 2012), for U.S. Appl. No. 12/816,287, filed Jun. 15, 2010.
Office Action (Mail Date Oct. 16, 2014), for U.S. Appl. No. 12/644,493, filed Dec. 22, 2009.
Kitevska et al., "Caspase-2: controversial killer or checkpoint controller?", Apoptosis, 14:829-848(2009) 20 pages.
Kleczkowska et al., "Differntial poly(ADP-ribose) metabolism in repair-proficient and repair-deficient murine lymphoma cells", Mut. Res., 235:93-99 (1990) 7 pages.
Klunk et al., "Development of Small Molecule Probes for the Beta-Amyloid Protein of Alzheimer's Disease", Neurobiol. Aging, 15(6):691-698 (1994) 8 pages.
Kobayashi et al., "Drug Delivery Catheter." Surg. Front. 9.1(2002):55-57 3 pages.
Konno et al., "Antiogenetic therapy for carcinoma", Igaku No Ayumi, 194(10): 824-828 (2000) 5 pages.
Koyama et al., "Recent Status and Future Perspectives in Therapeutic Angiogenesis", Prog. Med., 22(12):3070-3076 (2002) (English Abstract) 7 pages.
Kramer et al., "Human Microvascular Endothelial Cells Use β1 and β3 Integrin Receptor Complexes to Attach to Laminin", J. Cell Biol., 111:1233-1343 (1990) 11 pages.
Kumar et al., "Enhancing Effect of Thyroxine on Tumor Growth and Metastases in Syngeneic Mouse Tumor Systems", Cancer Res., 39:3515-3518 (1979) 4 pages.
Kuroki et al., "Diabetic retinopathy—The mechanisms of the ocular neovascularization of the development of anti-angiogenic drugs-", Nippon Rinsho, 57(3):584-589 (1999) (English Abstract Only) 6 pages.
Kwok et al., "Differences in EGF rated radiosensitisation of human squamous carcinoma cells with high and low numbers of EGF receptors", Br. J. Cancer, 64:251-254 (1991) 4 pages.
Lawler et al., "Cell Attachment to Thombospondin: The Role of ARG-GLY-ASP, Calcium and Integrn Receptors", J. Cell Biol., 107(6 Pt. 1): 2351-2361 (1988) 11 pages.
Letterio et al., "Maternal Rescue of Transforming Growth Facotr-β1 Null Mice", Science, 264:1936-1938 (1994) 4 pages.
Lin et al., "Androgen-induced human breast cancer cell proliferation is mediated by discrete mechanisms in estrogen receptor-α-positive and -negative breast cancer cells", J. Steroid Biochem. Mol. Biol., 113:182-188 (2009) 7 pages.
Lin et al., "Identification of the Putative MAP Kinase Docking Site in the Thyroid Hormone Receptor-β1 DNA-Binding Domain: Functional Consequences of Mutations at the Docking Site", Biochem., 42:7571-7579 (2003) 9 pages.
Lin et al., "The pro-apoptotic action of stilbene-induced COX-2 in cancer cells: Convergence with the anti-apoptotic effect of thyroid hormone", Cell Cycle, 8(12):1877-1882 (2009) 6 pages.

(56) References Cited

OTHER PUBLICATIONS

Liu et al., "Calcineurin Is a Common Target of Cyclophilin-Cyclosporin A and FKBP-FK506 Complexes", Cell, 66:807-815 (1991) 9 pages.
Lorger et al., "Activation of tumor cell integrin α□β3 controls angiogenesis and metastatic growth in the brain", Proc. Natl. Acad. Sci. U.S.A., 106(26):10666-10671 (2009) 7 pages.
Lyons et al., "The Expression of an N-CAM Serum Fragment is Positively Correlated with Severity of Negative Featues in Type II Schizophrenia", Biol. Psychiatry, 23:769-775 (1988) 7 pages.
Mahmood et al., "An N2S2 Teradentate Chelate for Solid-Phase Synthesis: Evaluation in Solution and Solid Phase and Characterization of Technetium-99 Complexes", Technetium, Rhenium and Other Metals in Chemistry and Nuclear Medicine, 5:71-76 (1999) 6 pages.
Mandelin et al., "Extracellular and Intracellular Mechanisms That Mediate the Metastatic Activity of Exogenous Osteopontin", Cancer, 115:1753-1764 (2009) 12 pages.
Mangale et al., "Identification of genes regulated by an interaction between α□β3 integrin and vitronectin in murine decidua", Reprod. Fertil. Dev., 20:311-319 (2008) 10 pages.
Markgraf et al., "Sensorimotor and cognitive consequences of middle cerebral artery occlusion in rates", Brain Res., 575(2):238-246 (1992) 10 pages.
Masson-Gadais et al., "Integrin α□β3 requirement for VEGFR2-mediated activation of SAPK2/p38 and Hsp90-dependent phosphorylation of focal adhesion kinase in endothelial cells activated by VEGF", Cell Stress Chaperones, 8(1):37-52 (2003) 16 pages.
McCarty et al., "Promises and Pitfalls of Anti-Angiogenic Therapy in Clinical Trials." Trends Mol. Med. 9.2(2003):53-58 6 pages.
Meneses et al., "Recombinant angiostatin prevents retinal neovascularization in a murine proliferative retinopathy model", Gene Therapy, 8(8):646-648 (2011) 3 pages.
Mezosi et al., "Nongenomic effect of thyroid hormone on free-radical production in human polymorphonuclear leukocytes", J. Endocrinol., 185:121-129 (2005) 9 pages.
Mishkin et al., "Increased Survival of Rats Bearing Morris Hepatoma 7800 after Induction of Hypothroidism", Cancer Res., 39:2371-2375 (1979) 5 pages.
Miyaguchi et al., "Correlation of Epidermal Growth Factor Receptor and Radiosensitivity in Human Maxillary Carcinoma Cell Lines", ActaOtolaryngol., 118:428-431 (1998) 4 pages.
Moeller et al., "Cytosolic Action of Thyroid Hormone Leads to Induction of Hypoxia-inducible Factor-1α and Glycolytic Genes", Molec. Endo., 19(12):2955-2963 (2005) 9 pages.
Mohamed et al., "Wound healing properties of cimetidine in vitro", Drug Intell. Clin. Pharm., 20(12):973-975 (1986) 4 pages.
Monferran et al., "α□β3 and α□β5 integrins control glioma cell response to ionising radiation through ILK and RhoB", Int. J. Cancer, 123:357-364 (2008) 8 pages.
Morand et al., "Effect of Iodide on Nicotinamide Adenine Dinucleotide Phosphate Oxidase Activity and Duox2 Protein Expression in Isolated Porcine Thyroid Follicles", Endo., 144(4):1241-1248 (2003) 8 pages.
Moreno et al., "Thyroid Economy—Regulation, Cell Biology, Thyroid Hormone Metabolism and Action: The Special Edition: Metabolic Effects of Thyroid Hormones. Metabolic Effects of Thyroid Hormone Derivatives", Thyroid, 18 (2):239-253 (2008) 15 pages.
Mousa et al., "Cellular and Molecular Mechanisms of Nicotine's Pro-Angiogenesis Activity and Its Potential Impact on Cancer", J. Cell. Biochem., 97:1370-1378 (2006) 9 pages.
Mousa et al., "Discovery of Pro-Angiogenic Effects of Nicotine's Pro-Angiogenesis Activity and Its Potential Impact on Cancer", J. Cell. Biochem., 97:1370-1378 (2006) Abstract Only. 3 pages.
Mousa et al., "Discovery of pro-angiogenic effects of thyroid hormone analogs", Database Biosis (Online) Biosciences Information Service, Database Accession No. PREV20040016169 (Nov. 16, 2003).

Mousa et al., "Pro-angiogenesis action of thyroid hormone and analogs in a three-dimensional in vitro microvascular endothelial sprouting model", Int. Angiol., 25(4):407-413 (2006) 7 pages.
Mousa et al., "Tetraiodothyroacetic (tetrac) inhibits angiogenesis", In: Program of the 77th Annual Meeting of the American Thyroid Association, Phoenix, AZ, 2006: Abstract 108. 4 pages.
Mousa et al., "The Proangiogenic Action of Thyroid Hormone Analogue GC-1 Is Initiated at an Integrin", J. Cardiovasc. Pharmacol., 46(3):356-360 (2005) 6 pages.
Mousa, et al., "Pro-angiogenesis action of thyroid hormone and analogs in a three-dimensional in vitro microvascular endothelial sprouting model", Int. Angiol., 25(4):407-413 (2006).
Mousa, S.A., "Mechanisms of Angiogenesis: Potential Therapeutic Targets", in Angiogenesis Inhibotors and Stimulators: Potential Therapeutic Implications, Landes Bioscience, Georgetown, Texas, Chapter I, pp. 1-12 (2000) 14 pages.
Mousa, S.A., et al., "Effect of Resveratrol on Angiogenesis and Platelet/Fibrin-Accelerated Tumor Growth in the Chick Chorioallantoic Membrane Model," Nutr. Cancer, 52(1):59-65 (2005) 7 pages.
Muller et al., "The Double Life of the Ku Protein: Facing the DNA Breaks and the Extracellular Environment", Cell Cycle, 4(30:438-441 (2005) 4 pages.
Ndiaye et al., "Red wine polyphenol-induced, endothelium-dependent NO-mediated relaxation is due to the redox-sensitive PI3-kinase / Akt-dependent phosphorylation of endothelial NO-synthase in the isolated porcine coronary artery", FASEB J., 19(3):455-457 (2005) 3 pages.
Nehls et al., "A microcarrier-based concultivation system for the investigation of factors and cells involved in angiogenesis in three-dimensional fibrin matrices in vitro", Histochem. Cell Biol., 104(6):459-466 (1995) 8 pages.
Nehls et al., "A Novel Micrcarrier-Based in Vitro Assay for Rapid and Reliable Quantification of Three-Domensional Cell Migration and Angiogenesis", Microvasc. Res., 50(3):311-322 (1995) 12 pages.
Neises et al., "Esterification of Carboxylic Acids with Dicyclohexylcarbodiimide/4-Dimethylaminopyridine: tert-Butyl Ethyl Fumarate", Org. Synth., 7:93 (1990); 63:183 (1985) 3 pages.
Newcomb et al., "Radiation Sensitivity of GL261 Murine Glioma Model and Enhanced Radiation Response by Flavopiridol", Cell Cycle., 5(1):93-99 (2006) 7 pages.
Nickoloff et al., "Aberrant Production of Interleukin-8 and Thrombospondin-1 by Psoriatic Keratinocytes Mediates Angiogenesis." Am. J. Pathol. 144.4(1994):820-828 9 pages.
Nilsson et al., "Evidence for Multiple Thyroxine-binding Sites in Human Prealbumin", J. Biol. Chem., 246(19): 6098-6105 (1971) 8 pages.
Ning et al., "Anti-integrin monoclonal antibody CNTO 95 enhances the therapeutic efficacy of fractionated radiation therapy in vivo", Mol. Cancer Ther., 7(6):1569-1578 (2008) 10 pages.
Okada et al., "A Quantitative in vivo Method of Analyzing Human Tumor-induced Angiogenesis in Mice Using Agarose Microencapsulation and Hemoglobin Enzyme-linked Immunosorbent Assay", Jpn. J. Cancer Res., 86(12):1182-1188 (1995) 7 pages.
Pages et al., "Signaling Angiogenesis via p42/p44 MAP Kinase Cascade", Ann. N.Y. Acad., Sci., 902:187-200 (2000) 14 pages.
Painter et al., "Membrane initiation of DNA synthesis", Nature, 270:543 (1977) 1 page.
Panter et al., "Pretreatment with NMDA antagonists limits release of excitatory amino acids following traumatic brain injury", Neurosci. Lett., 136(2):165-168 (1992) 4 pages.
Pardridge, W.M., "Receptor-Mediated Peptide Transport through the Blood-Brain Barrier", Endocrine Rev., 7 (3):314-330 (1986) 18 pages.
Park et al., "Effects of Tetramethoxystilbene on Hormone-Resistant Breast Cancer Cells: Biological and Biochemical Mechanisms of Action", Cancer Res., 67:5717-5726 (2007) 10 pages.
Parveen, et al., "Polymeric nanoparticles for cancer therapy", Journal of Drug Targeting, 16(2): 108-123, Feb. 2008. 16 pages.
Penno et al., "Rapid and quantitative in vitro measurement of cellular chemotaxis and invasion", Meth. Cell Sci., 19:189-195 (1997) 7 pages.

(56) References Cited

OTHER PUBLICATIONS

Pirola, et al., "Resveratrol: One Molecule, Many Targets", IUBMB Life, vol. 60, Issue 5, pp. 323-332. 10 pages.
Powell, J., "The Serial Analysis of Gene Expression", in Meth. Mol. Biol., Chapter 20, 99:297-319 (2000) 23 pages.
Pujol et al., "Letter to the editors: Preventioon of thyroid neoplasm recurrence with Triac and levothyroxine", Clin. Endocrinol., 46(1):121-122 (1997) 2 pages.
Raue et al., "Multiple Endocrine Neoplasia Type 2", Horm. Res., 68(Suppl.5): 101-104 (2007) 4 pages.
Rayalam et al., "Resveratrol induces apoptosis and inhibits adipogenesis in 3T3-L1 adipocytes", Phytother. Res., 22:1367-1371 (2008) 5 pages.
Reinholt et al., "Osteopontin—a possible anchor of osteoclasts to bone", Proc. Natl. Acad. Sci. U.S.A., 87:4473-4475 (1990) 3 pages.
Remsen et al., "Antibodies to the Neural Cell Adhesion Molecule Disrupt Functional Recovery in Injured Nerves", Exp. Neurol., 110:268-273 (1990) 6 pages.
Ren et al., "Regulation of tumor angiogenesis by thrombospondin-1", Biochim. Biophys. Acta. 1765: 178-188 (2006) 11 pages.
Risau, W., "Mechanisims of angiogenesis", Nature, 386:671-674 (1997) 4 pages.
Sahni et al., "Stimulation of endothelial cell proliferation by FGF-2 in the presence of fibrinogen requires $\alpha\beta3$", Blood, 104(12):3635-3641 (2004) 7 pages.
Saito et al., "Vector-mediated delivery of 125I-labeled β-amyloid peptide Aβ1-40 through the blood-brain barrier and binding to Alzheimer disease of the Aβ1-40/vector complex", Proc. Natl. Acad. Sci. US, 92:10227-10231 (1995) 5 pages.
Samuels et al., "Depletion of L-3-5-3'-Triiodothyronine and L-Thyroxine in Euthyroid Calf Serum for Use in Cell Culture Studies of the Action of Thyroid Hormone", Endo., 105(1):80-85 (1979) 6 pages.
SAS/STAT Guide for Personal Computers, Version 6 Edition, p. 717 (1987) 3 pages.
Sato et al., "Neovascularization: General Remarks", Biotherapy, 15(6):631-636 (2001) (English Abstract) 6 pages.
Scanlan et al., "3-Iodothyronamine is an endogenous and rapid-acting derivative of thyroid hormone", Nat. Med., 10 (6):638-642 (2004) 5 pages.
Scanlan et al., "Selective thyrmimetics: Tissue-selective thyroid hormone analogs", Curr. Opin. Drug Discov. Dev., 4 (5):614-622 (2001) 9 pages.
Schlange et al., "Autocrine WNT signaling contributes to breast cancer cell proliferation via the canonical WNT pathway and EGFR transactivation", Breast Cancer Res., 9:R63 (2007) 15 pages.
Schlumberger et al., "New therapeutic approaches to treat medullary thyroid carcinoma", Nat. Clin. Prac. Endocrinol. Metab., 4(10):22-32 (2008) 11 pages.
Schnell et al., "Expression of alpha v beta 3 integrin in patients with high and low grade glioma", Proc. Amer. Assoc. Cancer Res., 47:226 (2006) Abstract Only. 5 pages.
Schnell et al., "Expression of Integrin $\alpha\beta3$ in Gliomas Correlates with Tumor Grade and Is not Restricted to Tumor Vasculature", Brain Pathol., 18:378-386 (2008) 9 pages.
Schreiber et al., "Hormone delivery systems to the brain-transhyretin", Exp. Clin. Endocrinol Diabetes, 103(2): 75-80 (1995) 7 pages.
Schueneman et al., "SU11248 Maintenance Therapy Prevents Tumor Regrowth after Fractionated Irradiation of Murine Tumor Models", Cancer Res., 63:4009-4016 (2003) 8 pages.
Shih et al., "Thyroid Hormone Promotes Serine Phosphorylation of p53 by Mitogen-Activated Protein Kinase", Biochem., 40:2870-2878 (2001) 10 pages.
Shih et al., "Disparate Effects of Thyroid Hormone on Actions of Epidermal Growth Factor and Transforming Growth Factor-α Are Mediated by 3,5'-Cyclic Adenosine 5'-Monophosphate-Dependent Protein Kinase II", Endo., 145(4): 1708-1717 (2004) 10 pages.
Shinohara et al., "Enhanced radiation damage of tumor vasculature by mTOR inhibitors", Oncogene, 24:5414-5422 (2005) 9 pages.
Skrovronsky et al., "In vivo detection of amyloid plaques in a mouse model of Alzheimer's disease", Proc. Natl. Acad. Sci US, 97(13):7609-7614 (2000) 6 pages.
Skuli et al., "$\alpha\beta3/\alpha\beta5$ integrins-FAK-RhoB: A Novel Pathway for Hypoxia Regulation in Glioblastoma", Cancer Res., 69*8):3308-3316 (2009) 9 pages.
Song et al., "Formulation and characterization of biodegradable nanoparticles for intravascular local drug delivery", J. Controlled Rel., 43:197-212 (1997) 16 pages.
Strieth, et al., "Antiangiogenic combination tumor therapy blocking $\alpha$-integrins and VEGF-receptor-2 increases therapeutic effects in vivo", Int. J. Cancer, 119:423-431 (2006) 9 pages.
Sunwoo et al., "Novel Proteasome Inhibitor PS-341 Inhibits Activation of Nuclear Factor-κB, Cell Survival, Tumor Growth, and Angiogenesis in Squamous Cell Carcinoma", Clin. Cancer Res., 7:1419-1428 (2001) 10 pages.
Szatmari et al., "Detailed characterization of the mouse glioma 261 tumor model for experimental glioblastoma therapy", Cancer Sci., 97(6):546-553 (2006) 8 pages.
Szumiel, I., "Ca2+, Mg2+ and (Adenosine Diphosphate Ribose)n in Cellular Response to Irradiation", J. Theor. Biol., 101:441-451 (1983) 11 pages.
Takemaru et al., "Chibby, a nuclear β-catenin-associated antagonist of the Wnt/Wingless pathway", Nature, 422:905-909 (2003) 5 pages.
Tang et al., "Thyroid Hormone Causes Mitogen-Activated Protein Kinase-Dependent Phosphorylation of the Nuclear Estrogen Receptor", Endocrinol., 145(7):3265-3272 (2004) 8 pages.
Tator et al., "Review of the secondary injury theory of acute spinal cord trauma with emphasis on vascular mechanisms", J. Neurosurg., 75(1):15-26 (1991) 13 pages.
Theodossiou et al., "Propylthiouracil-induced Hypothyroidism Reduces Xenograft Tumor Growth in Athymic Nude Mice", Cancer, 86:1596-1601 (1999) 6 pages.
Thompson et al., "The Clinical Manipulation of Angiogenesis: Pathology, Side-Effects, Surprises, and Opportunites with Novel Human Therapies." J. Pathol. 190(2000):330-337 8 pages.
Thraves et al., "Radiosensitization of Human Fibroblasts by 3-Aminobenzamide: An Inhibitor of Poly(ADP-Ribosylation)", Radiat Res., 104:119-127 (1985) 9 pages.
Tomanek et al., "A Thyroid Hormone Analog Stimulates Angiogenesis in the Post-infarcted Rat Heart", J. Mol. Cell Cardiol., 30(5):923-932 (1998) 10 pages.
Tomanek et al., "Angiogenesis: New Insights and Therapeutic Potential", Anatomical Record (New Anat.), 261:126-135 (2000) 10 pages.
Tomanek et al., "Early Coronary Angiogenesis in Resposne to Thyroxine: Growth Characteristics and Upregulation of Basic Fibroblast Growth Factor", Circ. Res., 82(5):587-593 (1998) 8 pages.
Tomanek et al., "Growth of the Coronary Vasculature in Hypertrophy: Mechanisms and Model Dependence", Cell. Mol. Bio. Res., 40(2):129-136 (1994) 8 pages.
Toms et al., "Thyroid Hormone Depletion Inhibits Astrocytoma Proliferation via a p53-Independent Induction of p21 (WAF/1CIP1)", Anticancer Res., 18:289-293 (1998) 5 pages.
Tuttle et al., "Recombinant Human TSH-Assisted Radioactive Iodine Remnant Ablation Achieves Short-Term Clinical Recurrence Rates Similar to Those of Traditional Thyroid Hormone Withdrawal", J. Nucl. Med., 49(5):764-770 (2008) 7 pages.
Utsumi et al., "Potentially Lethal Damage Versus Sublethal Damage: Independent Repair Processes in Actively Growing Chinese Hamster Cells", Radiat. Res., 77:346-360 (1979) 9 pages.
Van Waes et al., "Effects of the novel $\alpha$ integrin antagonist SM256 and cis-platinum on growth of murine squasmos cell carcinoma PAM LY8", Int. J. Oncol., 16(6):1189-1195 (2000) 8 pages.
Varnes et al., "The Effect of pH on Potentially Lethal Damage Recovery in A549 Cells", Radiat. Res., 108:80-90 (1986) 11 pages.
Velasco et al., "Dermatological Aspects of Angiogenesis." Brit. J. Dermatol. 147(2002):841-852 12 pages.
Wang et al., "DITPA stimulated bFGF, VEGF, angiopoietin, and Tie-2 and facilates coronary arteriolar growth", Am. J. Physiol. Heart Circ. Physiol., 284(2):H613-H618 (2003) 6 pages.

(56) References Cited

OTHER PUBLICATIONS

Wang et al., "Integrin-associated Protein Stimulates α2β1-dependent Chemotaxis via Gi-mediated inhibition of Adenylate Cyclase and Extracelular-regulated Kinases", J. Cell. Biol., 147:389-399 (1999) 11 pages.

Wen et al., "Prognostic Value of EGFR and TGF-α in Early Laryngeal Cancer Treated With Radiotherapy", Laryngoscope, 106(7):884-888 (1996) 6 pages.

Werdelin et al., "Neuropeptides and neural cell adhesion molecule (NCAM) in CSF from patients with ALS", Acta Neurol. Scand., 79(3):177-181 (1989).

Wilkinson, J.H., "Synthesis of some Possible Metabolites of Thyroxine and Triiodothyronine", Biochem. J., 63:601-605 (1956) 5 pages.

Xia et al., "Chemokines/chemokine receptors in the central nervous system and Alzheimer's disease", J. NeuroVirol., 5:32-41 (1999) 11 pages.

Yalcin et al., "Tetraiodothyroacetic Acid (Tetrac) and Nanoparticulate Tetrac Arrest Growth of Medullary Carcinoma of the Thyroid", J. Clin. Endocrinol. Metab., 95(4):1972-1980 (2010) 7 pages.

Yalcin et al., "Tetraiodothyroacetic Acid (Tetrac) and Nanoparticulate Tetrac Arrest Growth of Medullary Carcinoma of the Thyroid", J. Clin. Endocrinol. Metab., 95(4):1972-1980 (2010) 9 pages.

Yanase et al., "Role of N-methyl-D-aspartate receptor in acute spinal cord injury", J. Neurosurg., 83:884-888 (1995) 6 pages.

Yang et al., "Rab7b, a novel lysosome-associated small GTPase, is involved in monocytic differentiation of human acute promyelocytic leukemia cells", Biochem. Biophys. Res. Commun., 318:792-799 (2004) 8 pages.

Yang, et al., "Enhanced inhibition of adipogenesis and induction of apoptosis in 3T3-L1 adipocytes with combinations of resveratrol and quercetin", Life Sci., 82:1032-1039 (2008) 8 pages.

Young, W., "Role of Calcium in Central Nervous System Injuries", J. Neurotrauma, 9(Suppl. 1): S9-S25 (1992) 18 pages.

Young, W., "Secondary injury mechanisms in acute spinal cord injury", J. Emerg. Med., 11:13-22 (1993) 11 pages.

Yu et al., "Osteopontin Gene is Expressed in the Dermal Papilla of Pelage Follicles in a Hair-Cycle-Dependent Manner", J. Invest. Dermatol., 117:1554-1558 (2001) 5 pages.

Yu, et al., "The Compressor Silencing Mediator for Retinoid and Thyroid Hormone Receptor Facilitates Cellular Recovery from DNA Double-Strand Breaks", Cancer Res., 66(18):9316-9322 (2006) 7 pages.

Zhang et al., "Quantitative PET Imaging of Tumor Integrin αvβ3 Expression with 18F-FRGD2", J. Nucl. Med., 47:113-121 (2006) 9 pages.

Zhen et al., "Synthesis and Amyloid Binding Properties of Rhenium Compleses: Preliminary Progress Toward a Reagent for SPECT Imaging of Alzheimer's Disease Brain", J. Med. Chem., 42:2805-2815 (1999) 11 pages.

Zhuang et al., "99mTc-Labeled MIBG Derivatives: Novel 99m Tc Complexes as Myocardial Imaging Agents for Sympathetic Neurons", Bioconjugate Chem., 10:159-168 (1999) 10 pages.

Office Action (Mail Date Apr. 11, 2013) for U.S. Appl. No. 12/816,287, filed Jun. 15, 2010.

Office Action (Mail Date Apr. 8, 2013) for U.S. Appl. No. 11/786,723, filed Apr. 11, 2007.

Office Action (Mail Date Apr. 2, 2013) for U.S. Appl. No. 13/156,047, filed Jun. 8, 2011.

Office Action (Mail Date Apr. 29, 2013) for U.S. Appl. No. 13/345,194, filed Jan. 6, 2012.

Blight, A.R., "Macrophages and Inflammatory Damage in Spinal Cord Injury", J. Neurotrauma, 9(Suppl. 1):S83-S91 (1992) 10 pages.

Blood et al., "Tumor interactions with the vasculature: angiogenesis and tumor metastasis", Bioch. Biophys. Acta, 1032:89-118 (1990) 30 pages.

Bornebroek et al., "Potential for imaging cerebral amyloid deposits using 123I-labelled serum amyloid P component and SPET", Cucl. Med. Commun., 17:929-933 (1996) 6 pages.

Bozarth et al., "An improved method for the quantitation of cellular migration: Rose of α□β3 integrin in endothelial and smooth muscle cell migration", Meth. Cell Sci., 19(3):179-187 (1997) 9 pages.

Braughler et al., "Involvement of Lipid Peroxidation in CNS Injury", J. Neurotrauma, 9(Suppl. 1):S1-S7 (1992) 8 pages.

Notice of Allowance (Mail Date Oct. 4, 2013) for U.S. Appl. No. 11/786,723, filed Apr. 11, 2007.

Office Action (Mail Date Oct. 15, 2013) for U.S. Appl. No. 13/345,194, filed Jan. 6, 2012.

Abdollahi et al., "Inhibition of α□β3 Integrin Survival Signaling Enhances Antiangiogenic and Antitumor Effects of Radiotherapy", Clin. Cancer Research., 11(17):6270-6279 (2005) 10 pages.

Albert et al., "Integrin α□β3 Antagonist Cilengitide Enhances Efficacy of Radiotherapy in Endothelial Cell and Non-Small-Cell Lung Cancer Models", Int. J. Radiat. Oncol. Biol. Phys., 65(5):1536-1543 (2006) 8 pages.

Alexis et al., "Nonocclusive Common Carotid Artery Thrombosis in the Rat Results in Reversible Sensorimotor and Cognitive Behavorial Deficits", Stroke, 26:2338-2346 (1995) 16 pages.

Ali et al., "Angiogenesis as a potential biomarker in prostate cancer chemoprevention trials", Urology, 57(Suppl 4A):143-147 (2001) 5 pages.

Ali et al., "Apoptosis-Inducing effect of erlotinib is potentiated by 3,3'-diindolylmethane in vitro and in vivo using an orthotopic model of pancreatic cancer", Mol. Cancer Ther., 7(6):1708-1719(2008) 12 pages.

Ali et al., "High levels of oestrogen receptor-α in tumorigenesis: inhibition of cell growth and angiogenic factors", Cell Prolif., 34(4):223-231 (2001) 10 pages.

Allen, A.R., "Surgery of experimental lesion of spinal cord equivalent to crush injury of fracture dislocation of spinal column", J. Am. Med. Assoc., 57(11):878-880 (1911) 4 pages.

Almog et al., "Transcriptional Switch of Dormant Tumors to Fast-Growing Angiogenic Phenotype", Cancer Res., 69 (3):836-844 (2009).

Amirkhosravi et al., "Antimestatatic effect of tinzaparin, a low-molecular-weight heparin", J. Thromb. Haemost., 1:1972-1976 (2003) 5 pages.

Amirkhosravi et al., "Inhibition of tumor cell-induced platelet aggregation and lung metastasis by the oral GpIIb/IIIa antagonist XV454", J. Thrombosis and Haemostasis, 3:549-554 (2003) 6 pages.

Ando et al., "Induction by carbon-ion irradiation of the expression of vascular endothelial growth factor in lung carcinoma cells", Int. J. Radiat. Biol., 76(8):1121-1127 (2000) 7 pages.

Application No. PCT/US2004/030583, International Search Report and the Written Opinion of the International Searching Authority, or the Declaration dated Mar. 7, 2005. 11 pages.

Application No. PCT/US2005/032813, International Search Report dated Dec. 22, 2006. 6 pages.

Application No. PCT/US2007/009026, International Search Report dated Nov. 7, 2008. 5 pages.

Application No. PCT/US2009/069104, International Search Report dated Mar. 4, 2010 5 pages.

Application No. PCT/US2007/026167, International Search Report dated Oct. 30, 2008. 3 pages.

Application No. PCT/US2010/038700, International Search Report dated Mar. 21, 2011. 4 pages.

Application No. PCT/US2006/036243, International Search Report dated Jul. 30, 2007. 7 pages.

Application No. PCT/US2010/029371, International Search Report dated Aug. 24, 2010. 5 pages.

Audus et al., "Bovine Brain Microvessel Endothelial Cell Monolayers as a Model System for the Blood-Brain Barrier", in Biological Approaches to the Controlled Delivery of Drugs, Ann. N.Y. Acad. Sci., 507:9-18 (1987) 11 pages.

Avis, K.E., "Parenteral Preparations", in Remington's Pharmaceutical Sciences, 15th Ed., Chapter 84, pp. 1461-1487, Mack Publishing Co., Easton, Pennsylvania (1975) 29 pages.

Balestrazzi et al., "Leaf-associated bacteria from transgenic white poplar producing resveratrol-like compounds: isolation, molecular characterization, and evaluation of oxidative stress tolerance", Can. J. Microbiol., 55:829-840 (2009) 12 pages.

(56) References Cited

OTHER PUBLICATIONS

Bederson et al., "Rat Middle Cerebral Artery Occlusion: Evaluation of the Model and Development of a Neurologic Examination", Stroke, 17(3):472-476 (1986) 6 pages.
Belenky et al., "NAD+ metabolism in health and disease", Trends Biochem. Sci., 32(1):12-19 (2007) 9 pages.
Benedetti et al., "Life Tables and Survivor Functions", in BMDP Statistical Software Manual, BMDP Statistical Software, Inc., vol. 2, p. 573 and 689-718 (1988) 33 pages.
Ben-Hur et al., "Thermally Enhanced Radioresponse of Cultured Chinese Hamster Cells: Inhibition of Repair of Sublethal Damage and Enhancement of Lethal Damage", Radiat Res., 58:38-51 (1974) 14 pages.
Bennett et al., "A peptide derived from α-fetoprotein prevents the growth of estrogen-dependent human breast cancers sensitive and resistant to tamoxifen", Proc. Natl, Acad. Sci. USA, 99(4):2211-2215 (2002) 5 pages.
Bergers et al., "Modes of resistance to anti-angiogenic therapy", Nat. Rev. Cancer, 8(8):592-603 (2008) 23 pages.
Bergstrom et al., "Iodine-123 labelled Z-(R,R)-IQNP: a potential radioligand for visualization of M1 and M2 muscarinic acetylcholine receptors in Alzheimer's disease", Eur. J. Nucl. Med., 26(11):1482-1485 (1999).
Bergstrom et al., "Reduction of fibrinogen absorption on PEG-coated polystyrene surfaces", J. Biomed. Mat. Res., 26:779-790 (1992) 12 pages.
Bhat et al., "NCAM-180, the largest component of the neural cell adhesion molecule, is reduced in dysmyelinating quaking mutant mouse brain", Brain Res., 452:373-377 (1988) 5 pages.
Office Action (Mail Date Feb. 25, 2014) for U.S. Appl. No. 13/156,047, filed Jun. 8, 2011.
Office Action (Mail Date Mar. 12, 2014) for U.S. Appl. No. 12/947,389, filed Nov. 16, 2010.
Notice of Allowance (Mail Date Feb. 6, 2014) for U.S. Appl. No. 13/345,194, filed Jan. 6, 2012.
Folkman, J., "Angiogenesis in cancer, vascular, rheumatoid and other disease", Nat. Med., 1(1):27-31 (1995) 5 pages.
Freese et al., "Characterization and mechanism of glutamate neurotoxicity in primary striatal cultures", Brain Res., 521 (1/2):254-264 (1990) 12 pages.
Fujii et al., "Crystal Structure of Trimestatin, a Disintegrin Containing a Cell Adhesion Recognition Motif RGD", J. Mol. Biol., 332:1115-1122 (2003) 8 pages.
Gavrieli et al., "Identification of Programmed Cell Death In Situ via Specific Labeling of Nuclear DNA Fragmentation", J. Cell. Biol., 119(3):493-501 (1992) 9 pages.
GenBank Accession No. NM_002210, Jun. 15, 2008 8 pages.
Geng et al., "A Specific Antagonist of the p110σ Catalytic Component of Phosphatidylinositol 3'-Kinase, IC486068, Enchances Radiation-Induced Tumor Vascular Destruction", Cancer Res., 64:4893-4899 (2004) 7 pages.
Ginis et al., "Hypoxia affects tumor cell invasiveness in vitro: the role of hypoxia-activated ligand HAL 1/13 (Ku 86 autoantigen)", Cancer Lett., 154:163-174 (2000) 12 pages.
Gladson, C.L., "Expression of integrin α□β3 in Small Blood Vessels of Giioblastoma Tumors", J. Neurpath. Exp. Neurol., 55(11):1143-1149(1996) 7 pages.
Glinsky et al., "Classification of Human Breast Cancer Using Gene Expression Profiling as a Component of the Survival Predictor Algorithm", Clin. Cancer Res., 10:2272-2283 (2004) 12 pages.
Glinsky et al., "Gene expression prfiling predicts clinical outcome of prostate cancer", J. Clin. Invest., 113(6):913-923 (2004) 11 pages.
Glinsky et al., "Microarray analysis identifies a death-from-cancer signature predicting therapy failure in patients with multiple types of cancer", J. Clin. Invest., 115(6):1503-1521 (2005) 19 pages.
Glinsky et al., "Microarray Analysis of Xenograft-Derived Cancer Cells Lines Representing Multiple Experimental Models of Human Prostate Cancer", Mol. Carcinog., 37:209-221 (2003) 13 pages.
Goldstein et al., "Influence of Lesion Size and Location on Amphetamine-Facilitated Recovery of Beam-Walking in Rats", Behay. Neurosci., 104(2):320-327 (1990) 9 pages.
Goldstein, A., "Estimating the Error Variance and the Confidence Interval for a Regression Line", in Biostatistics, The MacMillan Co., New York, pp. 139-146 (1964) 10 pages.
Goodman, M.M., "Automated Synthesis of Radiotracers for PET Applications", in Clinical Positron Emission Tomography, Mosby Yearbook, K.F. Hubner et al., Chapter 14, pp. 110-122 (1992) 13 pages.
Grant, D.B., "Monitoring TSH concentrations during treatment for gongenital hypothyroidism", Arch. Disease Childhood, 66:669-670 (1991) 2 pages.
Gregoriadis, "Liposomes", in Drug Carriers in Biology and Medicine, Chapter 14, pp. 287-341, Academic Press (1979) 57 pages.
Guigon et al., "Regulation of β-Catenin by a Novel Nongenomic Action of Thyroid Hormone β Receptor", Mol. Cell. Biol., 28(14):4598-4608 (2008) 11 pages.
Hahn et al., "Plateau-phase cultures of mammalian cells: An in vitro model for human cancer", Curr. Top. Radiat. Res. Q., 8:39-83 (1972) 45 pages.
Halks-Miller et al., "CCR1 Immunoreactivity in Alzheimer's Disease Brains", Society for Neuroscience Meeting, Abstract #787.6, vol. 24 (1998) Abstract Only. 1 page.
Hansebout, R.R., "A Comprehensive Review of Methods of Improving Cord Recovery After Acute Spinla Cord Injury", in Early Management of Acute Spinal Cord Injury, pp. 181-196 (1982) 16 pages.
Hartert, H., "Blutgerinnungsstud Mit Der Thrombelastogeraphie, Einem Neuen Untersuchungsverfahren", Klinische Wochenschrift 26(37/38):577-583 (1948) German Language Only. 9 pages.
Hashimoto et al., "Matrix Metalloproteinases Cleave Connective Tissue Growth Factor Reactivate Angiogenic Activity of Vascular Endothelial Growth Factor 165", J. Biol. Chem. 277(39):36288-36295 (2002) 8 pages.
Heller et al., "Inhibition of potentially lethal damage recovery by altered pH, glucose utilization and proliferation in plateau growth phase human glioma cells", Int. J. Radiat. Biol., 66(1):41-47 (1994) 7 pages.
Hercbergs et al., "GL261 brain tumor cells: responses to signle or fractionated x-irradiation with the α□β3 integrin tyroxine receptor antagonist tetrac (tetraiodothyroacetic acid)", 20th EORTC-NCI-AACR Symposium on Molecular Targets and Cancer Therapeutics, Geneva, Switzerland, Oct. 2008.
Hercbergs et al., "GL261 brain tumor cells: responses to single or fractionated x-irradiation with the α□β3 integrin tyroxine receptor antagonist tetrac (tetraiodothyroacetic acid)", Euro. J. Cancer, 6(12):172 (Abstract Only) 4 pages.
Hercbergs et al., "Propylthiouracil-induced Chemical Hypothyroidism with High-Dose Tamoxifen Prolongs Survival in Recurrent High Grade Ciioma: A Phase I/II Study", Anticancer Res., 23:617-626 (2003) 10 pages.
Hercbergs, A., "The Thyroid Gland as an Intrinsic Biologic Response-Modifier in Advanced Neoplasia—A Novel Paradigm", in vivo, 10:245-247 (1996) 3 pages.
Hercbergs, et al., GL261 Brain Tumor Cells: In Vitro Single and Fractionated Dose Responses to X-Rays and Modification by Tetrac (Tetraiodothyroacetic Acid), The Cleveland Clinic Foundation, Department of Radiation Oncology 46 pages.
Hercbergs, et al., "Radiosensitization of GL261 glioma cells by tetraiodothyroacetic acid (tetrac)", Cell Cycle, 8 (16):2586-2591 (2009) 6 pages.
Hermanson, "Modification with Synthetic Polymers", in Bioconjugate Tech., Ch. 15, Academic Press, San Diego, CA, pp. 617-618 (1996) 4 pages.
Hoff et al., "Medullary Thyroid Carcinoma", Hematol. Oncol. Cin. North Am., 21(3):475-488 (2007) 14 pages.
Horuk et al., "Expression of Chemokine Receptors by Subsets of Neurons in the Central Nervous System", J. Immunol., 158:2882-2890 (1997) 9 pages.
Hubner, K F., "University of Tennessee Biomedical Imaging Center and Transfer of Technology to the Clinical Floor", in Clinical Positron Emission Tomography, Mosby Yearbook, K.F. Hubner et al., Chapter 2, pp. 4-16(1992) 13 pages.

(56) References Cited

OTHER PUBLICATIONS

Hudlicka et al., "Factors involved in capillary growth in the heart", Mol. Cell. Biochem, 147:57-68 (1995) 12 pages.
Igarashi et al., "Techniques Supporting Angiogenesis Therapy 2: DDS Technique Supporting Regenerative Medicine." Inflamm. Immun. 10.6(2002):652-658 7 pages.
Illario et al., "Fibronectin-Induced Proliferation in Thyroid Cells is Mediated by α□β3 Integrin through Ras/Raf-1/MEK/ERK and Calcium/CaMKII Signals", J. Clin. Endocrinol. Metab., 90(5):2865-2873 (2005) 9 pages.
Ingerman-Wojenski et al., "Evaluation of electrical aggregometry: comparison with optial aggregometry, secretion of ATP, and accumulation of radiolabeled platelets", J. Lab. Clin. Med., 101(1):44-52 (1983) 10 pages.
Iwata et al., "A new, convenient method for the preparation of 4-[18F]fluorobenzyl halides", Applied Radiation and Isotopes, 52(1):87-92 (2000) 7 pages.
Janssen et al., "Pathogenesis of Spinal Cord Injury and Newer Treatments—A Review", Spine, 14(1):23-32 (1989) 11 pages.
Jeffrey et al., "The preparation and characterisation of poly(lactide-co-glycolide) microparticles. 1. Oil-in-water emulsion solvent evaporation", Int. J. Pharm., 77:169-175 (1991) 7 pages.
Jordan et al., "Thyroid Status is a Key Modulator of Tumor Oxygenation: Implication for Radiation Therapy", Radiat. Res., 168:428-432 (2007) 5 pages.
Kapiszewska et al., "The Effects of Reduced Temperature and/or Starvation Conditions on the Radiosensitivity and Repair of Potentially Lethal Damage and Sublethal Damage in L5178Y-R and L5178Y-S Cells", Radiat. Res., 113:458-472 (1988) 15 pages.
Kastan et al., "A Mammalian Cell Cycle Checkpoint Pathway Utlizing P53 and GADD45 is Defective in Ataxia-Telangiectasia", Cell. 71:587-597 (1992) 11 pages.
Kawasuji et al., Jap. Circ. J., 63(Suppl. 1):65 (1999) Japanese Abstract Only. 3 pages.
Kerr et al., "Novel Small Molecule α□ Integrin Antagonists: Comparative Anti-Cancer Efficacy with Known Angiogenesis Inhibitors", Anticancer Res., 19:959-968 (1999).
Kerr et al., "Small molecule α□ integrin antagonists: novel anticancer agents", Exp. Opin. Invest. Drugs, 9 (6):1271-1279 (2000) 9 pages.
Kim et al., "Regulation of Antiogenesis in Vivo, by Ligation of Integrin α5β1 with the Central Cell-Binding Domaing of Fibronectin", Am. J. Pathol., 156(4): 1345-1362 (2000) 18 pages.
Kim et al., "Soluble Fit-1 gene delivery using PEI-g-PEG-RGD conjugate for anti-angiogenesis", J. Control Release, 106:224-234 (2005) 11 pages.
Kimelberg, H.K., "Astrocytic Edema in CNS Trauma", J. Neurotrauma, 9(Suppl. 1):S71-S81 (1992) 12 pages.
Breier et al., "The role of vascular endothelial growth factor in blood vessel formation", Trends in Cell Biol., 6:454_456 (1996) 3 pages.
Bridoux et al., "Semisynthesis and pharmacological activities of Tetrac analogs: Angiogenesis modulators", Bioorg. Med. Chem. Lett., 19:3259-3263 (2009) 5 pages.
Bridoux et al., "Semisynthesis and pharmacological activities of thyroxine analogs: Development of new angiogenesis modulators", Bioorg. Med. Chem. Lett, 20(11):3394-3398 (2010) 5 pages.
Brooks et al., "Antintegrin α□β3 blocks human breast cancer growth and angiogenesis in human skin", J. Clin. Invest., 96(4):1815-1822 (1995) 8 pages.
Burgman et al., "Effect of Inhibitors of Poly(ADP-Ribose)Polymerase on the Radiation Resposne of HeLa S3 Cells", Radiat. Res., 119:380-386 (1989) 7 pages.
Carmeliet et al., "Molecular Basis of Angiogenesis Role of VEGF and VE-Cadherin", Ann. N.Y. Acad. Sci., 902:249-264 (2000) 16 pages.
Chanoine et al., "The role of transthyretin in the transport of thyroid hormone to cerebrospinal fluid and brain", Acta Medica Austriaca, 19(Suppl. 1):25-28 (19920) 5 pages.

Charness et al., "Ethanol Increases the Expression of Functional Delta-Opioid Receptors in Neurblastoma x Glioma NG108-15 Hybrid Cells", J. Biol. Chem., 261(7):3164-3169 (1986) 6 pages.
Charo et al., "The Vitronectin Receptor α□β3 Binds Fibronectin and Acts in Concert with α5β1 in Promoting Cellular Attachment and Spreading on Fibronectin", J. Cell Biol., 111(6 Pt. 1): 2795-2800 (1990) 6 pages.
Chase et al., "Principles of Radioisotope Methodology", 2nd Ed., Minneapolis, MN. Burgess Publ. Co., 1962, pp. 68, 87-90. 7 pages.
Chavakis et al., "Kinetics of integrin expression in the mouse model of proliferative retinopathy and success of secondary intervention with cyclic RGD peptides", Diabetologia, 45:262-267 (2002) 6 pages.
Cheng et al., "Molecular Aspects of Thyroid Hormone Actions", Endocri. Rev., 31(2): 139-170 (2010) 32 pages.
Cheresh et al., "Biosynthetic and Functional Properties of an Arg-Gly-Asp-directed Receptor Involved in Human Melanoma Cell Attachment to Vitronectin, Fibrinogen and von Willibrand Factor", J. Biol. Chem., 262(36):17703-17711 (1987) 9 pages.
Cheresh, D.A., "Human endothelial cells synthesize and express an Arg-Gly-Asp-directed adhesion receptor involved in attachment to fibrinogen and von Willibrand factor", Proc. Natl. Acad. Sci. U.S.A., 84:6471-6475 (1987) 9 pages.
Chiaguri et al., "Anoikis: A necessary death program for anchorage-dependent cells", Biochem. Pharmacol., 76:1352-1364 (2008) 13 pages.
Chinese Office Action for Application No. 2004800331846 dated Mar. 5, 2010 7 pages.
Chinese Office Action for Application No. 2004800331846, mailed Nov. 30, 2007, cited CN 1126589. 6 pages.
Clifton et al., "Marked Protection by Moderate Hypothermia After Experimental Traumatic Brain Injury", J. Cereb. Blood Flow Metab., 11(1):114-121 (1991) 9 pages.
Cody et al., "Molecular modeling of the thyroid hormone interactions with α□β3 integrin", Steriods, 72:165-170 (2007) 6 pages.
Cohen-Jonathan et al., "Radioresistance Induced by the High Molecular Forms of the Basic Fibroblast Growth Factor Is Associated with an increased G2 Delay and a Hyperphosphorylation of p34CDC2 in HeLa Cells", Cancer Res., 57:1364-1370 (1997) 7 pages.
Cohen-Jonathan et al., "α□β3 integrin pathway controls glioma radioresistance through ILK", Proc. Amer. Assoc. Cancer Res., 47:5180 (2006) (Abstract Only) 2 pages.
Cox et al., "The repair of potentially lethal damage in X-irradiated cultures of normal and ataxia telangiectasia human fibroblasts", Int. J. Radiat. Biol., 39(4):357-365 (1981) 9 pages.
Cristofanilli et al., "Thyroid Hormone and Breast Carcinoma. Primary Hypothyroidism is Associated with a Reduced Incidence of Primary Breast Carcinoma", Cancer, 103(6):1122-1128 (2005) 7 pages.
Database BIOSIS [Online] Bioscience Information Service, Philadelphia, PA, US; Nov. 16, 2003, Mousa et al., "Discovery of pro-angiogenic effects of thyroid hormone and analogs", Accession No. PREV200400161659 (Abstract).
Database BIOSIS [Online], Accession No. PREV20040016159, Abstract, Mousa et al., "Discovery of pro-angiogenic effects of thyroid hormone and analogs", Blood, 102(11):77b-78b (2003) 1 page.
Davis et al., "Promotion by thyroid hormone of cytoplasm-to-nucleus shutting of thyroid hormone receptors", Steroids, 73:1013-1017 (2008) 5 pages.
Davis et al., "Thyroxine Promotes Association of Mitogen-activated Protein Kinase and Nuclear Thyroid Hormone Receptor (TR) and Causes Serine Phosphorylation of TR", J. Biol. Chem., 275(48):38032-38039 (2000) 8 pages.
De la Cruz et al., "Effect of Aspirin Plus Dipyridamole on the Retinal Vascular Pattern in Experimental Diabetes Mellitus", J. Pharmacol. Exp. Ther., 280(1):454-459 (1997) 6 pages.
Deardorff, D.L., "Isotonic Solutions", in Remington's Pharmaceutical Sciences, 15th Ed., Chapter 79, pp. 1405-1412, Mack Publishing Co., Easton (1975) 10 pages.
DeFesi et al., "3,5,3'-Triiodothyronine Effects on the Growth Rate and Cell Cycle of Cultured GC Cells", Endocrinol., 108(1):259-267(1981) 9 pages.

(56) References Cited

OTHER PUBLICATIONS

Demediuk et al., "Traumatic Spinal Cord Injury in Rats Causes Increases in Tissue Thromboxane But Not Peptidoleukotrienes", J. Neurosci. Res., 20:115-121 (1988) 7 pages.
DeRyck et al., "Neocortical localization of tactile/proprioceptive limb placing reactions in the rat", Brain Res., 573(1):44-60 (1992) 18 pages.
Di Chiro et al., "Glucose utilization of cerebral gliomas measured by [18F] fluorodeoxyglucose and positron emission tomography", Neurology, 32(12):1323-1329 (1982) 8 pages.
Dietrich et al., "Post-traumatic brain hypothermia reduces histopathological damage following concussive brain injury in the rat", Acta Neuropathol., 87(3):250-258 (1994) 10 pages.
Ding et al., "Radioprotection of Hematopoietic Tissue by Fibroblast Growth Factors in Fractionated Radiation Experiments", Acta Onocol., 36(3):337-340 (1997) 4 pages.
Dixon et al., "A fluid percussion model of experimental brain injury in the rat", J. Neurosurg., 67(1):110-119 (1987) 11 pages.
Dupont et al., "Antiangiogenic and antimetastatic properties of Neovastat (•-941), an orally active extract derived from cartilage tissue", Clin. Experim. Metastasis, 19:145-153 (2002) 9 pages.
Edwards et al., "Trypsinized BHK21 cells aggregate in the presence of metabolic inhibitors and in the absence of divalent cations", J. Cell Sci., 19(3):653-667 (1975) 16 pages.
Elkind et al., "Radiation Response of Mammalian Cells Grown in Culture. 1. Repair of X-Ray Damage in Surviving Chinese Hamster Cells", Radiat. Res., 13:556-593 (1960) 38 pages.
Elvin et al., "Cell Adhesiveness and the Cell Cycle: Correlation in Synchronized Balb/c 3T3 Cells", Biol. Cell, 48:1-10 (1983) 10 pages.
Ely and Berne, "Protective Effects of Adenosine in Myocardial Ischemia", Circulation, 85:893-904 (1992) 13 pages.
Ethier et al., "Adenosine stimulates proliferation of human endothelial cells in culture", Am. J. Physiol., 265:H131-H138 (1993) 8 pages.
Everts et al., "Uptake of 3,3',5.5'-Tetraiodothyroacetic Acid and 3,3',5'-Triiodothyronine in Cultured Rat Anterior Pituitary Cells and Their Effects on Thyrotropin Secretion", Endocrinol., 136(10):4454-4461 (1995) 8 pages.
Faden et al., "Endogenous Opioid Immunoreactivity in Rat Spinal Cord Following Traumatic Injury", Ann. Neurol., 17 (4):386-390 (1985) 5 pages.
Faden, A.I., "Experimental Neurobiology of Central Nervous System Trauma", Crit. Rev. Neurobiol., 7(3/4):175-186 (1993) 13 pages.
Feeney et al., "Amphetamine, Haloperidol, and Experience Interact to Affect Rate of Recovery After Motor Cortex Injury", Science, 217(4562):855-857 (1982) 4 pages.
Fei et al., "P53 and radiation responses", Oncogene, 22:5774-5783 (2003) 10 pages.
Felding-Habermann et al., "Integrin activation controls metastasis in human breast cancer", Proc. Natl. Acad. Sci. U.S.A., 98(4):1853-1858 (2001) 6 pages.
Feng et al., "Fibrin and Collagen Differentially Regulate Human Dermal Microfascular Endothelial Cell Integrins: Stablization of $\alpha\Box/\beta3$ mRNA by Fibrin", J. Invest. Dermatol., 113(6):913-919 (1999) 7 pages.
Fife et al., "Effects of tetracyclines on angiogenesis in vitro", Cancer Letters, 153:75-78 (2000) 4 pages.
Application No. PCT/US2010/038700, Supplemental European Search Report dated Apr. 20, 2015. 7 pages.
Surks, Martin I. et al. "Subclinical Thyroid Disease; Scientific Review and Guidelines for Diagnosis and Management." Journal of the American Medical Association, Jan. 14, 2004, vol. 291, No. 2, pp. 228-238; especially p. 230-231.
J Wood, K Bonjean, S Ruetz, A Bellahcene, L Devy, JM Foidart, V Castronovo, JR Green. "Novel Antiangiogenic Effects of the u Bisphosphonate Compound Zoledronic Acid." The Journal of Pharmacology and Experimental Therapeutics, vol. 302, No. 3, 2002, pp. 1 055-1 061.
M Valcin, DJ Bharali, L Lansing, E Dyskin, SS Mousa, A Hercbergs, FB Davis, PJ Davis, SA Mousa. "Tetraidothyroacetic Acid v (Tetrac) and Tetrac Nanoparticles Inhibit Growth of Human Renal Cell Carcinoma Xenografts." Anticancer Research, vol. 29, 2009, pp. 3825-3832.
Office Action (Mail Date Jun. 21, 2011) for U.S. Appl. No. 12/947,389, filed Nov. 16, 2010.
Office Action (Mail Date Apr. 4, 2012) for U.S. Appl. No. 12/947,389, filed Nov. 16, 2010.
Office Action (Mail Date Oct. 17, 2012) for U.S. Appl. No. 12/947,389, filed Nov. 16, 2010.
Office Action (Mail Date Apr. 4, 2014) for U.S. Appl. No. 12/947,389, filed Nov. 16, 2010.
Notice of Allowance (Mail Date May 12, 2015) for U.S. Appl. No. 12/816,287.
Office Action (Mail Date May 12, 2015) for U.S. Appl. No. 14/078,713, filed Nov. 13, 2013.
Office Action (Mail Date Mar. 24, 2015) for U.S. Appl. No. 13/975,725, filed Aug. 26, 2013.
Office Action (Mail Date Oct. 5, 2012) for U.S. Appl. No. 12/644,493, filed Dec. 22, 2009.
Office Action (Mail Date Apr. 16, 2015) for U.S. Appl. No. 13/156,047, filed Jun. 8, 2011.
Office Action (Mail Date Oct. 14, 2014) for U.S. Appl. No. 14/242,041, filed Apr. 1, 2014.
Blaszczyk-Thurin et al., "An Experimental Vaccine Expressing Wild-Type p53 induces Protective Immunity Against Glioblastoma Cells with High Levels of Endogenous p53", Scand. J. Immunol., 56:361-375 (2002) 15 pages.

\* cited by examiner

* Syringe A: Injecting Anti-cancer Drugs
* Syringe B: Harvesting media for LC-MS-MS Examination Figure Not Drawn to Scale

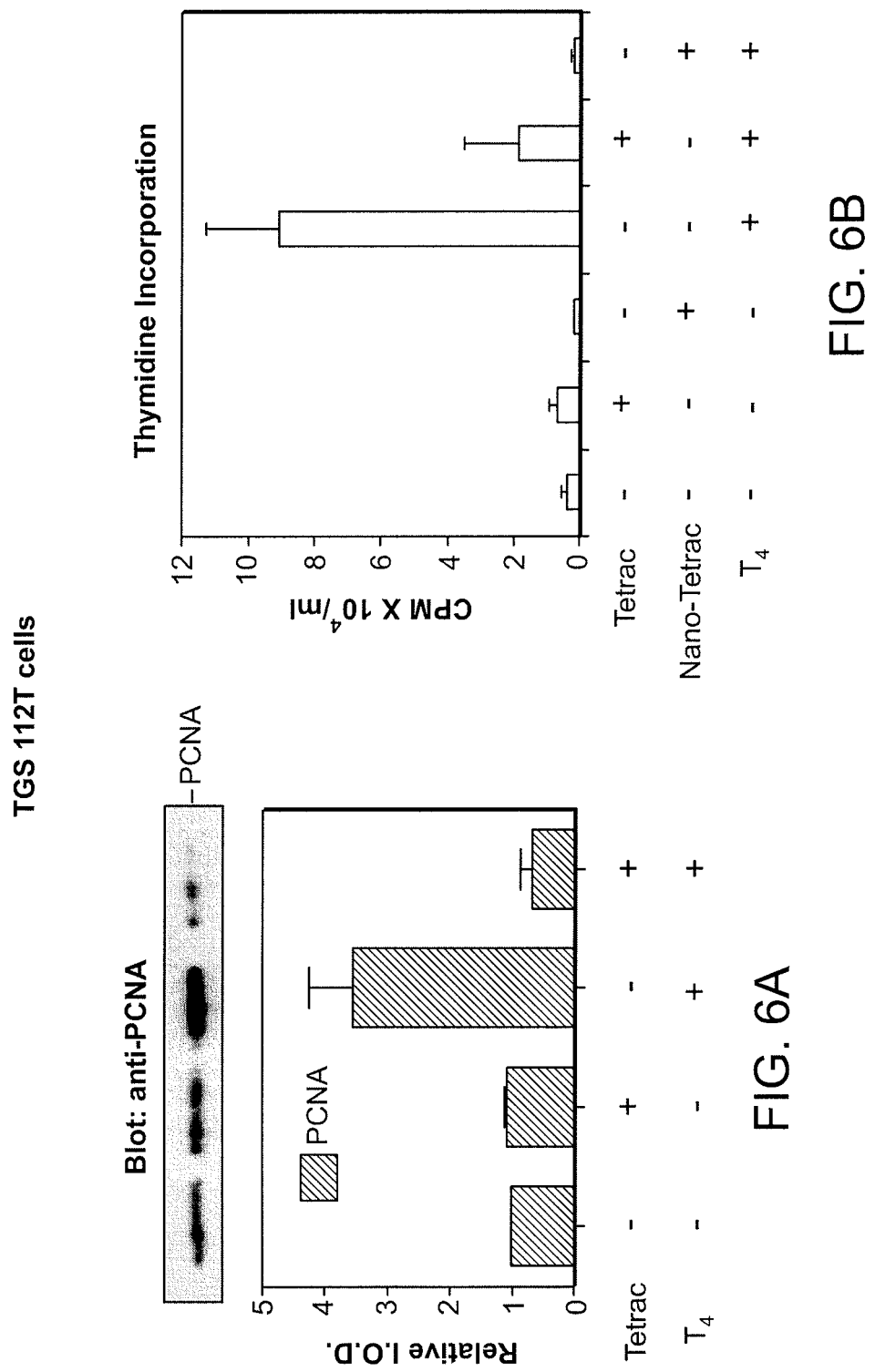

Cells were treated with constant concentrations of drugs. Cetuximab alone did not show a large effect. Between days 12 and 18 the $10^{-6}$ M NP-Tetrac + 0.1 μg.mL cetuximab appeared to have a larger effect on cell counts than $10^{-6}$ M NP-Tetrac + 1.0 μg/mL cetuximab.

Cells were treated with constant concentrations of drugs. Cetuximab alone did not show a large effect. Between days 10 and 20 the $10^{-6}$ M NP-Tetrac + 0.1 μg.mL cetuximab appeared to have a similar effect on cell counts as $10^{-6}$ M NP-Tetrac + 1.0 μg/mL cetuximab.

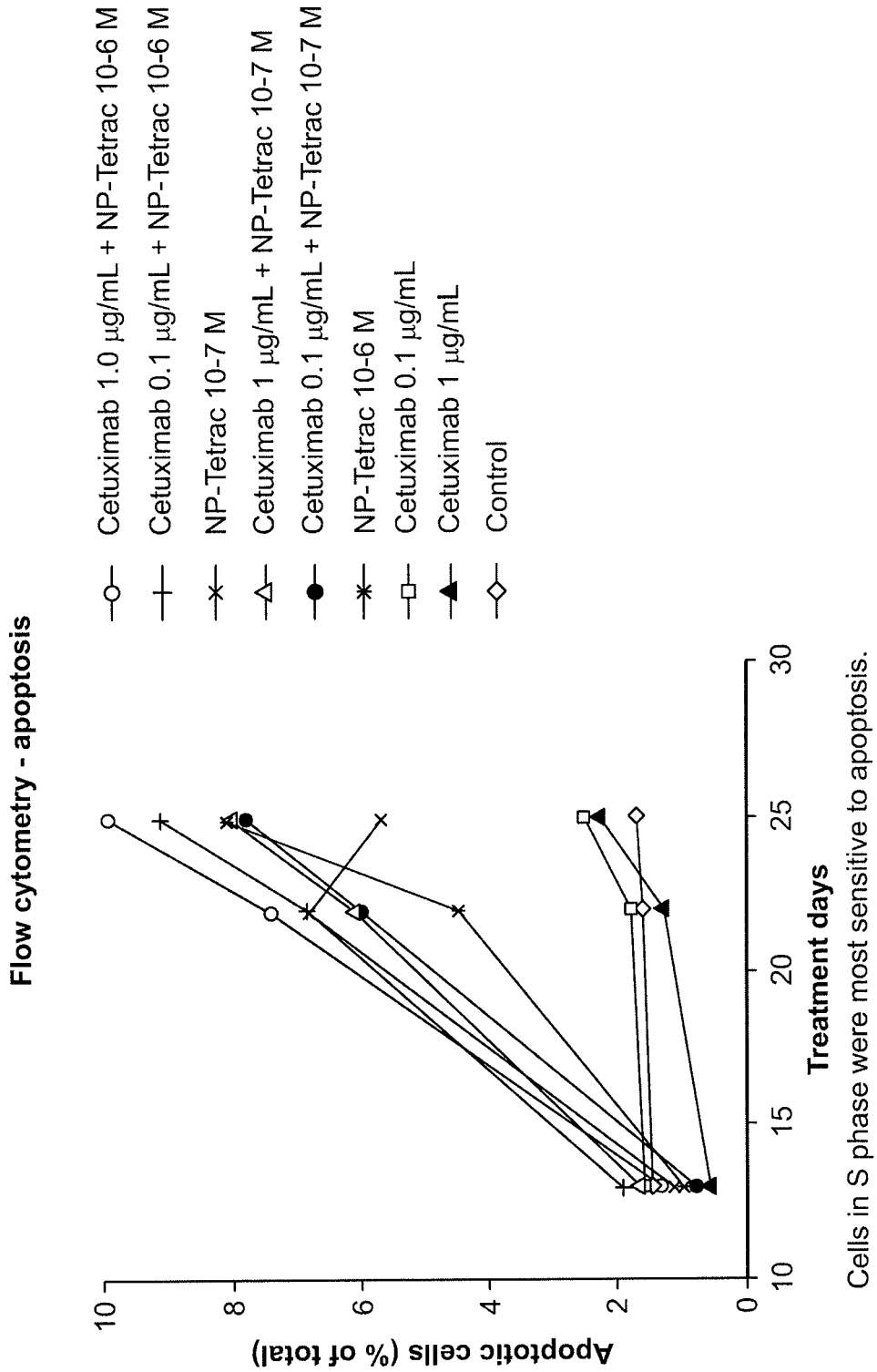

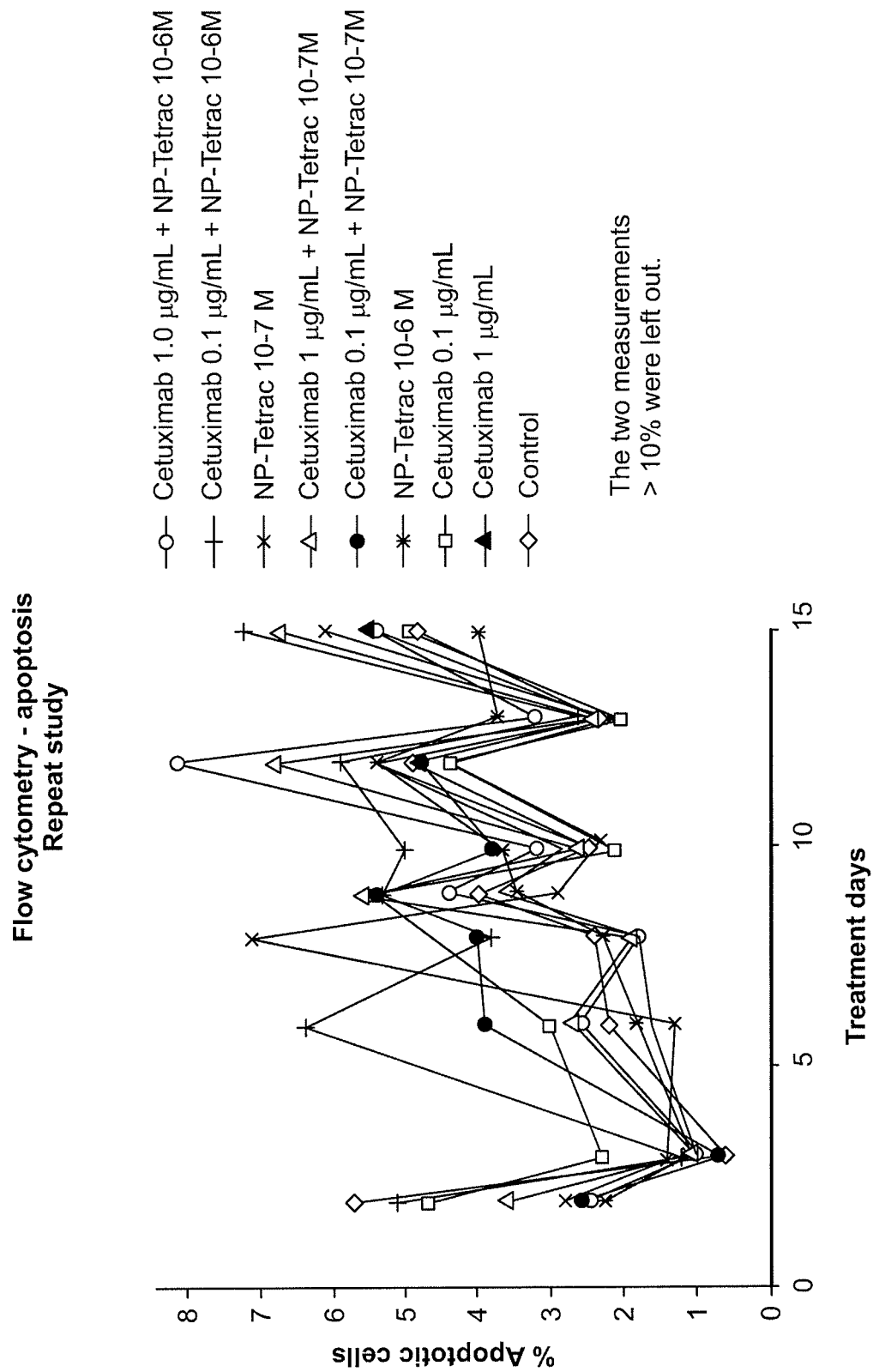

COMBINATION TREATMENT OF CANCER WITH CETUXIMAB AND TETRAC

RELATED APPLICATIONS

This application claims priority to U.S. Ser. No. 61/165,119, filed Mar. 31, 2009, which is herein incorporated by reference in its entirety.

FIELD OF THE INVENTION

The invention described herein pertains to tetraiodothyroacetic acid-like compounds and other compounds that inhibit the expression of hypoxia-inducible factor 1-α (HIF1α) gene as well as various formulations thereof and methods for the prevention or treatment of cancer.

REFERENCE TO A "SEQUENCE LISTING"

The sequence listing material in the text file entitled "12751375_SeqList_ST25.txt" (2,438 bytes), which was created on May 14, 2010, is herein incorporated by reference in its entirety.

BACKGROUND

Thyroid hormones, such as L-thyroxine (T4) and 3,5,3'-triiodo-L-thyronine (T3), and their analogs such as GC-1, DITPA, Tetrac and Triac, regulate many different physiological processes in different tissues in vertebrates. It was previously known that many of the actions of thyroid hormones are mediated by the thyroid hormone receptor ("TR"). However, a novel cell surface receptor for thyroid hormone (L-thyroxine, T4; T3) has been described on integrin αvβ3. This receptor is at or near the Arg-Gly-Asp (RGD) recognition site on the integrin. The αvβ3 receptor is not a homologue of the nuclear thyroid hormone receptor (TR), but activation of this cell surface receptor results in a number of nucleus-mediated events, including the recently-reported pro-angiogenic action of the hormone and fibroblast migration in vitro in the human dermal fibroblast monolayer model of wound-healing.

Evidence that thyroid hormone can act primarily outside the cell nucleus has come from studies of mitochondrial responses to T3 and diiodothyronine (T2), from rapid onset effects of the hormone at the cell membrane, and from actions on cytoplasmic proteins. The recent description of a plasma membrane receptor for thyroid hormone on integrin αvβ3 has provided some insight into effects of the hormone on membrane ion pumps, such as the Na+/H+ antiporter, and has led to the description of interfaces between actions initiated at the membrane thyroid hormone receptor and nuclear events that underlie important cellular or tissue processes, such as, for example, angiogenesis and proliferation of certain tumor cells.

Integrin αvβ3 binds thyroid hormone near the Arg-Gly-Asp (RGD) recognition site of the integrin protein. The RGD site is involved in the protein-protein interactions linking the integrin to extracellular matrix (ECM) proteins such as vitronectin, fibronectin and laminin. (See Plow et al., 2000. *J. Biol. Chem.* 275:21785-88). Also initiated at the cell surface integrin receptor is the complex process of angiogenesis, which can be monitored in either a standard chick blood vessel assay or with human endothelial cells in a sprouting assay. This hormone-dependent process requires mitogen-activated protein kinase (MAPK; extracellular regulated kinase [ERK] 1/2) activation and the elaboration of vascular growth factors, including, but not limited to basic fibroblast growth factor (bFGF; FGF2), which is the downstream mediator of thyroid hormone's effect on angiogenesis. Tetrac blocks this action of T4 and T3, as does RGD peptide and other small molecules (such as XT-199) that mimic RGD peptide(s). Thus, it is possible that desirable neovascularization can be promoted with local application of thyroid hormone analogs, for example, in wound-healing, or that undesirable angiogenesis, such as that which supports tumor growth, can be antagonized with tetrac or triac.

SUMMARY OF THE INVENTION

The invention provided pharmaceutical compositions for treating cancer involving a combination of cetuximab and tetrac, where the combination induces apoptosis in cancer cells. In some embodiments, the tetrac can be used in a nanoparticulate form. When in nanoparticulate form, the nanoparticulates may also target additional chemotherapeutic agents to the cancer cells. Additionally, in various embodiments, the composition also contains an anti-estrogen compound. Moreover, the combination of cetuximab and tetrac can be used to inhibit phosphatidylinositol 3-kinase (PI3K)-dependent hypoxia-inducible factor 1-α (HIF1α) gene expression.

More specifically, provided herein are pharmaceutical compositions for treating cancer that contain a combination of cetuximab and an anti-angiogenic thyroid hormone analog, wherein the combination inhibits expression of HIF1α gene in cancer cells. Those skilled in the art will recognize that the HIF1α gene product is a survival factor in cancer cells. For example, the cancer cells may be selected from breast cancer, lung cancer, kidney cancer, thyroid cancer, brain cancer (glioma), ovarian cancer, pancreatic cancer, prostate cancer, plasma cell cancer (myeloma), squamous cell head-and-neck cancer, liver cancer, muscle cancer (sarcoma), colon cancer, neuroblastoma, lymphoma, stomach cancer, adenoid cystic carcinoma, and skin cancer including melanoma, basal cell carcinoma, and squamous cell carcinoma.

In various embodiments described herein, thyroid hormone analog is tetrac or triac (triiodothyroacetic acid). By way of non-limiting example, one preferred thyroid hormone analog that is used in the compositions of the invention is tetrac.

In any of the pharmaceutical compositions described herein, the thyroid hormone analog (such as tetrac) can be conjugated via a covalent bond to a polymer selected from polyvinyl alcohol, acrylic acid ethylene co-polymer, methoxypolyethylene, polyethyleneglycol (PEG), polyacrylic acid, polylactic acid, agarose, polyglycolide, polylactide, PEO, m-PEG, PVA, PLLA, PGA, poly-L-lysine, Human Serum Albumin, cellulose derivatives, carbomethoxy/ethyl/hydroxypropyl, hyaluronic acid, folate linked cyclodextrin/dextran, sarcosine/amino acid spaced polymer, alginate, carrageenan, pectin/chitosan, chitosan, dextran, collagen, polyamine, poly aniline, poly alanine, polytrytophan, poly tyrosine, polylactide-co-glycolide (PLG), poly(lactic-co-glycolic acid) (PLGA), polylysyl glycolide, polyglycolide, polylactic acid, or co-polymers thereof, wherein the polymer is formulated into a nanoparticle, wherein the nanoparticle is between 150 and 250 nanometers in size, and wherein the tetrac binds to the cell surface receptor for thyroid hormone on integrin αvβ3.

In some embodiments, a linker between about 4 and 15 (i.e., 4, 5, 6, 7, 8, 9, 10, 11, 12, 13, 14, or 15) atoms long is used between the polymer (or the synthesized nanoparticle) and the thyroid hormone or thyroid hormone analog. For example, the linker may be attached to the thyroid hormone or thyroid hormone analog via a covalent or non-covalent bond.

Moreover, the point of attachment for the linker may be the outer ring hydroxyl of the thyroid hormone or thyroid hormone analog. Those skilled in the art will recognize that, because tetrac and triac do not have an amino group on their outer rings (in contrast to T4 and T3), the use of a linker is necessary in order to insure that conjugation to the nanoparticle occurs via the outer ring of the thyroid hormone analog. When a linker is used, the amide bond for the linker must be imbedded in the nanoparticle to prevent lysis of that bond by circulating peptidases.

The pharmaceutical compositions may also contain one or more anti-estrogen compounds (e.g., tamoxifen and/or aromatase inhibitors).

Alternatively (or additionally), the nanoparticles may also contain one or more additional chemotherapeutic agents. In such embodiments, the one or more additional chemotherapeutic agents are targeted to the cancer cells.

Those skilled in the art will recognize that the combination of cetuximab and an anti-angiogenic thyroid hormone analog inhibits PI3K-dependent HIF1α gene expression in cancer cells.

Also provided herein are methods of treating cancer comprising administering a therapeutically effective amount of a combination of cetuximab and an anti-angiogenic thyroid hormone analog to a patient suffering therefrom. In various embodiments, the thyroid hormone analog is tetrac or triac. In one preferred embodiment, the thyroid hormone analog is tetrac.

In any of the methods disclosed herein, tetrac can be conjugated via a covalent bond to a polymer selected from polyvinyl alcohol, acrylic acid ethylene co-polymer, methoxypolyethylene, polyethyleneglycol (PEG), polyacrylic acid, polylactic acid, agarose, polyglycolide, polylactide, PEO, m-PEG, PVA, PLLA, PGA, poly-L-lysine, Human Serum Albumin, cellulose derivatives, carbomethoxy/ethyl/hydroxypropyl, hyaluronic acid, folate linked cyclodextrin/dextran, sarcosine/amino acid spaced polymer, alginate, carrageenan, pectin/chitosan, chitosan, dextran, collagen, polyamine, poly aniline, poly alanine, polytrytophan, poly tyrosine, polylactide-co-glycolide (PLG), poly(lactic-co-glycolic acid) (PLGA), polylysyl glycolide, polyglycolide, polylactic acid, or co-polymers thereof, wherein said polymer is formulated into a nanoparticle, wherein said nanoparticle is between 150 and 250 nanometers in size, and wherein said tetrac binds to the cell surface receptor for thyroid hormone on integrin αvβ3.

Additionally, the methods of the invention may also involve administering one or more anti-estrogen compounds to the subject. By way of non-limiting example, the anti-estrogen compounds are tamoxifen and/or aromatase inhibitors.

Moreover, the nanoparticles used in the methods of the invention may also contain one or more additional chemotherapeutic agents.

Those skilled in the art will recognize that in some embodiments, any of the pharmaceutical compositions and/or methods described herein, cetuximab can be encapsulated within nanoparticle that is linked to the thyroid hormone analog.

BRIEF DESCRIPTION OF THE DRAWINGS

FIG. 3 is a series of graphs showing that tetrac induces anti-proliferation in cancer cells.

FIG. 4 is a series of graphs showing the time course distribution of $[^{125}I]$-tetrac in human glioblastoma U87MG cells.

FIG. 5 is a series of graphs showing that tetrac and nano-tetrac induce antiproliferation.

FIG. 6 is a series of graphs showing the effects of tetrac and nano-tetrac in human adenoid cystic carcinoma (TGS112T). In FIG. 6A, TGS112T cancer cells were treated with $10^{-7}$M $T_4$ in the presence or absence of $10^{-7}$M tetrac for 24 h. $T_4$-induced PCNA expression was inhibited by tetrac. In FIG. 6B, TGS112T cancer cells were treated with $10^{-7}$ M $T_4$ in the presence or absence of $10^{-7}$ M tetrac or nano-tetrac, daily and 1 μCi [$^3$H]-thymidine (final concentration, 13 nM) was added for 24 h. $T_4$ increased thymidine incorporation which was inhibited by tetrac and nano-tetrac. Tetrac itself increased thymidine incorporation slightly.

FIGS. 15A-C are graphs showing the results of flow cytometry experiments for apoptosis.

DETAILED DESCRIPTION

Figure 1:
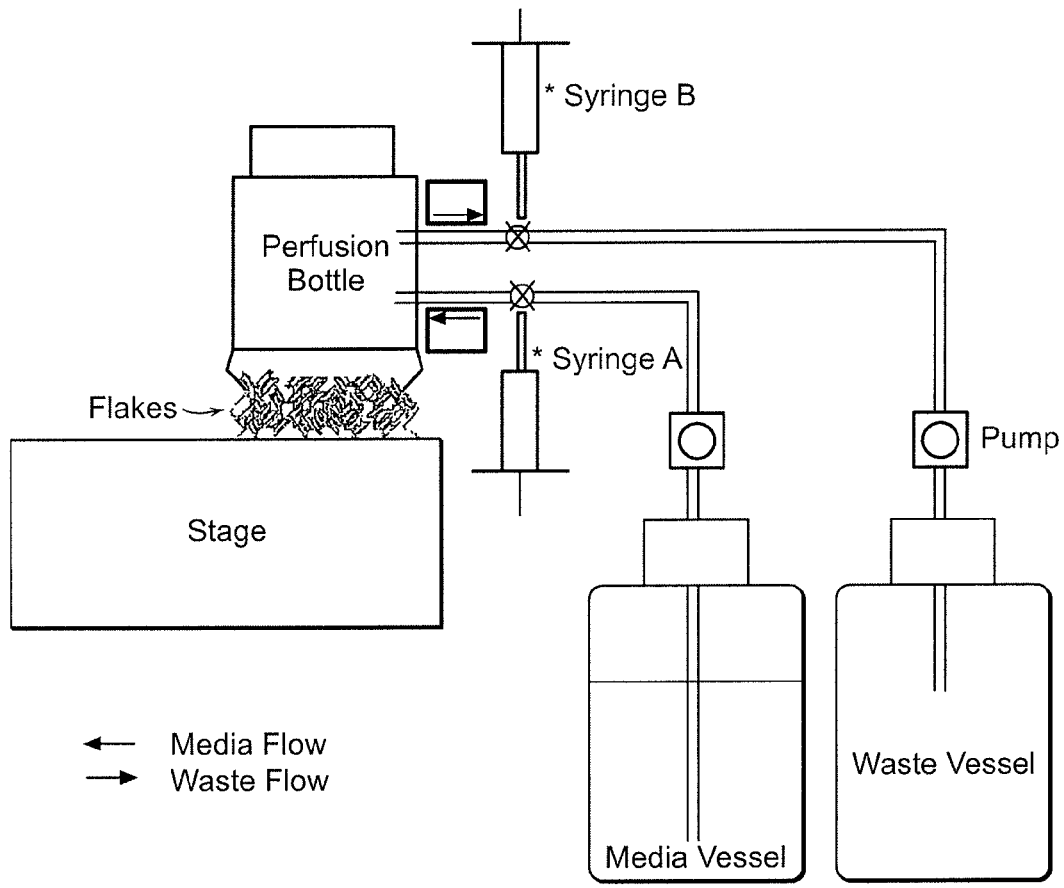
FIG. 1 is a diagram of the perfusion bellows pharmacodynamic culture system. Cells of cancer lines of interest are grown on plastic flakes suspended in a flow-through, bellows-agitated system that allows for homogeneous exposure of cells to drug/drug metabolite solutions and frequent sampling of cells for viability. Direction of arrow indicates the flow of influx/efflux medium.

The details of one or more embodiments of the invention have been set forth in the accompanying description below. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural references unless the context clearly dictates otherwise. All patents and publications cited in this specification are incorporated by reference in their entirety.

For convenience, certain terms used in the specification, examples and claims are collected here. Unless otherwise defined, all technical and scientific terms used herein have the same meaning as commonly understood by one of ordinary skill in the art to which this invention pertains.

The term "agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues. The activity of such agents may render it suitable as a "therapeutic agent" which is a biologically, physiologically, or pharmacologically active substance (or substances) that acts locally or systemically in a subject.

As used herein, the terms "angiogenesis agent" or "angiogenic agent" include any compound or substance that promotes or encourages angiogenesis, whether alone or in combination with another substance. Examples include, but are not limited to, T3, T4, T3 or T4-agarose, polymeric analogs of T3, T4, 3,5-dimethyl-4-(4'-hydroxy-3'-isopropylbenzyl)-phenoxy acetic acid (GC-1), or DITPA. In contrast, the terms "anti-angiogenesis agent" or "anti-angiogenic agent", as used herein, refer to any compound or substance that inhibits or discourages angiogenesis, whether alone or in combination with another substance. Examples include, but are not limited to, tetrac, triac, XT 199, and mAb LM609. The structures of representative angiogenic and anti-angiogenic agents are provided herein:

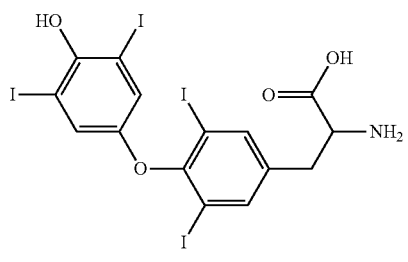

T4

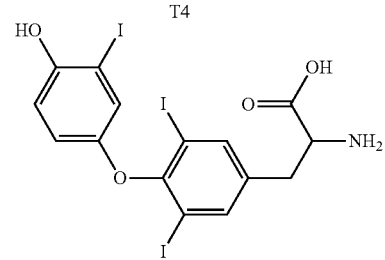

T3

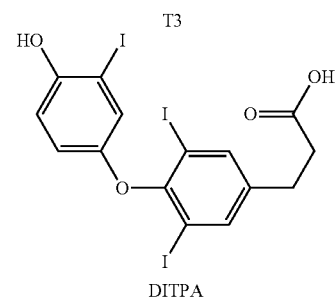

DITPA

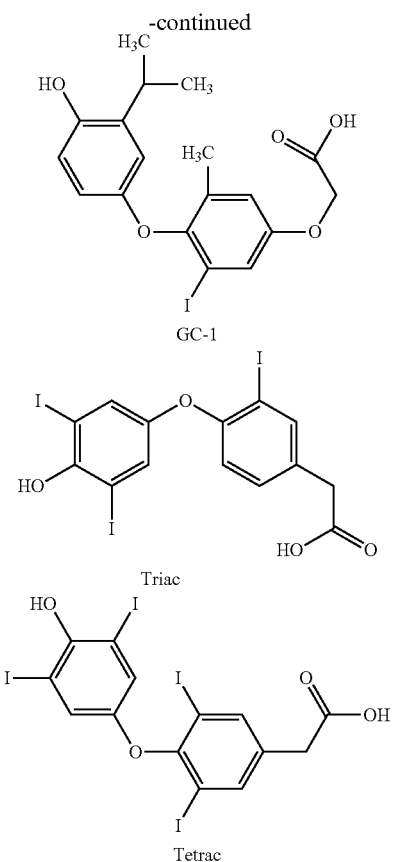

GC-1

Triac

Tetrac

The term "RGD", as used herein, refers to the single letter amino acid code and references the tripeptide amino acid sequence arginine-glycine-aspartic acid (Arg-Gly-Asp).

A "small molecule" or "small molecule chemical compound" as used herein, is meant to refer to a composition that has a molecular weight of less than 2000 Daltons, preferably less than 1000 Daltons, more preferably less than 750 Daltons, most preferably less than 500 Daltons. Small molecules are organic or inorganic and are distinguished from polynucleotides, polypeptides, carbohydrates and lipids.

The terms "peptide mimetic", "mimetic", or "peptidomimetic" as used herein refer to an agent or a compound that mimics at least one activity of a peptide or compound or a peptide analog in which one or more peptide bonds have been replaced with an alternative type of covalent bond that is not susceptible to cleavage by peptidases.

When referring to a compound, a "form that is naturally occurring" means a compound that is in a form, e.g., a composition, in which it can be found naturally. A compound is "not in a form that is naturally occurring" if, for example, the compound has been purified and separated from at least some of the other molecules that are typically found with the compound in nature. Thus, a "naturally occurring compound" refers to a compound that can be found in nature, i.e. a compound that has not been designed by man. A naturally occurring compound may be harvested from nature or refined from a complex mixture of naturally occurring products or it may be reproduced synthetically.

A "patient," "individual," "subject" or "host" refers to either a human or a non-human animal.

The term "modulation" is art-recognized and refers to up regulation (i.e., activation or stimulation), down regulation (i.e., inhibition or suppression) of a response, or any combination thereof.

The terms "prophylactic" or "therapeutic" treatment are art-recognized and refer to the administration of one or more drugs or compounds to a host. If administration occurs prior to clinical manifestation of the unwanted condition (e.g., disease or other unwanted state of the host animal), the treatment is prophylactic, i.e., it protects the host against developing the unwanted condition. If administration occurs after the manifestation of the unwanted condition, the treatment is therapeutic, i.e., it is intended to diminish, ameliorate or maintain the existing unwanted condition or other side effects.

The term "mammal" is known in the art and includes humans, primates, bovines, porcines, canines, felines, and rodents (e.g., mice and/or rats).

As used herein, the term "pharmaceutically-acceptable salt" is art-recognized and refers to the relatively non-toxic, inorganic and organic acid addition salts of compounds, including, for example, those contained in the compositions described herein.

The term "pharmaceutically acceptable carrier" is art-recognized and refers to a pharmaceutically-acceptable material, composition or vehicle, such as, for example, a liquid or solid filler, diluent, excipient, solvent or encapsulating material, involved in carrying or transporting any subject composition or component thereof from one organ or portion of the body, to another organ or portion of the body. Each carrier must be "acceptable" in the sense of being compatible with the subject composition and its components and not injurious to the patient. Some non-limiting examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The terms "systemic administration," "administered systemically," "peripheral administration" and/or "administered peripherally", as used herein, are all art-recognized and refer to the administration of a subject composition, therapeutic or other material other than directly into the central nervous system, such that it enters the patient's system and, thus, is subject to metabolism and other like processes.

Likewise, the terms "parenteral administration" and "administered parenterally" are also art-recognized and refer to modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, and/or intrasternal injection and infusion.

As used herein, "treating" a condition or disease refers to curing as well as ameliorating at least one symptom of the condition or disease.

The term "therapeutic agent" is art-recognized and refers to any chemical moiety that is a biologically, physiologically, or pharmacologically active substance that acts locally or systemically in a subject. This term also refers to any substance intended for use in the diagnosis, cure, mitigation, treatment or prevention of disease or in the enhancement of desirable physical or mental development and/or conditions in an animal or human.

Moreover, the term "therapeutic effect" is art-recognized and refers to a local or systemic effect in animals, particularly mammals, and more particularly humans, caused by a pharmacologically active substance. The phrase "therapeutically-effective amount" means that amount of such a substance that produces some desired local or systemic effect at a reasonable benefit/risk ratio and is applicable to any treatment. The therapeutically effective amount of such substance will vary depending upon the subject and disease or condition being treated, the weight and age of the subject, the severity of the disease or condition, the manner of administration and the like, which can readily be determined by one of ordinary skill in the art. For example, certain compositions described herein may be administered in a sufficient amount to produce a desired effect at a reasonable benefit/risk ratio applicable to such treatment.

The term "synthetic" is art-recognized and refers to production by in vitro chemical or enzymatic synthesis.

Throughout this application, the terms "nanoparticle", "nanoparticulate" and "nanoparticulate form" are used interchangeably to refer to a modification of any of the active compound(s) of the invention (i.e., cetuximab and/or the anti-angiogenic thyroid hormone analogs (i.e., tetrac and/or triac)), where the active compound(s) are covalently bound (e.g., by an ester, ether, or sulfur linkage) to a polymer wherein the polymer is formulated into a nanoparticle, wherein the active compound is located on the surface of the nanoparticle and wherein the nanoparticle is between 150 and 250 nm in size. Conjugation of the anti-angiogenic thyroid hormone analogs via covalent bond to a polymer increases the half life of the compound and/or insures that the compound does not gain access to the interior of the cells (thus, limiting their action to the integrin binding site). The preparation and use of nanoparticulate forms of the anti-angiogenic thyroid hormone analogs are described in the art (see, e.g., WO2008/140507, which is herein incorporated by reference in its entirety). As used herein, the terms "nano-tetrac", "nano tetrac", "nanoparticulate tetrac", "NP-tetrac", and "NP-T" are used interchangeably to refer to a nanoparticulate form of the thyroid hormone analog tetrac.

Those skilled in the art will recognize that, in some embodiments, cetuximab can be encapsulated within the nanoparticulate form of tetrac.

Cetuximab (marketed in North America by ImClone and Bristol-Myers Squibb and in the rest of the world by Merck KGaA) under the name Erbitux), is a chimeric (mouse/human) monoclonal antibody that blocks activation of the epidermal growth factor (EGF) receptor (EGFR). Currently, cetuximab is given by intravenous infusion for treatment of metastatic colorectal cancer and head and neck cancers. Specifically, cetuximab is indicated for the treatment of patients with epidermal growth factor receptor (EGFR)-expressing, KRAS wild-type metastatic colorectal cancer (mCRC), in combination with chemotherapy, and as a single agent in patients who have failed oxaliplatin- and irinotecan-based therapy and who are intolerant to irinotecan. In addition, cetuximab (Erbitux) is also indicated for the treatment of patients with squamous cell cancer of the head and neck in combination with platinum-based chemotherapy for the first line treatment of recurrent and/or metastatic disease and in combination with radiation therapy for locally advanced disease. Cetuximab and other EGFR inhibitors only work on tumors that are not mutated.

A diagnostic immunohistochemistry assay (EGFR pharmDx) can be used to detect EGFR expression in the tumor material. Approximately 75% of patients with metastatic colorectal cancer have an EGFR-expressing tumor and are therefore considered eligible for treatment with cetuximab. In mCRC, biomarkers, including KRAS (a small G protein on the EGFR pathway), are indicative of a patient's response to cetuximab (Erbitux). Data have shown that sixty percent of patients who express the KRAS wild-type tumor are significantly more likely to benefit from treatment with cetuximab or a combination of cetuximab plus chemotherapy. Assessment for EGFR expression is required for the use of cetuximab (Erbitux) in Colorectal Cancer, but not in Head & Neck Cancer. Cetuximab and other EGFR inhibitors only work on tumors that are not mutated.

Two recent studies demonstrated that patients with KRAS wild-type tumors demonstrated significantly increased response rates and disease free survival when treated with cetuximab and standard chemotherapy, as compared to patients receiving chemotherapy alone. (See Bokemeyer et al., 2009. J. Clin. Oncol. 27(5):663-71; Van Cutsem et al., 2009 N. Engl. J. Med. 360(14):1408-17).

Cetuximab was approved by the FDA in March 2006 for use in combination with radiation therapy for treating squamous cell carcinoma of the head and neck (SCCHN) or as a single agent in patients who have had prior platinum-based therapy. Two landmark studies have evaluated the benefits of cetuximab (Erbitux) in patients with SCCHN in both the locally advanced (Bonner trial) and the recurrent and/or metastatic (EXTREME trial) settings. The EXTREME trial marks the first time in 30 years that a Phase III trial has demonstrated a survival benefit in 1st-line recurrent and/or metastatic disease.

Associated with, or independently of, its action on EGFR, cetuximab is known to inhibit the expression of the HIF1α gene. The gene product of the HIF1α gene is a survival factor in cancer cells. This gene product stimulates tumor cell proliferation, is pro-angiogenic, and supports the process of metastasis. Moreover, it has been shown that cetuximab decreases HIF1α gene expression by a phosphatidinositol 3-kinase (PI3K)-requiring process. (See Li et al., 2008. Mol. Cancer Ther 7:1207-17 (incorporated by reference in its entirety).

The epidermal growth factor receptor (EGFR) family members seem to play a critical role in tumourigenesis. The monoclonal anti-EGFR antibody cetuximab, and possibly other anticancer monoclonal antibodies now used in the clinic, may promote trogocytic removal of the therapeutic monoclonal antibodies and their cognate antigens from tumor cells in vivo. (See, Lin et al., 2008. J. Cell. Biochem. 104: 2131-42; Beum et al., 2008. J Immunol. 181:8120-32). Cetuximab, either as a single agent or in combination with chemotherapy, has demonstrated clinical activity, however, it appears to benefit only select patients. (See Patel et al., Pharmacotherapy. 2008 28):31S-41S). Studies indicate that cetuximab does not enhance any inhibitory effect of anti-HER2 antibodies, such as trastuzumab or pertuzumab, in ER-positive breast cancer, BT474 and ER-negative SK-BR-3 cells, most probably due to the dominant overexpression of HER2. (See Jol et al., 2009. N Engl J Med 360:563-72; Patel, 2008. Pharmacotherapy 28:31 S-41S; Brockoff et al., 2007. Cell Prolif. 40:488-507, each of which is incorporated herein by reference in its entirety).

Integrin αvβ3 has been shown to be expressed on tumor cells, on endothelial and vascular smooth muscle cells, on osteoclasts, and on angiogenically active blood vessel cells. (See Davis et al., 2008. Front Neuroendocrinol 29:211-18; Davis et al., 2009. Am J Physiol Endocrinol Metab 297: E1238-E1246). This limited expression makes this integrin an attractive target for the development of cancer treatment strategies because nano-tetrac has little effect on proliferation of non-malignant cells. The observed additive effects of combinations of nano-tetrac and other chemotherapeutic agents observed here suggests that lower dosages of agents are possible with conjoint therapy.

Combination of modified or unmodified cetuximab and modified or unmodified tetrac (i.e., tetrac or nano-tetrac) in a vehicle, for example, a single nanoparticle, can also be used together with one or more additional conventional cancer chemotherapeutic agents as a delivery system to target cancer cells for the additional chemotherapeutic agents. That is, tetrac is recognized and liganded by integrin αvβ3-bearing tumor cells, and this fact can be used to bring the tumor cells into contact with the additional chemotherapeutic agents. Thus, in this model, three (or more) anti-cancer agents are transported directly to the cancer cell.

Accordingly, those skilled in the art will recognize that cetuximab, whether unmodified or as nanoparticulates, in conjunction with tetrac or triac, whether unmodified or as nanoparticulates, in combination with one or more conventional chemotherapeutic agents can be fabricated and used.

Tetraiodothyroacetic acid (tetrac) is a deaminated thyroid hormone analogue that binds to the integrin αvβ3 receptor for the hormone. (See Bergh et al., 2005. Endocrinology 146: 2864-71; Davis et al., 2006. Cancer Res. 66:7270-75). Tetraiodothyroacetic acid (tetrac) is a thyroid hormone derivative with anti-proliferative activity in cancer cells that are initiated at a cell surface receptor for thyroid hormone on integrin αvβ3. (See Davis et al., 2009. Am J Physiol 297: E1238-E1246; Lin et al., 2009. Am J Physiol 296:C980-C991; Yalcin et al., 2009. Anticancer Res 10:3825-3831; and Glinskii et al., 2009. Cell Cycle 8:3554-3562). Tetrac is pro-apoptotic (see A B Glinskii et al., ibid.). Tetrac is also a polyfunctional anti-angiogenic agent. Tetrac is an antagonist at the receptor, inhibiting binding of agonist L-thyroxine ($T_4$), and 3,5,3'-triiodo-L-thyronine ($T_3$) to the integrin of cultured cells (see Berg et al. 2005. 146:2864-71) and blocking nongenomically initiated effects of $T_4$ and $T_3$ on signal transduction pathways (see Davis et al., 2006. Cancer Res. 7270-75; Lin et al., 2007. Steroids 72:180-87; and Lin et al., 2008. Carcinogenesis 29:62-69).

Inhibition of the angiogenic action of thyroid hormone by tetrac has been shown in the chick chorioallantoic membrane (CAM) model and in the vessel sprouting model involving human dermal microvascular endothelial cells (HDMEC). Tetrac is effective in the CAM and HDMEC models. This inhibitory action of tetrac is thought to reflect its influence at the RGD recognition site on the integrin, which is relevant to cell surface pro-angiogenic growth factor receptors with which the integrin engages in cross talk and whose activities may be modulated by the integrin.

Tetrac also decreases basic fibroblast growth factor (bFGF) and vascular growth factor (VEGF)-induced angiogenesis in the absence of agonist thyroid hormone analogues (see Davis et al., 2004. Circ Res. 94:1500-1506; and Mousa et al., 2008. Angiogenesis 11:183-90), thereby supporting cross talk between the integrin and the clustered receptors for VEGF, bFGF, and other pro-angiogenic peptides. Tetrac inhibits thyroid hormone-induced activation of mitogen-activated protein kinase (MAPK, ERK1/2) and cell proliferation in a variety of cancer cell lines (see Davis et al., 2006. Cancer Res. 7270-75; Lin et al., 2007. Steroids 72:180-87; and Lin et al., 2008. Carcinogenesis 29:62-69) and also induces the production of a pro-apoptotic protein, BcL-x short form, in human bronchial adenocarcinoma cells (see Tzirogiannis et al., 2007. Abstract #P1-602 in $89^{th}$ Annual Meeting, The Endocrine Society), rodent glioma C6 cells (see Lin et al., 2008. Carcinogenesis 29:62-69) and human follicular thyroid cancer cells (see Yalcin et al., 2010. Thyroid 20:281-86). These latter studies suggest that tetrac treatment supports apoptosis in cancer cells, as do RNA microarray observations. (See Glinskii et al., 2009. Cell Cycle 8(21):3544-62; 2009; J Clin Endocrinol Metab, February 2010, Epub only).

In addition to the ability of tetrac to block angiogenesis induced by VEGF and bFGF, tetrac has also been shown to enhance the response in vitro to either doxorubicin, etoposide, cisplatin, or trichostatin A of chemotherapy-resistant human tumor cell lines derived from neuroblastoma (SKN-SH/R), osteosarcoma (SaOS2/R), and breast carcinoma (MCF-7/R) cells. (See Rebbaa et al., 2008. Angiogenesis 11:269-76).

Figure 10:
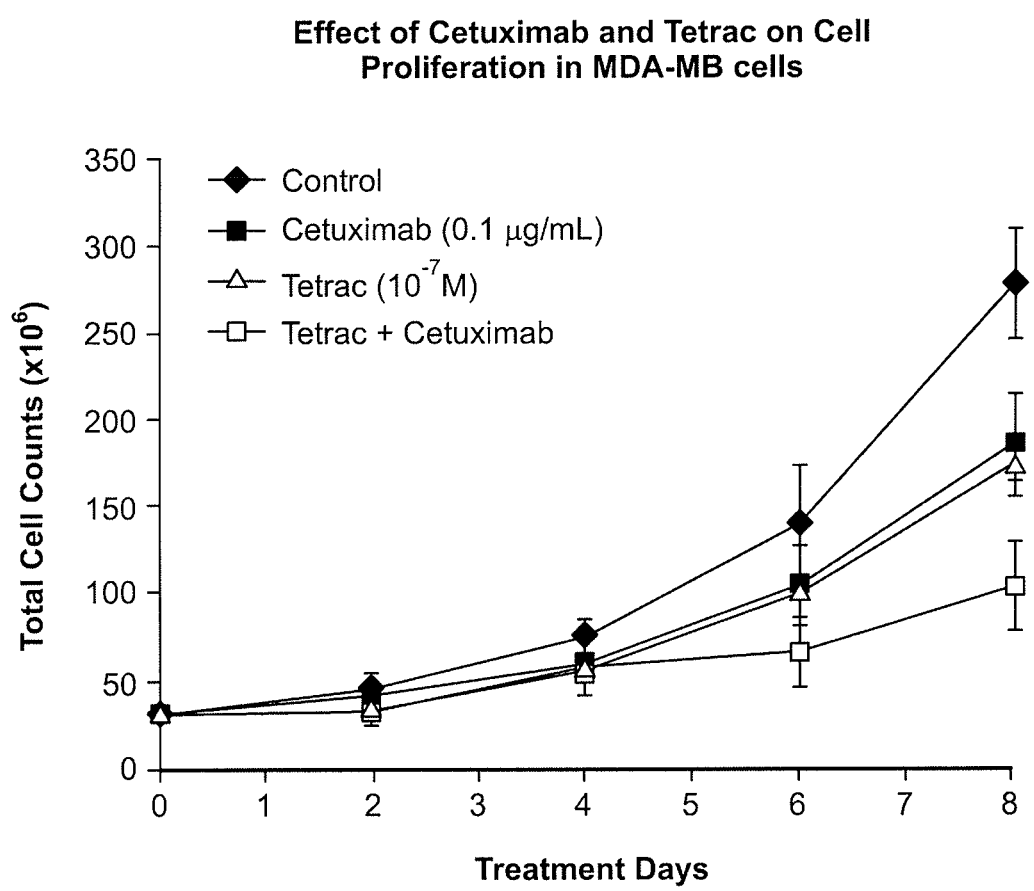
FIG. 10 is a graph showing the effect of tetrac and cetuximab-induced anti-proliferation. Human breast cancer MDA-MB cells were treated daily with 0.1 µg/ml of cetuximab, tetrac ($10^{-7}$ M), or the combination in the bellows perfusion culture system. Cells were harvested at the time points indicated. Cetuximab, tetrac, or combination-induced anti-proliferation was determined by cell number count.

Because tetrac is known to have thyromimetic activity within cells (see Lameloise et al., 2001. Eur. J. Endocrinology 144:145-54; Moreno et al., 2008. Thyroid 18:239-253), a plasma membrane-impermeable form of tetrac (i.e., nano-tetrac) has been formulated in which nonreactive nanoparticles are covalently bound to the outer ring hydroxyl group of tetrac (either directly or via a linker). The presence of the nanoparticle does not inhibit the binding of the exposed ligand (tetrac) to the plasma membrane integrin αvβ3 (*Cell Cycle*, 2009). Cetuximab did not inhibit proliferation of ER-negative breast cancer MDA-MB cells significantly, however, simultaneous treatment with tetrac and cetuximab increased inhibition of cell proliferation. (See FIG. 10).

Any of the thyroid hormone analogs used herein can be reformulated into a nanoparticle (e.g., by conjugation to a polymer). Conjugation of any of the compounds described herein can be accomplished via a covalent bond, e.g., an anhydride bond, an ester bond, an ether bond, or a sulfur linkage or any other construct that limits action of the thyroid hormone analog to the cell surface receptor. Those skilled in the art will recognize that such reformulation prevents transport of the agent into the cell. The use of thyroid hormone analog nanoparticles is contemplated in order to limit their action to the integrin receptor and to increase the half life of the thyroid hormone analog. Thus, these thyroid hormone analog nanoparticles represent novel structures of choice for induction of apoptosis in cancer cells.

Exemplary polymers that the agents such as the thyroid hormone analogs can be conjugated to include, but are not limited to polyvinyl alcohol, acrylic acid ethylene co-polymer, methoxypolyethylene, polyethyleneglycol (PEG), polyacrylic acid, polylactic acid, agarose, polyglycolide, polylactide, PEO, m-PEG, PVA, PLLA, PGA, poly-L-lysine, Human Serum Albumin, cellulose derivatives, carbomethoxy/ethyl/ hydroxypropyl, hyaluronic acid, folate linked cyclodextrin/ dextran, sarcosine/amino acid spaced polymer, alginate, carrageenan, pectin/chitosan, chitosan, dextran, collagen, polyamine, poly aniline, poly alanine, polytrytophan, poly tyrosine, polylactide-co-glycolide (PLG), polylactic-co-glycolic acid) (PLGA), or polylysyl glycolide having different molecular weights ranging from 2,000-20,000 Dalton. Other suitable polymers include, by way of non-limiting example, polyglycolide, polylactide, or copolymers thereof.

Thyroid hormone has been shown to stimulate HIF1α gene expression by a PI3K-dependent process. (See, Lin et al., 2009. Am. J. Physiol Cell Physiol 296:C980-C991 (incorporated herein by reference)). Thus, thyroid hormone, at least in the form of the 3,5,3'-triiodo-L-thyronine (T3) analogue (but not necessarily limited to this form) is a natural and endogenous inhibitor of the crucial action of cetuximab on HIF1α. Thyroid hormone is anti-apoptotic via its action on integrin αvβ3. Moreover, tetrac blocks the anti-apoptotic effect of endogenous thyroid hormone. Therefore, combination treatment with cetuximab and tetrac or nano-tetrac in order to decrease HIF1α gene expression by a PI3K-requiring process, is proposed. Such a combination has an additional advantage of summated anti-angiogenic actions.

This action of thyroid hormone on HIF1α can be blocked by tetraiodothyroacetic acid (tetrac) and nanoparticulate tetrac, which have been shown to inhibit the actions of thyroid hormone analogs at the cell surface receptor for the hormone that have been described on the integrin αvβ3. (See Bergh et al., 2005. Endocrinology 146:2864-71 (incorporated by reference)). Thus, the combination of cetuximab and unmodified or nanoparticulate tetrac (i.e., nano-tetrac), when administered concurrently (i.e., in combination), can be used for the treatment of cancer and is intended specifically and selectively to protect the clinically desirable inhibitory activity of cetuximab on PI3K-dependent expression of the HIF1α gene.

Additionally, it will be readily apparent to those skilled in the art that cetuximab, whether unmodified or in nanoparticle form, can be used in combination with other anti-angiogenic thyroid hormone analogs, such as, for example, triiodothyroacetic acid (triac), the deaminated analog of 3,5,3'-triiodothyronine ($T_3$). Again, triac can be used either unmodified or as a nanoparticulate.

As shown in FIG. 1, a bellows perfusion cell culture system has been developed in which to define in vitro the anti-proliferative pharmacodynamics (PD) of tetrac in cancer cells. The system is based on a perfusion ("hollow fiber") model used to estimate pharmacokinetics (PK) and PD of antimicrobial agents (e.g., antibiotics) against epidemiologically important infectious pathogens. (See Bilello et al., 1994. Antimicrob Agents Chemother 38:1386-1391; Drusano et al. 2002. Antimicrob Agents Chemother 46:464-70; Louie et al., 2009. Antimicrob Agents Chemother 53:3325-3330). The standard hollow fiber (dialysis) system has been modified by replacing the hollow fiber ad chamber paradigm with a flow-through Bellco perfusion bottle pumping station system (Bellco Biotechnology, Vineland, N.J.). In this system, cells of cancer lines of interest are grown on plastic flakes suspended in a flow-through, bellows-agitated system that allows for homogeneous exposure of cells to drug/drug metabolite solutions and frequent sampling of cells for viability. Harvesting of ten flakes provides sufficient numbers of cells for analytic purposes, including flow cytometric studies. Cellular outcomes that are measurable include cell cycle arrest, stages of apoptosis, and total cell numbers. The system can also be used to estimate PK and PD of single new biopharmaceutical cancer chemotherapeutic agents.

Using this system, nano-tetrac was found to inhibit cell proliferation more effectively than tetrac does. Specifically, unmodified tetrac inhibits the proliferation of cancer cells and does so with differing IC50's in different cell lines. When covalently linked to poly (lactic-co-glycolic) acid nanoparticles (PLGA), tetrac does not enter the cell, acts exclusively at the cell surface integrin receptor, and suppresses cancer cell proliferation to a greater degree than unmodified tetrac. Moreover, tetrac and nano-tetrac induced apoptosis by suppressing the proliferative activity of thyroid hormone and by differentially affecting expression of anti-apoptotic and pro-apoptotic cells to reduce cancer cell survival.

This perfusion bellows system also permitted analysis of treatment of cancer cells with tetrac or nano-tetrac in combination with other chemotherapeutic agents. For example, in the present studies, both unmodified and nano-tetrac were tested for anti-proliferative efficacy in combination with other anticancer agents such as the commercially-available monoclonal anti-epidermal growth factor receptor (EGFR) antibody Erbitux® (cetuximab). Additive pharmacodynamic results using tetrac in combination with Erbitux® (cetuximab) were observed. Moreover, when tested in an in vitro model, tetrac and nano-tetrac were shown to have favorable pharmacodynamics as anti-cancer agents, whether acting alone or in conjunction with other agents such as cetuximab.

Figure 3B:
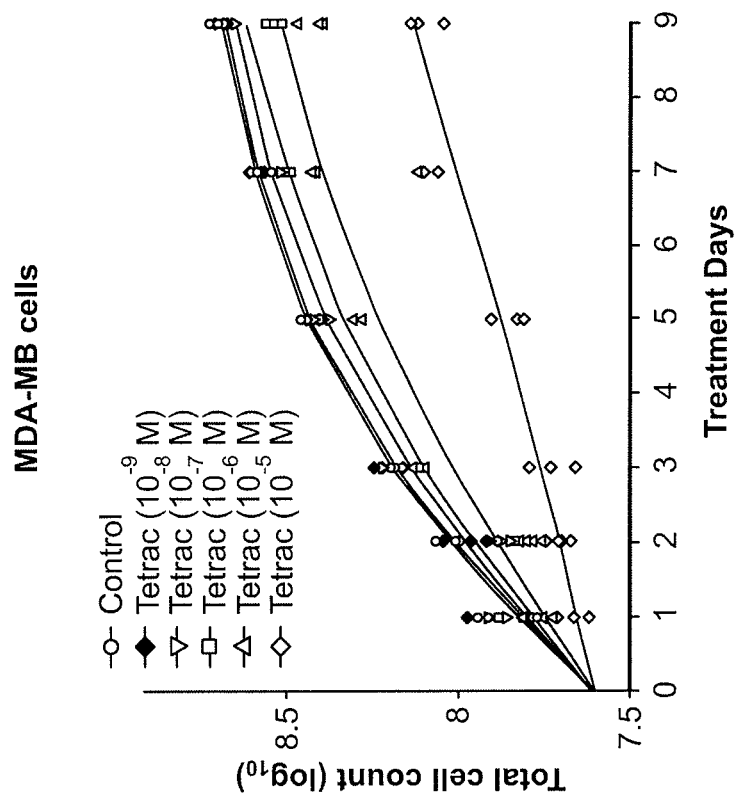
FIG. 3A shows U87MG cells and FIG. 3B shows MDA-MB cells treated daily with tetrac ($10^{-9}$ to $10^{-5}$ M).
Figure 6C:
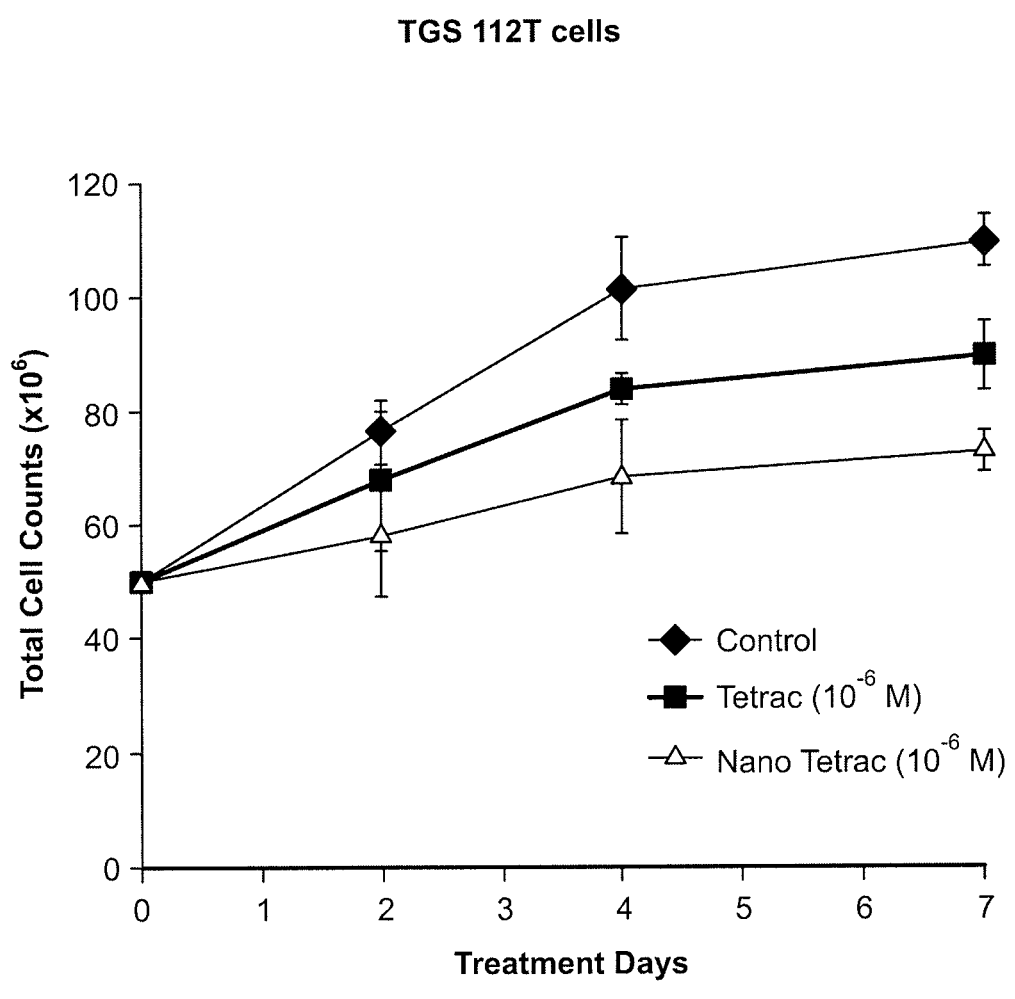
In FIG. 6C, TGS112T cells were treated daily with $10^{-6}$ M tetrac or nano-tetrac. Cells were harvested at the time points as indicated. Total cell numbers taken after each treatment were used as indicator for tetrac- or nano-tetrac-induced anti-proliferation.

Tetrac has been shown to block thyroid hormone-induced biological activities such as activation of MAPK and PI-3K signal transduction pathways (see Bergh et al., 2005. Endocrinology 146:2864-71; Davis et al., 2006. Cancer Res. 66:7270-75; and Lin et al., 2009. Am. J. Physiol. Cell Physiol. 296:C980-91), cell proliferation (see Davis et al., 2006. Cancer Res. 66:7270-752), thyroid hormone inhibition of resveratrol-induced apoptosis (see Lin et al., 2008. Carcinogenesis 29:62-69), and sensory neuron sodium current (see Yonkers et al., 2008. J. Neurophysiol. 100:2719-25) through interference with the binding of thyroid hormone to integrin αvβ3. (See Bergh et al., 2005. Endocrinology 146:2864-71; Davis et al., 2006. Cancer Res. 66:7270-75; Lin et al., 2009. Am. J. Physiol. Cell Physiol. 296:C980-91; and Rebbaa et al., 2008. Angiogenesis 11:269-76). However, tetrac alone can actually stimulate cell proliferation when it gains access to the cell interior. (See FIGS. 3 and 6).

Figure 5B:
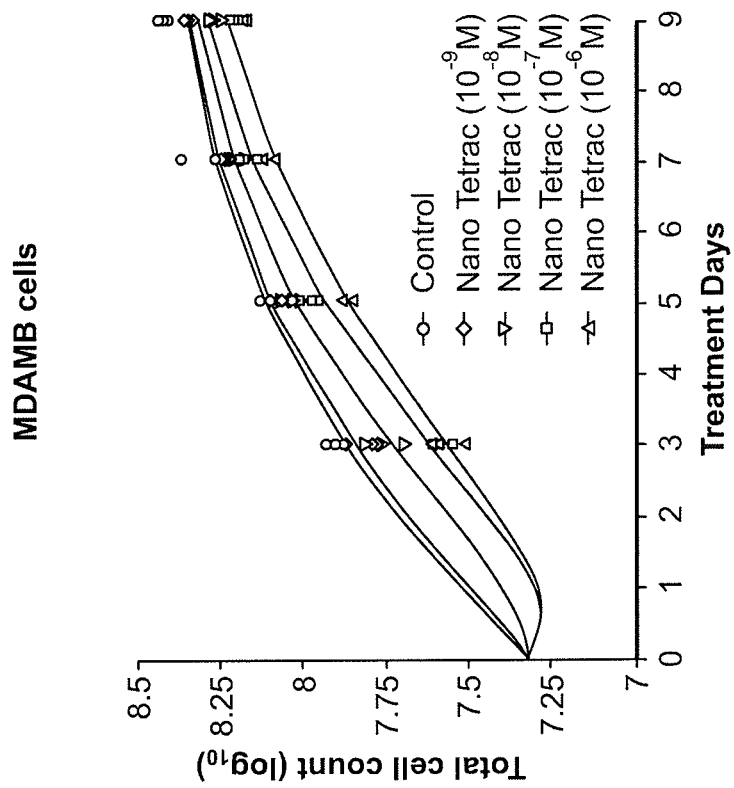
FIG. 5B shows MDA-MB cells that were treated daily with different concentrations of tetrac nano ($10^{-9}$ to $10^{-6}$ M). Cells were harvested at the time points indicated. Total cell numbers taken after each treatment were used as indicators of tetrac and nano-tetrac-induced anti-proliferation.
Figure 5A:
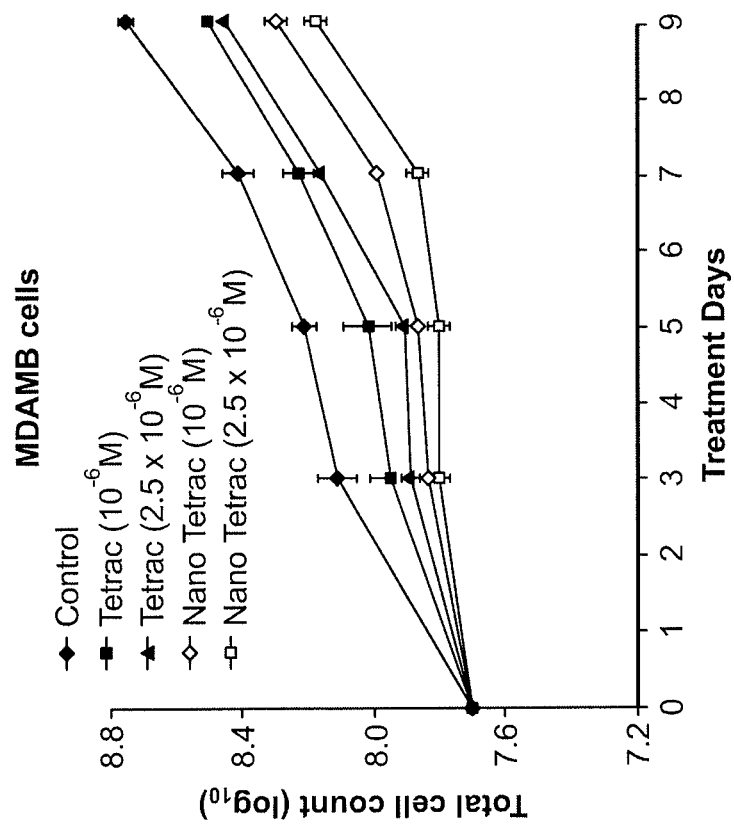
FIG. 5A shows MDA-MB cells that were treated daily with different concentrations of tetrac and nano-tetrac ($2.5 \times 10^{-6}$ and $10^{-6}$ M).
Figure 9A:
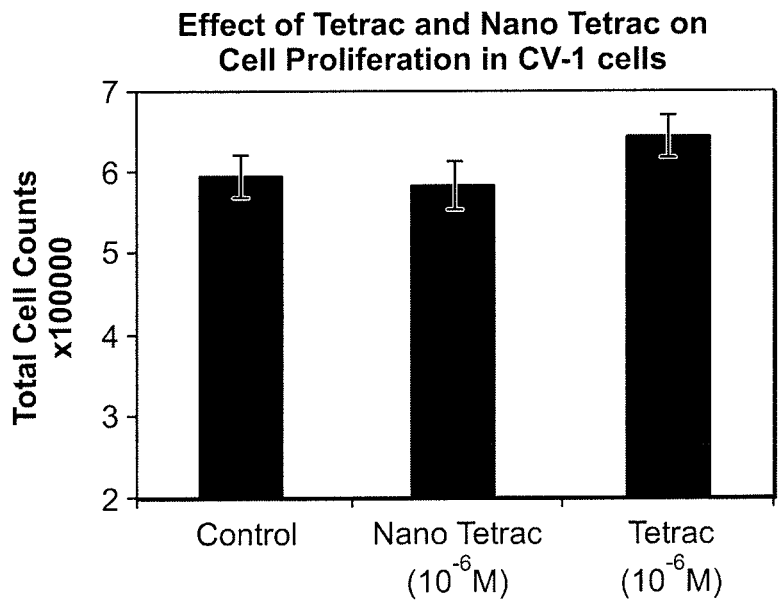
FIG. 9 is a series of graphs showing the comparison of nano-tetrac and tetrac on cell proliferation in non-malignant cells. CV-1 cells (FIG. 9A) and 293 T cells (FIG. 9B) were treated daily with $10^{-6}$ M tetrac or nano-tetrac. Cells were harvested at the time points indicated. Total cell numbers taken after each treatment were used as an indicator for tetrac- or nano-tetrac-induced anti-proliferation.
Figure 9B:
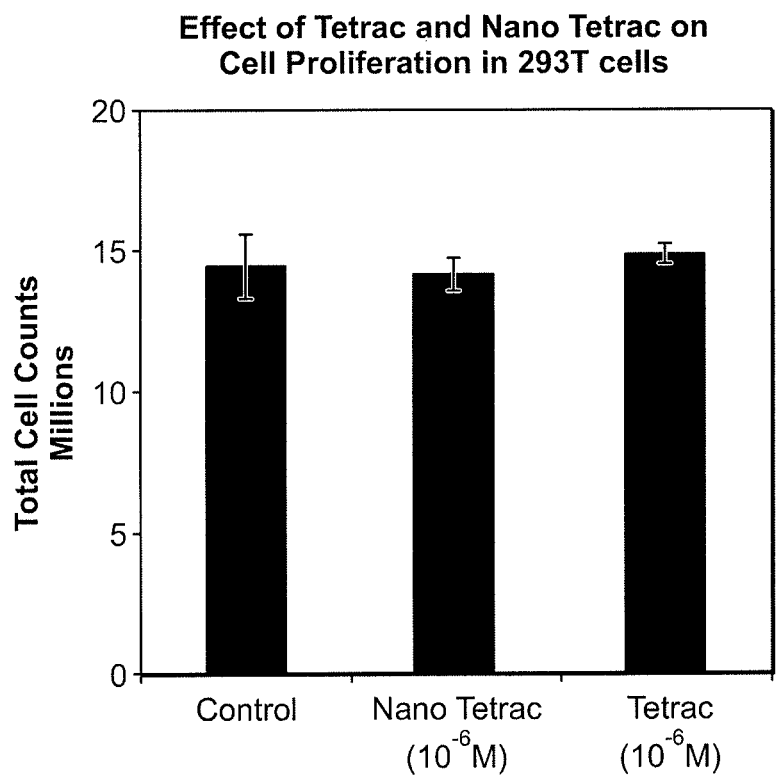

However, the use of a nanoparticulate formulation of tetrac that effectively prevents access of tetrac to the interior of cells. Thus, the anti-proliferative effects induced by these tetrac equivalents can be compared. Nanoparticulate tetrac is two times more effective than unmodified tetrac as an anti-proliferative agent (see FIG. 5A) and is five times more effective than tetrac in opposing $T_4$-induced [$^3$H]-thymidine incorporation (DNA replication) (see FIG. 6B). Morphological studies also indicate that nano-tetrac causes a change in cell shape after 5 days of incubation. Neither nano-tetrac nor tetrac affect normal, non-cancer cell proliferation even when a high concentration ($10^{-6}$ M) is used. (See FIG. 9).

Radiolabeled doxorubicin uptake in cells is enhanced by tetrac, suggesting that one or more export mechanisms for chemotherapeutic agents are inhibited. (See Rebbaa et al., 2008. Angiogenesis 11:269-76). Tetrac is anti-proliferative in several cancer cell lines and has been shown to enhance the cellular response in vitro to doxorubicin, etoposide, cisplatin, and trichostatin A in resistant tumor cell lines derived from neuroblastoma, osteosarcoma, and breast cancer. (See Rebbaa et al., 2008. Angiogenesis 11:269-76). Tetrac also enhances cancer cell susceptibility to apoptosis, suggesting that the agent may target multiple drug resistance mechanisms.

The anti-proliferative effect of tetrac and/or nano-tetrac on cancer cells in the perfusion bellows cell system shown in FIG. 1 was seen in as early as 3 days after tetrac or nano-tetrac were added to the system (See FIG. 3). The anti-cancer effects of tetrac and nano-tetrac in xenografts has been established in 3 days after the onset of drug administration. (See D'Arezzo et al., 2004. Endocrinology 145:5694-5703). While the effects of tetrac in the xenograft model have been shown to involve both primary effects on tumor cell proliferation as well as an anti-angiogenesis effect, the effect of tetrac and nano-tetrac in the perfusion bellows cell system is the suppression of cell proliferation.

Figure 2A:
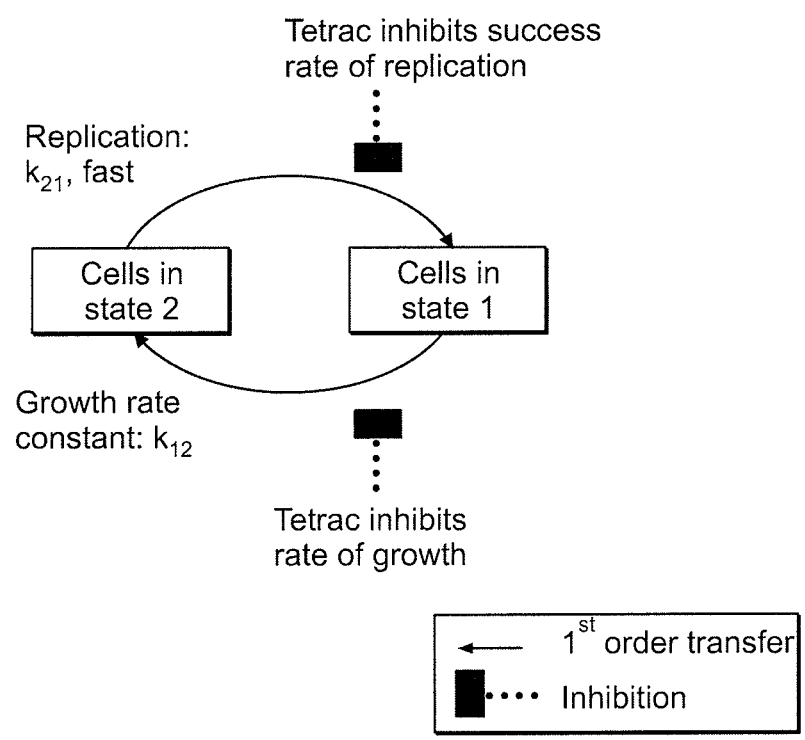
FIG. 2A is a diagram of a mathematical model that assumes two populations of cells in different states of the cell cycle: cells that are preparing for replication (state 1) and cells that are immediately "pre-replication" (state 2). Cells transition from state 1 to state 2 by a first-order growth rate constant, while replication from state 2 to state 1 is assumed to be fast.
Figure 2B:
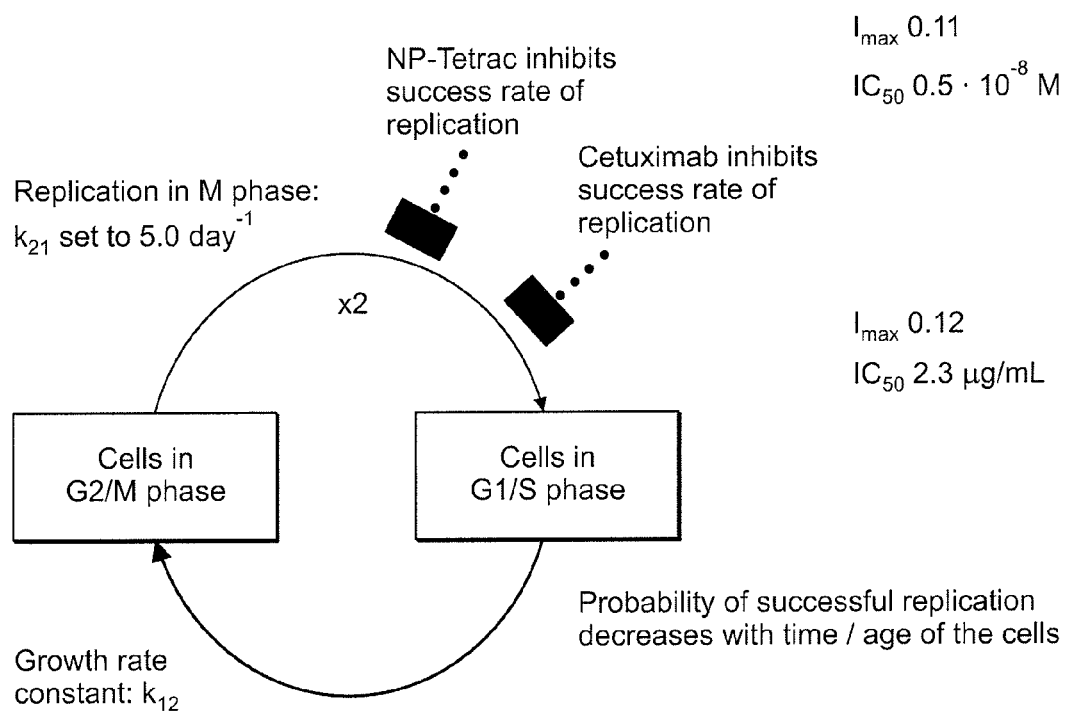
FIG. 2B is a diagram of a pharmacodynamic model. This model assumes that both drugs act on independent pathways and includes a small antagonistic term. The observed effect of the combination is larger than a model which assumes both drugs acting on the same pathway would predict.

Moreover, in the bellows perfusion cell culture system, the cells are alternately exposed to fresh medium and air. (See FIG. 1). This provides optimized growth conditions for cancer cells by maximizing nutrient uptake and oxygen transfer. Cells can therefore be studied over longer time periods, e.g., up to three weeks as shown in the experiment with tetrac and MDA-MBcells in FIG. 3C and the phase where cell counts have reached a plateau can be observed. By obtaining information about both the slope and the plateau of the cell count with respect to time and by utilizing mathematical modeling (described in Example 1, infra), two different effects of tetrac on cancer cells can be distinguished. (See FIG. 2).

In addition to allowing for the treatment of the cells with constant drug concentrations (reflecting in vivo continuous infusion treatment), other dosing regimens such as multiple short-term or intermittent infusions or brief injections can also be studied in the perfusion bellows cell culture system by adjusting the flow rate of the medium and the dosing schedule. In this way, drug concentration/time profiles such as those expected in human or animal studies can be simulated and the effects on cancer cells of changing drug concentrations as anticipated in vivo may be observed in the in vitro bellows system. Taken together with mathematical modeling, these in vitro systems can support optimal design of animal and human studies thereby saving time and costs in drug development. Likewise, because a wider range of drug concentrations can be studied in vitro than in animal models, selection of appropriate concentrations or in vivo studies may become more efficient.

As described in detail in Example 1, infra, mathematical modeling was utilized to increase the amount of information gained from the reported experiments. By considering the whole time course of cell counts in response to multiple concentrations of tetrac and control treatment simultaneously, more insight can be gained into the dose-response relationship and the mechanism of action of a drug. Also mechanism-based models are more useful in making predictions (e.g., for other dosage regimens) than empirical growth models.

For human glioblastoma (U87MG) cells, mathematical modeling suggested a higher maximum effect but lower sensitivity of the effect on probability of successful replication compared to the effect on rate of growth for both unmodified and nano-tetrac. For both effects, this sensitivity was higher towards nano-tetrac than unmodified tetrac. This difference may be explained by the ability of unmodified tetrac to penetrate into cells and thereby exert proliferative effects in addition to the anti-proliferative effects initiated at the cell surface receptor. Therefore, the net anti-proliferative effect of unmodified tetrac is decreased, whereas because nano-tetrac does not gain access to the cell interior, the overall anti-proliferative effect is unchanged.

In human breast cancer (MDA-MB) cells two different modeling results are available. For the first model sparse data from two different experiments were pooled (see Table 1, study 1, infra), whereas the second set of parameter estimates is based on a single large experiment with rich sampling (see Table 1, study 2, infra). Therefore the results from study 2 appear more reliable. MDA-MB cells appeared to have similar (or lower) sensitivity to nano-tetrac compared to unmodified tetrac for the effect on growth rate and a higher sensitivity for the effect on success of replication. These mechanism-based models adequately described the cell counts over time and can be used to support the design future experiments with tetrac and nano-tetrac.

Inhibition by nano-tetrac of thyroxine-induced MAPK activation and PCNA expression in cultured cells correlates well with the anti-proliferative effects induced by tetrac and nano-tetrac in the perfusion bellows cell culture system. Results of anti-proliferation studies with nano-tetrac analogues in the bellows system are likely to be more predictive of in vivo effects than studies performed in Petri dish cell cultures. The continuous cell perfusion studies provide useful pharmacodynamic information for the application of new drugs to the treatment of a variety of neoplastic diseases.

This, in combination with pharmacodynamic modeling and by including information about the expected pharmacokinetics of a drug, allows the perfusion bellows cell culture system to be used to study the dose-response relationships of anti-neoplastic agents over a very wide concentration range in vitro, and can support translation from in vitro models to animal models and human clinical trials.

Thus, combination of tetrac and cetuximab, whether unmodified or modified as a nanoparticulate, represents a novel treatment for the inhibition of PI3K-dependent HIF1α gene expression in cancer cells. Moreover, the combination excludes the antagonistic action of host endogenous thyroid hormone on the HIF1α gene expression. (See, Lin et al., 2009. Am J. Physiol Cell Physiol 296:C980-C991). Likewise, an anti-estrogen compound can be used in conjunction with the combination of tetrac and cetuximab, e.g., in estrogen-bearing breast cancers or lung cancers that are ER-positive. (See Koutras et al. *Mol Cancer* 8(1):109, 2009). That is, the combination of agents is directed at multiple sites of vulnerability in such cancer cells.

Additionally, the combination of cetuximab and tetrac in a vehicle, such as a nanoparticle, in further combination with one or more conventional cancer chemotherapeutic agents, permits delivery of such chemotherapeutic agents directly to integrin αvβ3-bearing tumor cells. Suitable chemotherapeutic agents include, but are not limited to, doxorubicin, etoposide, cyclophosphamide, 5-fluoracil, cisplatin, trichostatin A, paclitaxel, gemcitabine, taxotere, cisplatinum, carboplatinum, irinotecan, topotecan, adrimycin, bortezomib, and atoposide or any combinations or derivatives thereof.

The agents described herein (e.g., cetuximab and the anti-angiogenic thyroid hormone analog) are preferably administered in a formulation (including the analogs, polymeric forms, and/or any derivatives thereof) together with a pharmaceutically acceptable carrier. Any formulation or drug delivery system containing the active ingredients, which is suitable for the intended use that are generally known to those of skill in the art, can be used. Suitable pharmaceutically acceptable carriers for oral, rectal, topical, or parenteral (including subcutaneous, intraperitoneal, intramuscular and intravenous) administration are known to those of skill in the art. Those skilled in the art will recognize that the carrier must be pharmaceutically acceptable in the sense of being compatible with the other ingredients of the formulation and not being deleterious to the recipient thereof.

Formulations suitable for parenteral administration may include sterile aqueous preparations of the active compound, which are preferably isotonic with the blood of the recipient. Thus, such formulations may contain distilled water, 5% dextrose in distilled water or saline. Useful formulations may also include concentrated solutions or solids containing any of the compositions or compounds described herein, which upon dilution with an appropriate solvent, give a solution suitable for parental administration.

For enteral administration, a compound can be incorporated into an inert carrier in discrete units such as capsules, cachets, tablets, or lozenges, each containing a predetermined amount of the active compound(s); as a powder or granules; or a suspension or solution in an aqueous liquid or nonaqueous liquid, e.g., a syrup, an elixir, an emulsion or a draught. Suitable carriers may be starches or sugars and may include lubricants, flavorings, binders, and other materials of the same nature.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

Formulations for rectal administration may be presented as a suppository with a conventional carrier, e.g., cocoa butter or Witepsol S55 (trademark of Dynamite Nobel Chemical, Germany), for a suppository base.

Alternatively, the compounds may be administered in liposomes, microspheres (or microparticles), or attached to nanoparticles. Methods for preparing liposomes and microspheres for administration to a patient are well known to those of skill in the art. For example, U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," Drug Carriers in Biology and Medicine, pp. 287-341 (Academic Press, 1979).

Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. (See, for example, U.S. Pat. Nos. 4,906,474; 4,925,673; and 3,625,214, and Jein, 1998. TIPS 19:155-157), the contents of which are hereby incorporated by reference.

Any of the compounds described herein, (e.g., cetuximab, tetrac or triac, and/or the polymeric forms thereof) can be formulated into nanoparticles. Preferred nanoparticles are those prepared from biodegradable polymers, such as, for example, polyethylene glycols, polyglycolide, polylactide and copolymers thereof. Those of skill in the art can readily determine an appropriate carrier system (i.e., the polymer) used for preparation of nanoparticulate forms of cetuximab and/or tetrac (or triac) depending on various factors, including, for example, the desired rate of drug release and the desired dosage.

In some embodiments, the formulations are administered via catheter directly to the inside of blood vessels. The administration can occur, for example, through holes in the catheter. In those embodiments wherein the active compounds have a relatively long half life (on the order of 1 day to a week or more), the formulations can be included in biodegradable polymeric hydrogels, such as those disclosed in U.S. Pat. No. 5,410,016 to Hubbell et al. These polymeric hydrogels can be delivered to the inside of a tissue lumen and the active compounds released over time as the polymer degrades. If desirable, the polymeric hydrogels can have microparticles or liposomes which include the active compound dispersed therein, providing another mechanism for the controlled release of the active compounds.

The formulations may also be presented in unit dosage form and may be prepared by any of the methods well known in the art of pharmacy. For example, such methods include the step of bringing the active compound(s) into association with a carrier, which constitutes one or more accessory ingredients. In general, the formulations are prepared by uniformly and intimately bringing the active compound(s) into association with a liquid carrier or a finely divided solid carrier and then, if necessary, shaping the product into desired unit dosage form.

The formulations can optionally include one or more additional components, such as various biologically active substances including antivirals, antibacterials, anti-inflammatories, immuno-suppressants, analgesics, vascularizing agents, and/or cell adhesion molecules.

In addition, any of the formulations of the invention may further include one or more optional accessory ingredient(s) routinely utilized in the art of pharmaceutical formulations, e.g., diluents, buffers, flavoring agents, binders, surface active agents, thickeners, lubricants, suspending agents, and/or preservatives (including antioxidants) and the like.

The invention will be further illustrated in the following non-limiting examples.

EXAMPLES

Example 1

Pharmacodynamic Modeling of Tetraiodothyroacetic Acid-Induced Anti-Proliferation in Cancer Cells Using a Perfusion Bellows Cell Culture System Materials and Methods
Cell Lines.
Human glioblastoma cells (U87MG), human breast cancer MDA-MB-231 cells (MDA-MB), African green monkey kidney epithelial CV-1 cells and human embryonic kidney 293T cells were purchased from ATCC. Human follicular thyroid cancer FTC236 cells were generously provided by Dr. Orlo Clark (University of California at San Francisco—Mt. Zion Medical Center, San Francisco, Calif.). Human adenoid cystic carcinoma cells (TGS112T) were made available from the laboratory of Dr. L. Queimado at the University of Oklahoma. U87MG cells were maintained for study in MEM supplemented with 10% fetal bovine serum (FBS), and MDA-MB, CV-1 and 293T cells were maintained in DMEM that was supplemented with 10% FBS. Follicular thyroid cancer cells were maintained in 50% DMEM/50% Ham's F-12 plus 10 mU/ml of TSH (Sigma). TGS112T cells were maintained in RPMI medium that contained 20 ng/mL epidermal growth factor (EGF) (200 μL of stock at 10 μg/mL), 400 ng/mL hydrocortisone (800 μL of stock at 50 μg/mL) and 5000 ng/mL insulin (50 μL of stock at 10 mg/mL). Cultured cells were maintained in a 5% $CO_2$/95% air incubator at 37° C.

Pharmacodynamics (PD) of Tetrac.
FIG. 1 shows a newly developed bellows bottle cell culture system that is a disposable bioreactor capable of high density cell culture for studies of anti-cancer drugs. Each cell culture system is a compressible (bellows) 500 mL bottle which contains cell culture medium and specially-treated polymer flakes to which cells spontaneously attach and grow. Through moving bellows and porous membranes, the level of the medium in the bottle changes periodically. Consequently, the cells are alternately submerged in the culture medium, then exposed to 5% $CO_2$/95% air which creates a dynamic interface between air and medium on the cell surface that maximizes nutrient uptake and oxygen transfer. The system provides a low shear, high aeration and foam-free culture environment. Proprietary treatment of the surfaces of the flakes enables seating and harvesting of cells and secreted proteins are readily isolated from the perfusate.

In a non-perfusion bellows cell culture system that was also used, the medium in each bottle was replaced by fresh medium every 24 h. In the perfusion bellows cell culture system, medium was progressively refreshed over 24 h, i.e., one complete change of medium occurred over 24 h.

In establishing the system, $5 \times 10^7$ cells were seeded in perfusion and non-perfusion bellows bottles and incubated overnight at 37° C. After that, flakes were harvested, trypsinized and cells were collected. Cell numbers were counted. The numbers of cells that attached to were $10$-$15 \times 10^6$ per bottle. For experiments, the perfusion bellows cell culture system was run for 2 d prior to starting experiments. The cell numbers at this point were about $30$-$50 \times 10^6$ cells/bottle. Cell cultures were then exposed to 1% FBS-containing medium. Tetrac or nano-tetrac was added to the medium in the reservoir bottle to achieve the final concentrations reported for each experiment.

Liquid Chromatography-Tandem Mass Spectrometry (LC/MS/MS)

In LC/MS/MS experiments, medium samples (20 μL) were injected onto an HP 1100 series HPLC system (Agilent Technologies, Palo Alto, Calif., USA), equipped with a narrow-bore column Zorbax Eclipse XDB-C18 (5 μm, 150×2.1 mm; Agilent). Separation was performed using a mobile phase of 0.1% (v/v) acetic acid (A) and 100% acetonitrile (B), with a linear gradient of 20-60% B over 25 min. Flow rate was maintained at 0.2 mL $min^{-1}$ and elution was monitored by a diode array detector (200-600 nm). The LC effluent was then introduced into a turbo ion-spray source on a Q/STAR-XL quadruple/time-of-flight (TOF) hybrid mass spectrometer (Applied Biosystems, Foster City, Calif., USA). Negative ESI mass spectra were acquired over the range from m/z 100 to 400. The electrospray voltage was set at −4.5 kV and the source temperature was maintained at 475° C. CID spectra were acquired using nitrogen as the collision gas under collision energies of 25-55 V. High purity nitrogen gas (99.995%) was used as the nebulizer, curtain, heater and collision gas source.

Thymidine Incorporation.

TGS112T cells were seeded in 24-well trays and exposed to 10% hormone-depleted FBS-supplemented medium for 2 d, then treated with 0.25% hormone-depleted FBS-supplemented medium prior to starting the experiments. Aliquots of cells were treated with $T_4$, tetrac or nano-tetrac as indicated, as well as 1 μCi [$^3$H]-thymidine (final concentration, 13 nM) for 24 h. Cells were then washed twice with cold PBS. TCA (5%, 1 mL) was added and the plate was held at 4° C. for 30 min. The precipitate was washed twice with cold ethanol; 2% SDS (1 mL) was added to each well and the TCA-precipitable radioactivity was quantitated in a liquid scintillation counter.

Immunoblotting.

The techniques have been described in a number of publications. (See Davis et al., 2006. *Cancer Res.* 66:7270-7275; Lin et al., 2007. *Steroids*. 72:180-187; Lin et al., 2008. *Carcinogenesis*. 29:62-69; and Davis et al., 2004. *Circ Res.* 94:1500-1506, each of which is herein incorporated by reference in its entirety). Nucleoproteins were separated on discontinuous SDS-PAGE (9% gels) and the proteins transferred by electroblotting to nitrocellulose membranes (Millipore, Bedford, Mass.). After blocking with 5% milk in Tris-buffered saline containing 0.1% Tween, the membranes were incubated with selected primary antibodies overnight. The secondary antibodies were either goat anti-rabbit IgG (1:1000, Dako, Carpenteria, Calif.) or rabbit anti-mouse IgG (1:1000, Dako), depending upon the origin of the primary antibody. Immunoreactive proteins were then detected by chemiluminescence.

RT-PCR.

Total RNA was isolated as described previously. (See Lin et al., 2008. *Carcinogenesis*. 29:62-69). First strand complementary DNAs were synthesized from 1 μg of total RNA using oligo dT and AMV Reverse Transcriptase (Promega, Madison, Wis.). First-strand cDNA templates were amplified for GAPDH, c-fos, PIG3, c-Jun, and BAD mRNAs by polymerase chain reaction (PCR), using a hot start (Ampliwax, Perkin Elmer, Foster City, Calif.). Primer sequences were GAPDH [5'-AAGAAGATGCGGCTGACTGTCGAGC-CACA-3' (forward) (SEQ ID NO: 1) and 5'-TCTCATGGT-TCACACCCATGACGAACATG-3' (reverse) (SEQ ID NO:2)], c-fos [5'-GAATAAGATGGCTGCAGCCAAATGC-CGCAA-3'(forward) (SEQ ID NO:3) and 5'-CAGTCA-GAT-CAAGGGAAGCACAGACATCT-3' (reverse) (SEQ ID NO:4)], PIG3 [5'-TGGTCACAG-CTGGCTCCCAGAA-3' (forward) (SEQ ID NO:5) and 5'-CCGTGGAGAAGTGAG-GCAGAATTT-3' (reverse) (SEQ ID NO:6)], c-jun [5'-GGAAACGACCTTCTATGACGATGCCCTCAA-3' (forward) (SEQ ID NO:7) and 5'-GAACCCCTCCTGCT-CATCTGTCACGTTCTT-3' (reverse) (SEQ ID NO:8)] and BAD [5'-GTT-TGAGCCGAGTGAGCAGG-3' (forward) (SEQ ID NO:9) and 5'-ATAGCGCTGTGCTGCCCAGA-3' (reverse) (SEQ ID NO:10)]. The PCR cycle was an initial step of 95° C. for 3 min, followed by 94° C. for 1 min, 55° C. for 1 min, 72° C. for 1 min, then 25 cycles and a final cycle of 72° C. for 8 min. PCR products were separated by electrophoresis through 2% agarose gels containing 0.2 μg of ethidium bromide/ml. Gels were visualized under UV light and photographed with Polaroid film (Polaroid Co., Cambridge, Mass.). Photographs were scanned under direct light for quantitation and illustration. Results from PCR products were normalized to the GAPDH signal.

Flow Cytometry Analysis.

Cells were harvested from flakes by trypsinization, washed with PBS and were resuspended in 200 μL PBS ($1 \times 10^5$-$1 \times 10^6$ cells). To quantify cellular DNA content, cells were permeabilized by fixation with 70% ethanol for 30 min at 4° C. Samples can be stored in 70% ethanol at −20° C. for several weeks prior to propidium iodide (PI) staining and flow cytometric analysis. If cellular DNA quantification was performed on the same day of cell harvest, the cells were washed after permeabilization in PBS and resuspended in 500 μL PBS. Then 2.5 μL RNase (DNase-free) was added to the cell suspension and incubation was carried out at 37° C. for 30 min. The cell suspension was chilled on ice to 4° C. and 50 μL propidium iodide (PI) was added to the cell suspension. Samples were then kept in the dark at room temperature for 30 min, after which they were subjected to flow cytometry. Samples were analyzed on FACSCalibur™ (Becton Dickinson), using CellQuest software to determine DNA content. Fluorescence-activated cell sorting (FACS) analysis was performed using Annexin V-FITC and PI. The relative percentages of cells in $G_1$, S, or $G_2$/M phase were calculated from FL-2 histograms using ModFit LT software.

Statistical Methods and Calculations.

Immunoblot and nucleotide densities were measured with a Storm 860 phosphorimager, followed by analysis with ImageQuant software (Molecular Dynamics, Sunnyvale, Calif.). Student's t test, with P<0.05 as the threshold for significance, was used to evaluate the significance of the hormone and inhibitor effects.

Mathematical Modeling.

The time course of cell counts of the various cancer lines treated with different concentrations of tetrac or nano-tetrac was modeled by utilizing the pooled approach in NONMEM VI (version 6.2). All time points and treatment arms within each experiment were modeled simultaneously. A mechanism-based model (see Bulitta et al., 2009. *Antimicrob. Agents Chemother.* 53:46-56) was adapted to describe the proliferation of cancer cells and the inhibition of proliferation by tetrac. This model assumes two populations of cells in different phases of the cell cycle: cells that are preparing for replication (phase 1) and cells that are immediately "pre-replication" (phase 2). Cells transition from phase 1 to phase 2 by a first-order growth rate constant, while replication from phase 2 to phase 1 is assumed to be fast (see FIG. 2).

The number of cells in phase 1 and 2 are described by:

$$\frac{dC1}{dt} = Rep \cdot InhR \cdot k21 \cdot C2 - k12 \cdot Inhk \cdot C1$$

$$\frac{dC2}{dt} = -k21 \cdot C2 + k12 \cdot Inhk \cdot C1$$

$$Ct = C1 + C2$$

where C1 is the number of cells in phase 1, C2 the number of cells in phase 2, k21 the first order rate constant for replication (transition from phase 2 to phase 1), and k12 the first-order growth rate constant for transition from phase 1 to phase 2. The total number of cells Ct is the sum of C1 and C2. Rep is the replication efficiency factor which is described by:

$$Rep = 2 \cdot \left(1 - \frac{Ct}{Cmax + Ct}\right)$$

where Cmax is the maximum number of cells. Without tetrac, the replication efficiency factor approaches 2, which reflects a 100% probability of successful replication. InhR describes the inhibitory effect of tetrac on the probability of successful replication:

$$InhR = \left(1 - \frac{ImaxR \cdot Tetrac}{IC50R + Tetrac}\right)$$

Where ImaxR is the maximum effect of tetrac on probability of successful replication and IC50R is the tetrac concentration needed to achieve a half-maximal effect. Inhk describes the inhibitory effect of tetrac on the rate of growth:

$$Inhk = \left(1 - \frac{Imaxk \cdot Tetrac}{IC50k + Tetrac}\right)$$

Where Imaxk is the maximum effect of tetrac on rate of growth and IC50k is the tetrac concentration needed to achieve a half-maximal effect.

Results

Tetraiodothyroacetic Acid Inhibits Cancer Cell Proliferation.

The pharmacodynamics of tetrac as an anti-proliferative agent versus different cancer cells has been studied in the bellows cell culture system shown in FIG. 1.

Human glioblastoma U87MG cells were treated with different concentrations of tetrac ($10^{-9}$-$10^{-5}$M) for 7 d and tetrac was replenished daily. The turnover rate of tetrac in the culture system was measured. Tetrac detected was 75% of the original concentration after 24 h incubation in medium with 10% FBS in the absence of cells at both room temperature and 37° C. There was 12% tetrac decay when tetrac was incubated with cell cultures at 37° C. These results indicate that tetrac is stable in the perfusion bellows cell system.

Figure 3A:
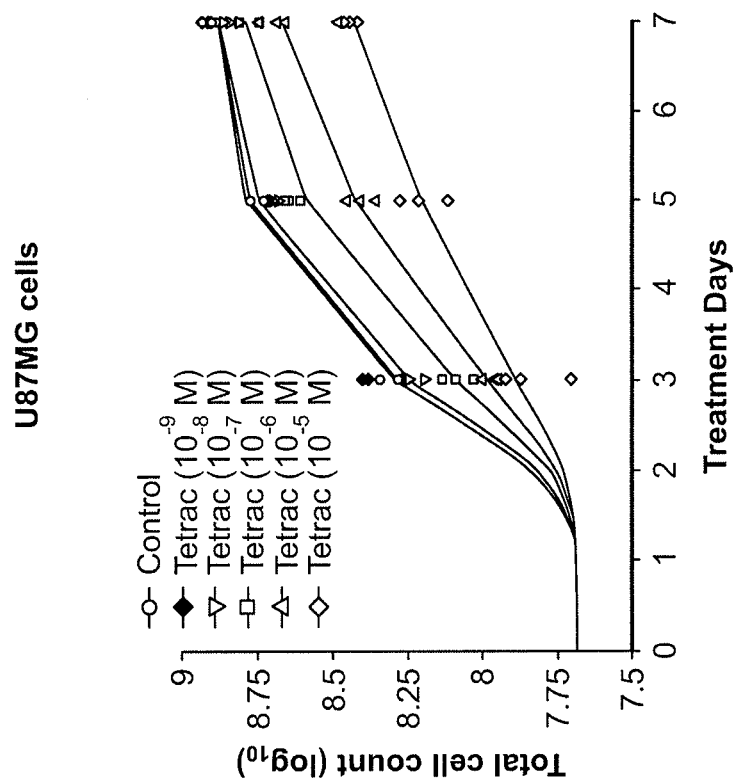
Figure 3C:
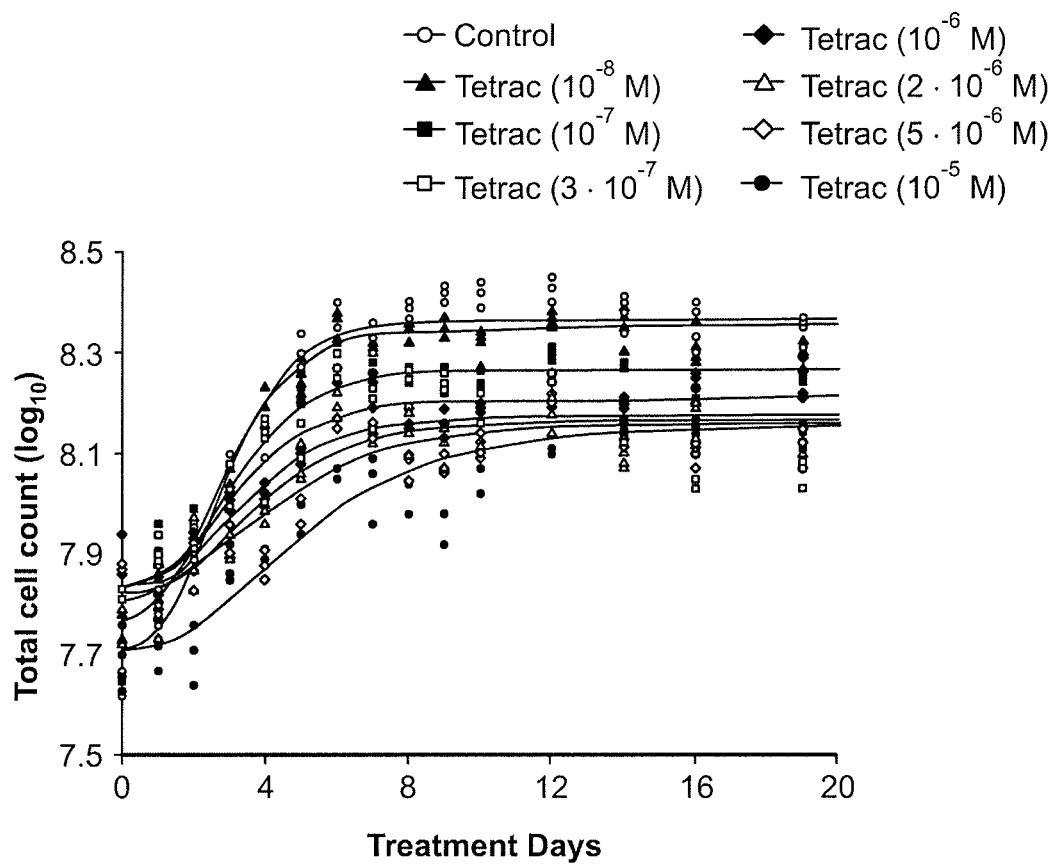
In FIG. 3C, MDA-MB cells were treated daily with different concentrations of tetrac ($10^{-8}$ to $10^{-5}$ M). Cells were harvested at the time points indicated. The total cell numbers taken after each treatment were used as indicators of tetrac-induced anti-proliferation.

A model including effects of tetrac on both rate of growth and probability of successful replication (see FIG. 2) and lag-time for growth during the first 2 d adequately described the time course of the cell counts. As shown in FIG. 3A, tetrac caused a concentration-dependent reduction in U87MG cell proliferation. While $10^{-9}$ M tetrac was the least effective, $10^{-8}$ and $10^{-7}$ M tetrac caused more than 15% and 28% decreases in cell counts when compared with the untreated control cells after 7-d treatment. (See FIG. 3A). Higher concentrations of the agent were proportionately more effective. The parameter estimates for IC50k and IC50R (shown in Table 1) suggested that the U87MG cells were more sensitive to the effect on rate of growth than to the effect on success of replication. However the capacity (Imax) was higher for the effect on success of replication (ImaxR>Imaxk).

TABLE 1

Parameter estimates for effects of tetrac on proliferation of cancer cells

| Cell line | Formulation | Effect on rate of growth | | Effect on success of replication | |
|---|---|---|---|---|---|
| | | Imaxk | IC50k (μM) | ImaxR | IC50R (μM) |
| U87MG | Tetrac | 0.57 | 0.047 | 0.92 | 47.4 |
| MDA-MB 231 | Tetrac (study 1)[c] | 0.19 | 0.0076 | 0.53[a] | 4.4 |
| MDA-MB 231 | Tetrac (study 2)[d] | 0.85 | 5.1 | 0.20 | 0.087 |
| U87MG | nano-Tetrac | 0.34 | 0.0001[b] | 1[a] | 0.089 |
| MDA-MB 231 | nano-Tetrac | 1 | 6.3 | 1[a] | 0.0086 |

[a]Imax at time = 0, Imax decreases with time (potentially due to functional adaption of the cells or the presence of two or more subpopulations with different sensitivities towards tetrac
[b]fixed as the lowest concentration studied was 0.001 μM
[c]sparse sampling, data pooled from two different studies
[d]rich data from one single study over 19 days The IC50 estimates for tetrac nanoparticles (nano-tetrac) are hypothetical concentrations assuming all of the tetrac bound on the nanoparticle is available for binding to the integrin receptor.

The anti-proliferative effect of tetrac in human estrogen receptor (ER)-negative breast cancer MDA-MB cells was also studied. Aliquots of cells were treated with several concentrations of tetrac ($10^{-9}$-$10^{-5}$M) for 9 d and tetrac was replenished daily, Cells were then harvested and counted. The results presented in FIG. 3B reveal a concentration-dependent effect of tetrac on MDA-MB cell proliferation. The highest tetrac concentration ($10^{-5}$M) induced a large anti-proliferative effect whereas at lower concentrations tetrac did not show anti-proliferative effects during the earlier days of treatment. (See FIG. 3B). The results shown in FIG. 3B are pooled data from two experiments (one with sampling on days 1 and 2, and one with sampling on days 3, 5, 7, and 9) in MDA-MB cells with the same tetrac concentrations investigated. Modeling suggested a higher sensitivity (lower IC50) for the effect on growth rate and a larger capacity (larger Imax) of the effect on replication. The model assumed a decrease in ImaxR over time which could be due to functional adaptation of the cells or the presence of two or more subpopulations with different sensitivities towards tetrac.

In another study, MDA-MB cells were treated with 7 different concentrations of tetrac ranging from $10^{-8}$ to $10^{-5}$ M or with control medium for 19 d and total cell counts were determined every one or two days. (See FIG. 3C). A model including effects on both rate of growth and success of replication (see FIG. 2) and a lag-time of growth adequately described the data. The parameter estimates suggest a higher sensitivity (lower IC50) for the effect on probability of successful replication and a larger capacity (larger Imax) of the effect on rate of growth.

Figure 4A:
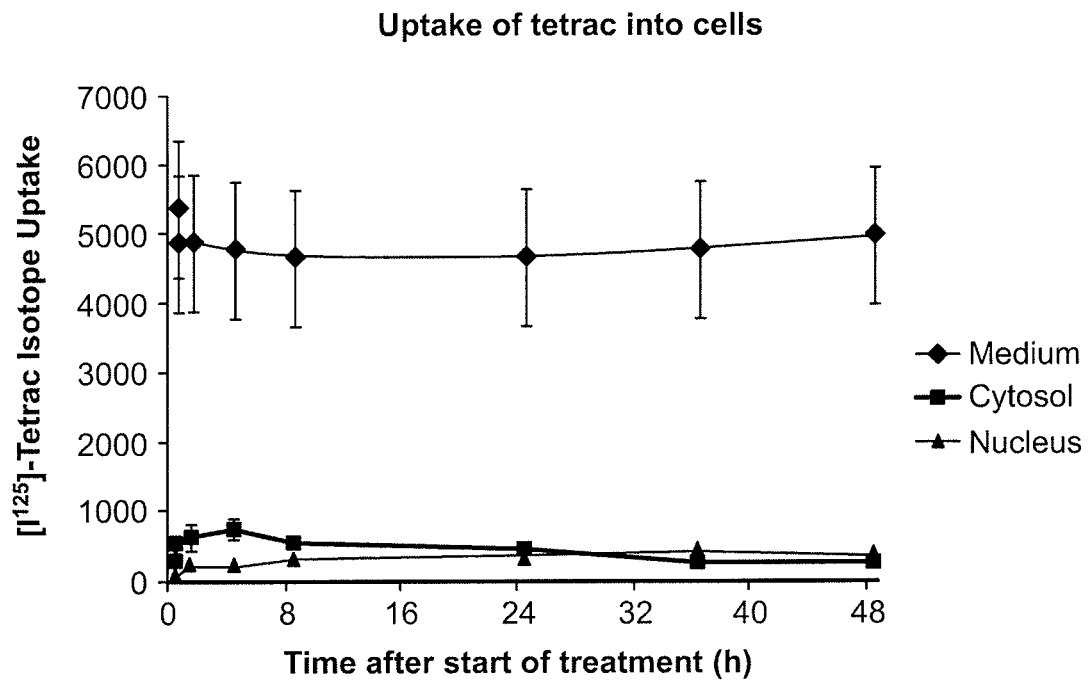
In FIG. 4A, cells were seeded in 100 mm Petri dishes and refed MEM containing 0.25% stripped serum for 2 days. $[^{125}I]$-tetrac ($0.227 \times 10^{-6}$ M) was added to Petri dishes at time points indicated. The final concentration of $[^{125}I]$-tetrac was $2.27 \times 10^{-11}$ M. Cells were harvested immediately after final tetrac adding. Cytosolic and nuclear proteins were separated as described previously. 10 μl of media, cytosolic and nuclear proteins were prepared for scintillation counting. The results are the average of four experiments.
Figure 4B:
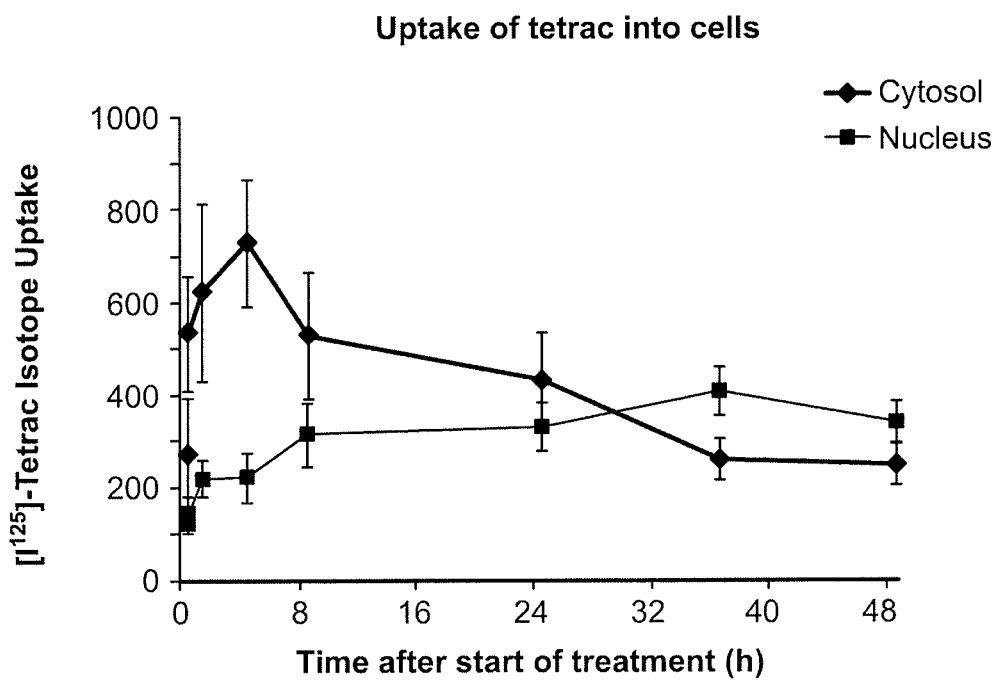
In FIG. 4B, the distribution of $[^{125}I]$-tetrac in cytosolic and nuclear fractions is shown.

Although tetrac does have a growth-suppressive effect late in the treatment period, it may also have a proliferative effect on cancer cells. This presumably reflects access of the agent to the cell interior where it is a thyroid hormone agonist (thyromimetic), rather than an inhibitor (see Lameloise et al., 2001. *Eur J Endocrinology* 144:145-154), as it is exclusively at the cell surface receptor. In order to examine whether tetrac enters cells, human glioblastoma U87MG cells were incubated over different time periods with [$^{125}$I]-labeled tetrac. Cells were harvested and medium, plasma membranes, cytosols and nuclear extracts were prepared for scintillation counting. [$^{125}$I]-Labeled tetrac reached the maximal concentration in the cytosolic fraction after 4 h incubation and increased in nuclear fractions after 36 h incubation. (See FIG. 4). Thus, tetrac enters relatively quickly into cytosol and more slowly into nuclei.

Nano-Tetrac Shows a Consistent Anti-Proliferative Effect in Cancer Cells.

In order to prevent uptake of tetrac by cancer cells, the hormone analogue was reformulated as a nanoparticle. The anti-proliferative effect of the resulting tetrac nanoparticles was then studied in MDA-MB cells. Cells were treated with constant concentrations of $10^{-6}$ and $2.5 \times 10^{-6}$ M tetrac or nano-tetrac for 9 d. Results indicate that the anti-proliferative effect of nano-tetrac in MDA-MB cells is more prominent than that of unmodified tetrac. (See FIG. 5A). There was a 100-fold concentration difference in anti-proliferation efficacy between tetrac and nano-tetrac. In another study MDA-MB cells were treated with 4 different concentrations of nano-tetrac ($10^{-9}$ to $10^{-5}$ M) for 9 d. (See FIG. 5B). Based on mathematical modeling, the sensitivity of the MDA-MB cells for the nano-tetrac effect on probability of successful replication was considerably higher than that for the effect on rate of growth, while the capacity was similar for both effects (see Table 1, supra).

Figure 5C:
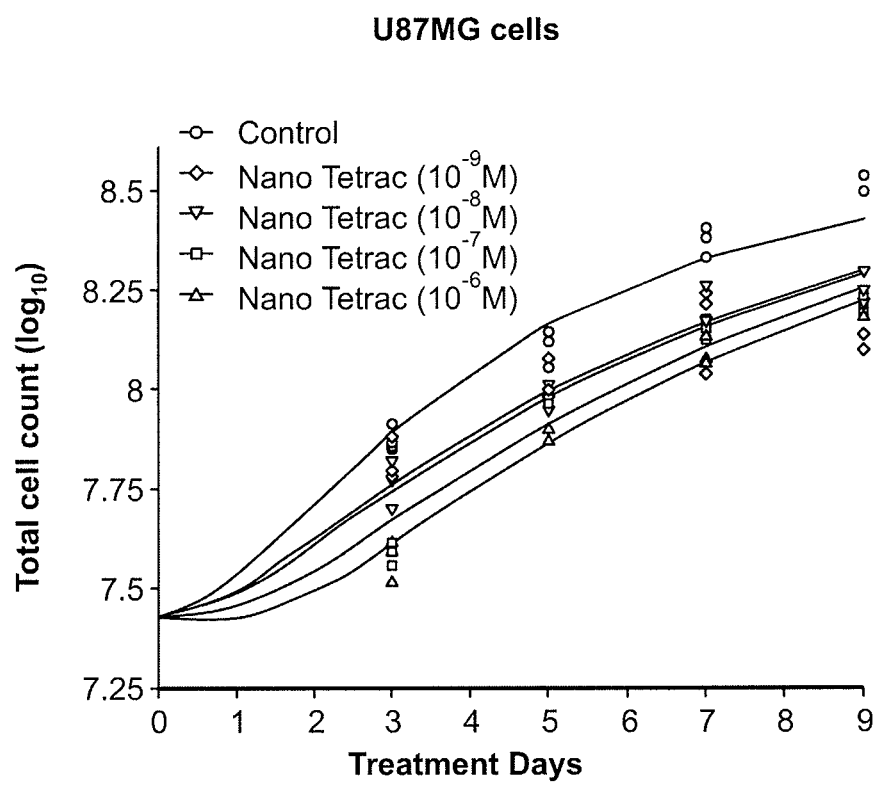
In FIG. 5C, U87MG cells were treated daily with different concentrations of tetrac or nano-tetrac ($10^{-9}$ to $10^{-6}$ M). Cells were harvested at the time points indicated. Total cell numbers taken after each treatment were used as indicators of tetrac or nano-tetrac-induced anti-proliferation.

Studies of nano-tetrac-induced antiproliferation were also conducted in U87MG cells and results indicate that the anti-proliferative effect of nano-tetrac was concentration-dependent. Concentrations of the nanoparticulate as low as $10^{-9}$ M reduced cell number by 36% (control vs. $10^{-9}$ M nano-tetrac=$1.641 \times 10^8$ vs. $2.264 \times 10^8$) after 7 d of treatment. (See FIG. 5C). Modeling suggested a higher sensitivity (lower IC50) for the effect on replication and a higher capacity for the effect on rate of growth (see, Table 1, supra). Both IC50k and IC50R were lower for nano-tetrac than for unmodified tetrac in U87MG cells indicating a higher sensitivity to nano-tetrac (see, Table 1, supra). For both MDA-MB cells and U87MG cells, the model assumes a decrease in ImaxR over time and a lag-time of growth during the first two days.

Tetrac and Nano-Tetrac Inhibit Thyroid Hormone-Induced Proliferation of Human Adenoid Cystic Carcinoma Cells.

Human adenoid cystic carcinoma TGS112T cells were cultured in medium that contained 0.25% hormone-stripped serum for 2 d and then treated with $10^{-7}$ M tetrac or nano-tetrac for 30 min prior institution of $10^{-7}$ M $T_4$ treatment for 24 h. Nuclear proteins were separated by SDS-PAGE followed by western blot analysis with proliferating-cell nuclear antigen (PCNA) antibody. Thyroid hormone-induced PCNA accumulation was inhibited by tetrac. (See FIG. 6A). Proliferation of TGS112T cells was stimulated by $10^{-7}$ M $T_4$, while tetrac at the same concentration had little effect alone, but blocked the $T_4$ effect. (See FIG. 6A). Inhibition of thyroid hormone-induced proliferation was confirmed by inhibition by tetrac and nano-tetrac of thyroid hormone-induced accumulation and [$^3$H]-thymidine incorporation. (See FIG. 6B). In studies of thymidine incorporation in the same cell line, nano-tetrac alone reduced baseline thymidine incorporation, and reduced $T_4$-induced thymidine incorporation by more than 14-fold that of tetrac (70-fold reduction vs. 5-fold reduction). (See FIG. 6B). On the other hand, although tetrac inhibited thyroxine-induced thymidine incorporation, unmodified tetrac when added alone stimulated thymidine incorporation (see FIG. 6B) to a limited degree in this relatively brief study. The effect of nano-tetrac and tetrac on cell proliferation was examined by counting TGS112T cells which were treated daily with $10^{-6}$ M tetrac or $10^{-6}$ M nano-tetrac. The decrease in cell count in the nano-tetrac-treated cells ($1.69 \times 10^8$ cells) after 7 d was 2-fold more than that of the tetrac-treated culture ($3.65 \times 10^8$ cells), compared to the untreated control cultures. (See FIG. 6C).

Role of Apoptosis in the Tetrac Effect on Cancer Cells.

Figure 7:
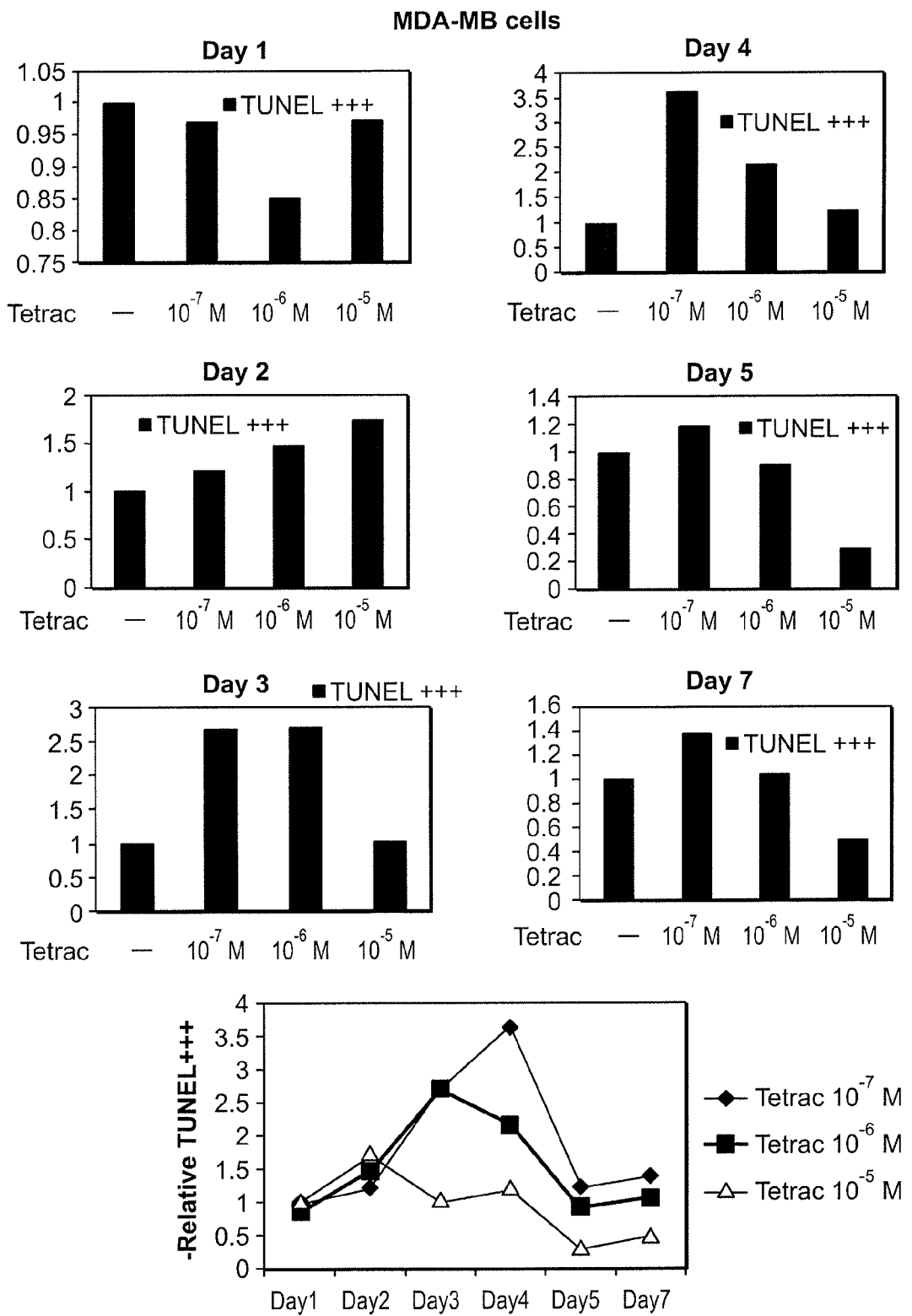
FIG. 7 is a series of graphs showing that tetrac induces apoptosis in MDA-MB cells. MDA-MB cells grown in perfusion bellows cell culture were treated with different concentrations of tetrac ($10^{-7}$ M to $10^{-5}$ M) daily. Cells were harvested on the day indicated. Two million cells of each sample were prepared for flow cytometry. Flow cytometry was conducted as described in Example 1, infra.

Cells were harvested for FACS analysis 1-5 d after treatment with $10^{-7}$ to $10^{-5}$ M tetrac. There was a 10-fold increase of apoptotic cells with $10^{-5}$ M tetrac treatment as compared to untreated control cells at 1 d and 10-7 M and 10-6 M tetrac also induced apoptosis. (See FIG. 7). By day 2, tetrac, $10^{-7}$ M and $10^{-6}$ M, induced apoptosis by 2.5-fold as compared to untreated control. Similar results were obtained after 4 d of treatment of tetrac. That is, cells treated with $10^{-7}$ M tetrac showed highest proportion of apoptotic cells. (See FIG. 7). These results raise the possibility that there are two dose-dependent types of tetrac-induced apoptosis: one is induced transiently by $10^{-5}$ M tetrac and the other is induced by $10^{-6}$ and $10^{-7}$ M tetrac.

Figure 8:
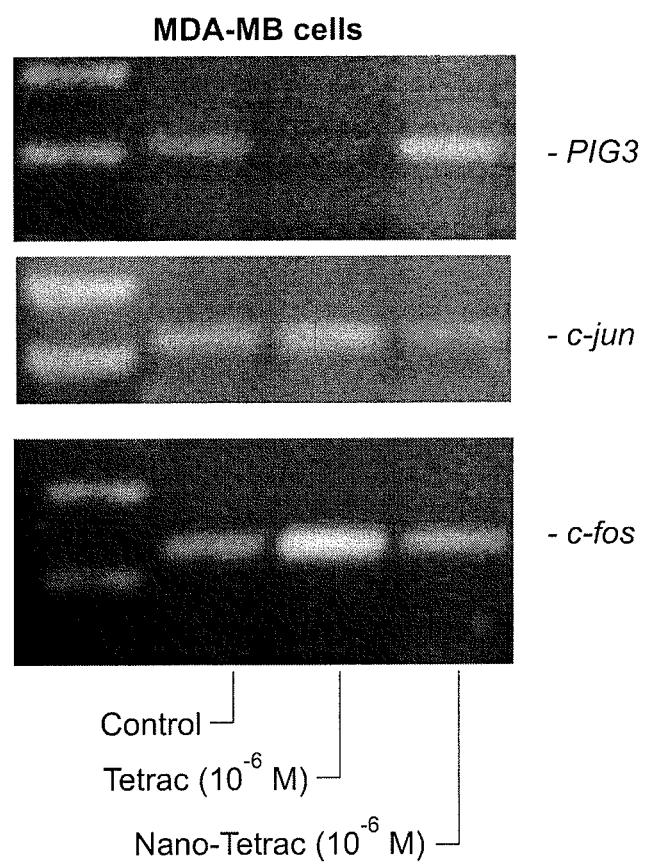
FIG. 8 shows the expression of pro-apoptotic genes by tetrac and nano-tetrac. MDA-MB cells were treated daily with $10^{-6}$M of tetrac or nano-tetrac in bellows perfusion culture system. Cells were harvested after 3 days of treatment and total RNA was extracted. RT-PCR was conducted as described in Example 1, infra.

The pro-apoptotic gene expression in tetrac- and nano-tetrac-treated MDA-MB cells and U87MG cells was also examined. RNA was extracted from cells harvested from the perfusion bellows cell culture system at the end of treatment. Primers for PIG3, c-jun and c-fos were constructed for RT-PCR studies. Treatment of cells for 1 day with tetrac ($10^{-6}$ M) increased expression of c-fos and c-jun. (See FIG. 8). Nano-tetrac increased expression of PIG3, c-fos and c-jun. (See FIG. 8).

Effects of Tetrac and Nano-Tetrac on Non-Malignant Cells.

In order to confirm that tetrac and nano-tetrac only suppress cell proliferation in cancer cells, tetrac and nano-tetrac were also examined for potential anti-proliferative effects on immortalized non-malignant cells, using monkey kidney epithelial CV-1 cells and human embryonic kidney 293T cells. The cells were treated daily with either $10^{-6}$ M tetrac or $10^{-6}$ M nano-tetrac for 7 days, then were harvested, counted and examined microscopically. There was no significant change in either cell numbers (see FIG. 9) or in morphology comparing the untreated control cells and those treated with either tetrac or nano-tetrac. These results suggest that nano-tetrac and tetrac only affect malignant cell proliferation and not that of non-neoplastic cells.

Tetrac Potentiates Cetuximab-Induced Apoptosis in Human Breast Cancer Cells.

The EGFR antibody, cetuximab, has been used in clinical trials either alone or combination with other anti-cancer drug. Cetuximab inhibits binding of the endogenous ligand for the receptor (EGF) and decreases cell motility, invasiveness and metastasis and also promotes apoptosis. (See Kalofonos et al., 2006. Curr. Top. Med. Chem. 6:1687-1705 (incorporated herein by reference)). Combining cetuximab with various chemotherapeutic agents has revealed additive or potentiated growth inhibition in various cancer cell lines, such as those from colon, head and neck, breast, kidney and bladder. (See Balin-Gauthier et al., 2006. Cancer Chemother. Pharmacol. 57:709-718; Martens et al., 2008. Clin. Cancer Res. 14:5447-5458). Approved for clinical use against head-and-neck and colorectal cancers, cetuximab has recently been shown to be effective against invasive glioblastoma xenografts in the mouse. (See Prichard et al., 2007. Laryngoscope. 117:674-679).

In order to examine whether tetrac or nano-tetrac potentiate cetuximab-induced anti-proliferation, MDA-MB cells were treated with cetuximab (0.1 µg/ml) in the presence or absence of $10^{-7}$ M tetrac. Both agents suppressed cell proliferation in MDA-MB cells. (See FIG. 10). The inhibitory effects on cell growth of cetuximab and tetrac after 8 d treatment were 34% and 38%, respectively. The combination of tetrac and cetuximab reduced total cell number by up to 63%. These results suggest that the combination of tetrac and cetuximab may increase efficacy of cancer chemotherapy when compared to effects of either drug alone.

Example 2

Anti-Proliferative Effects of Erbitux® (Cetuximab) and Tetrac Nanoparticles on Colon Cancer Cells Using the bellows perfusion cell culture system shown in FIG. 1, the effects of tetrac nanoparticles (NP-Tetrac) plus cetuximab on proliferation of colon cancer cells in the flasks were examined.

Effects of NP-Tetrac Plus Cetuximab on Proliferation of Colon Cancer Cells.

Figure 11:
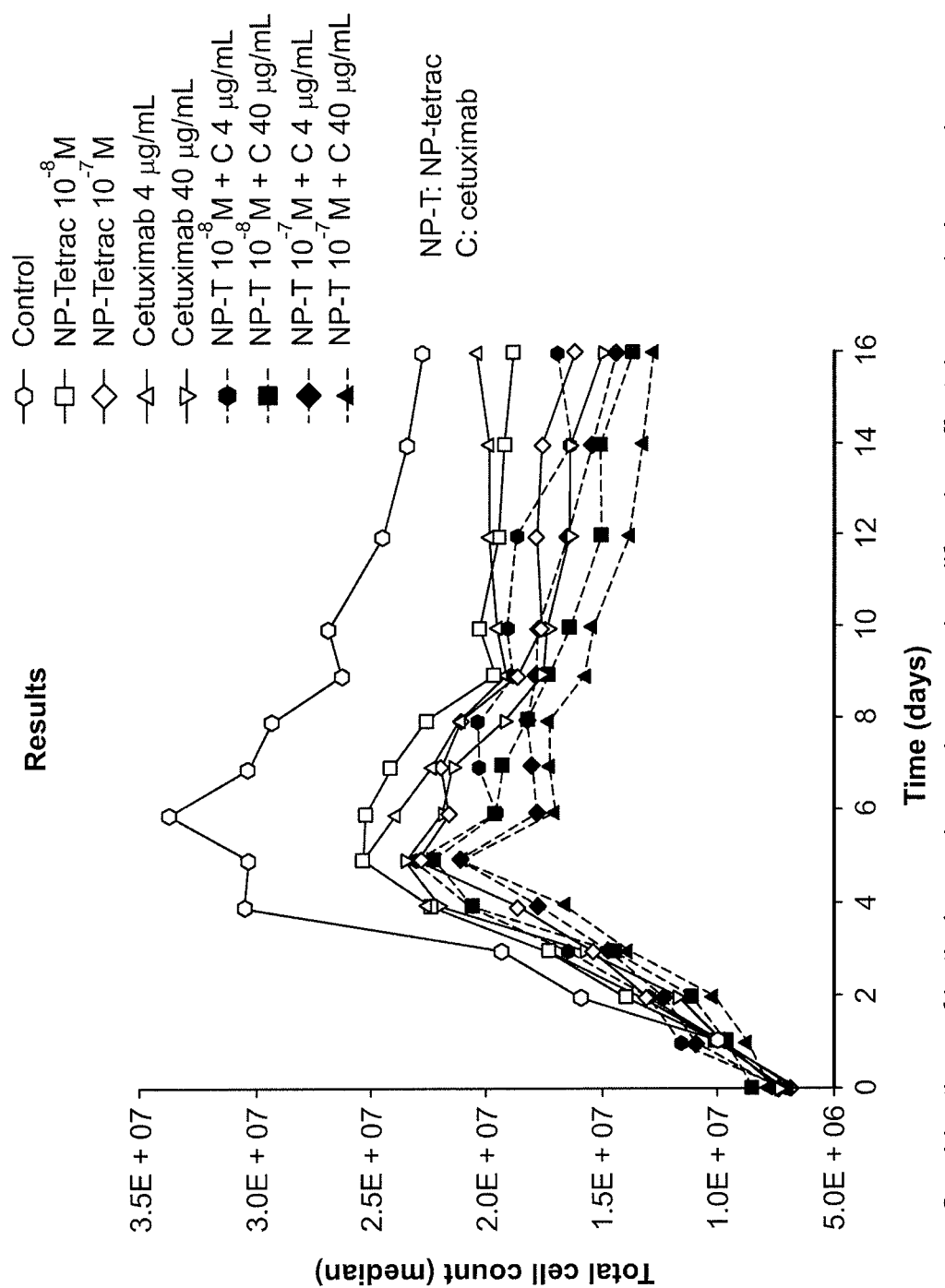
FIG. 11 is a graph showing that the combination of cetuximab and nano-tetrac shows a larger anti-proliferative effect than either drug on its own in colon carcinoma cells.
Figure 12A:
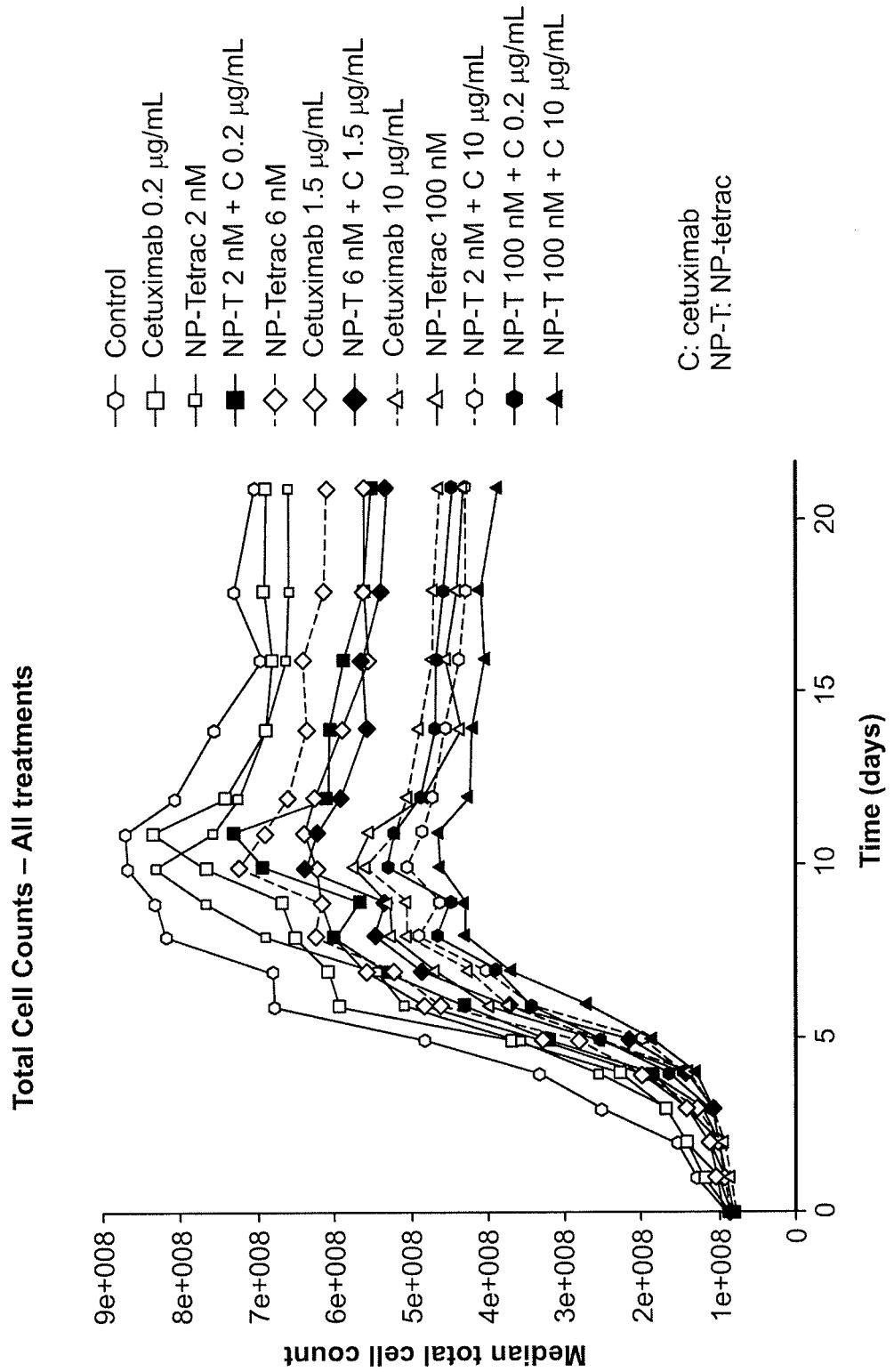
FIG. 12A is a graph showing the total cell counts different concentrations of cetuximab, nano-tetrac, and the combination of cetuximab and nano-tetrac on K-ras mutant colon carcinoma cells.
Figure 12B:
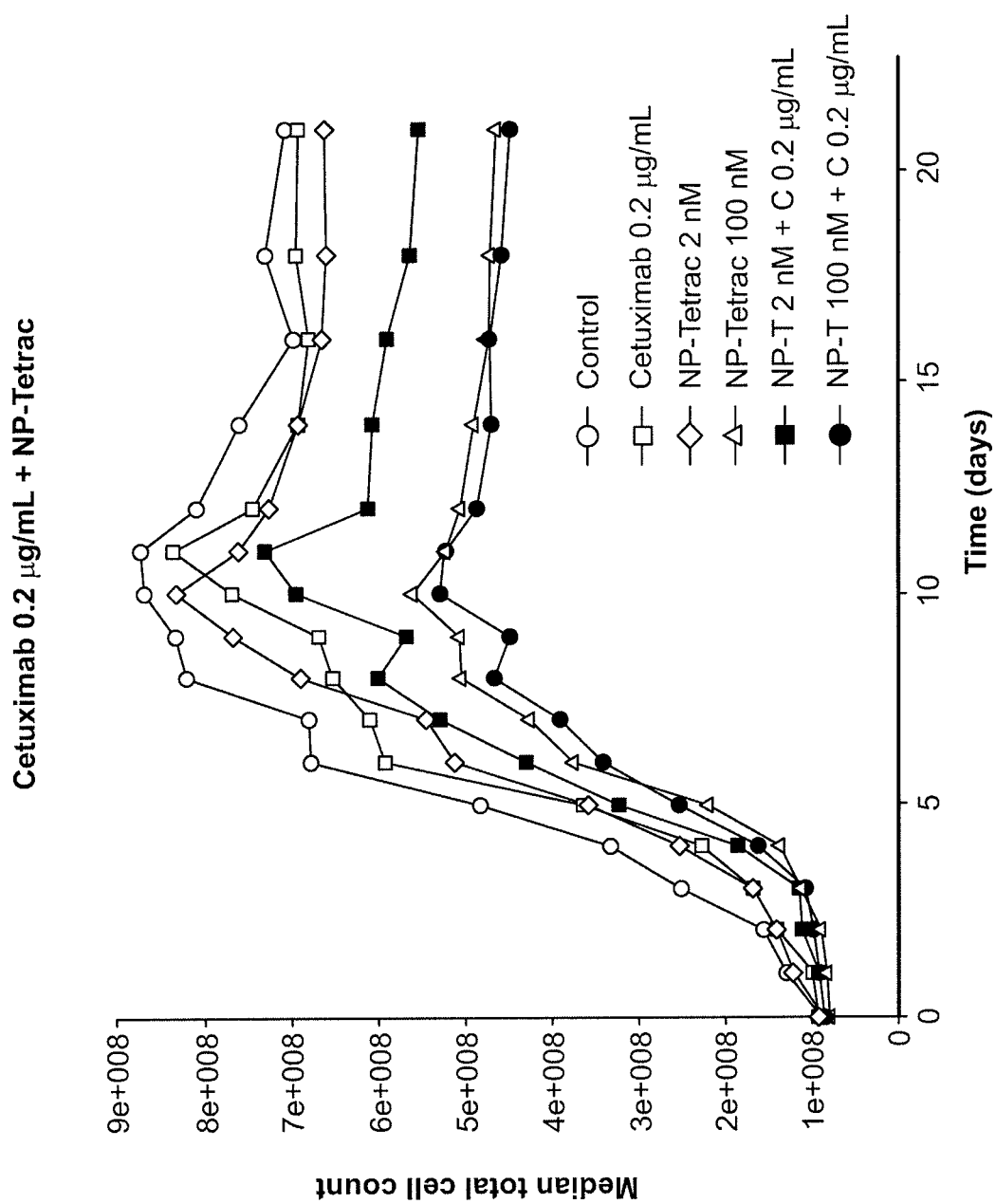
FIG. 12B is a graph showing the total cell counts for 0.2 µg/mL cetuximab plus nano-tetrac in varying concentrations.
Figure 12C:
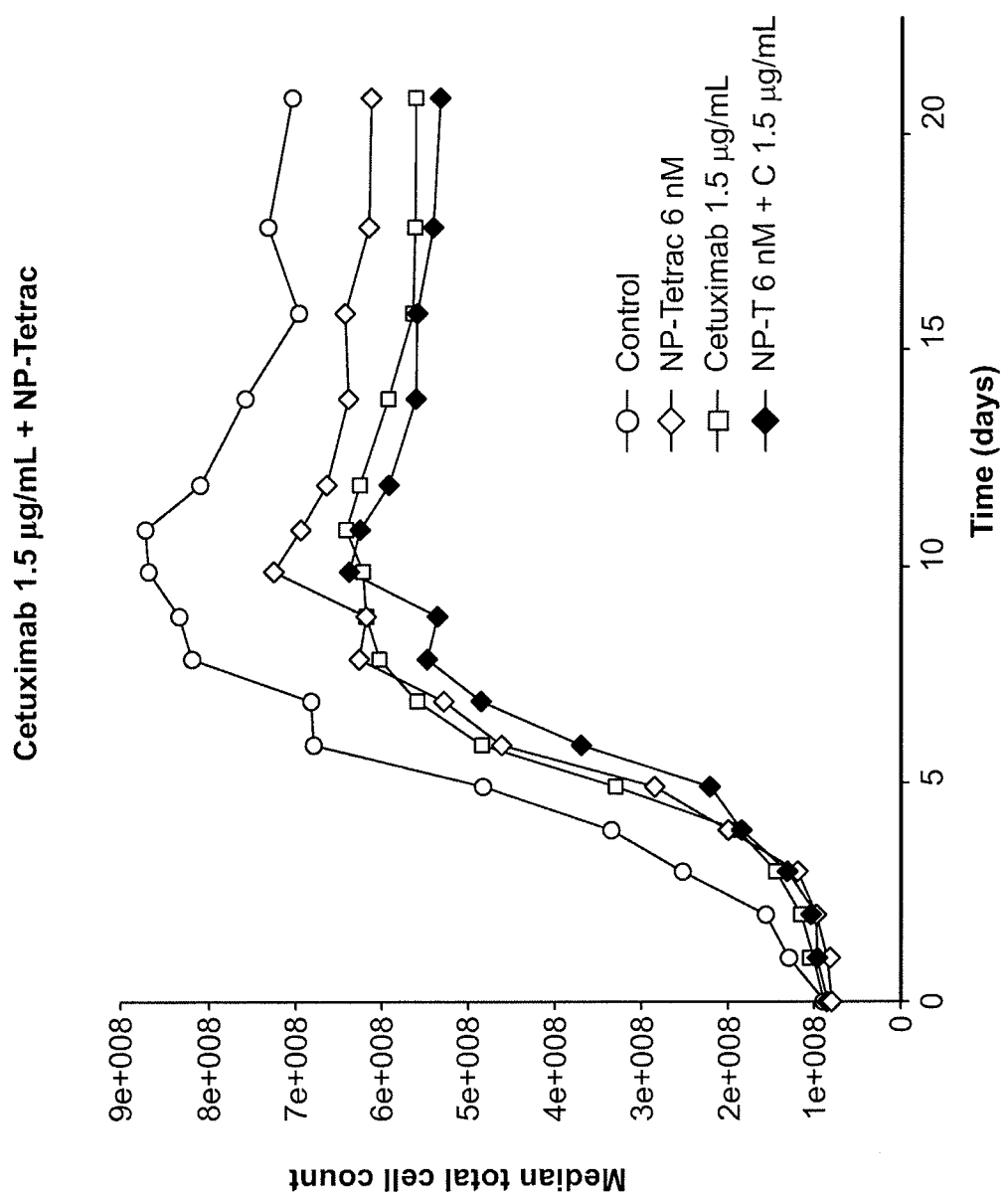
FIG. 12C is a graph showing the total cell counts for 1.5 µg/mL cetuximab plus 6 nM nano-tetrac.
Figure 12D:
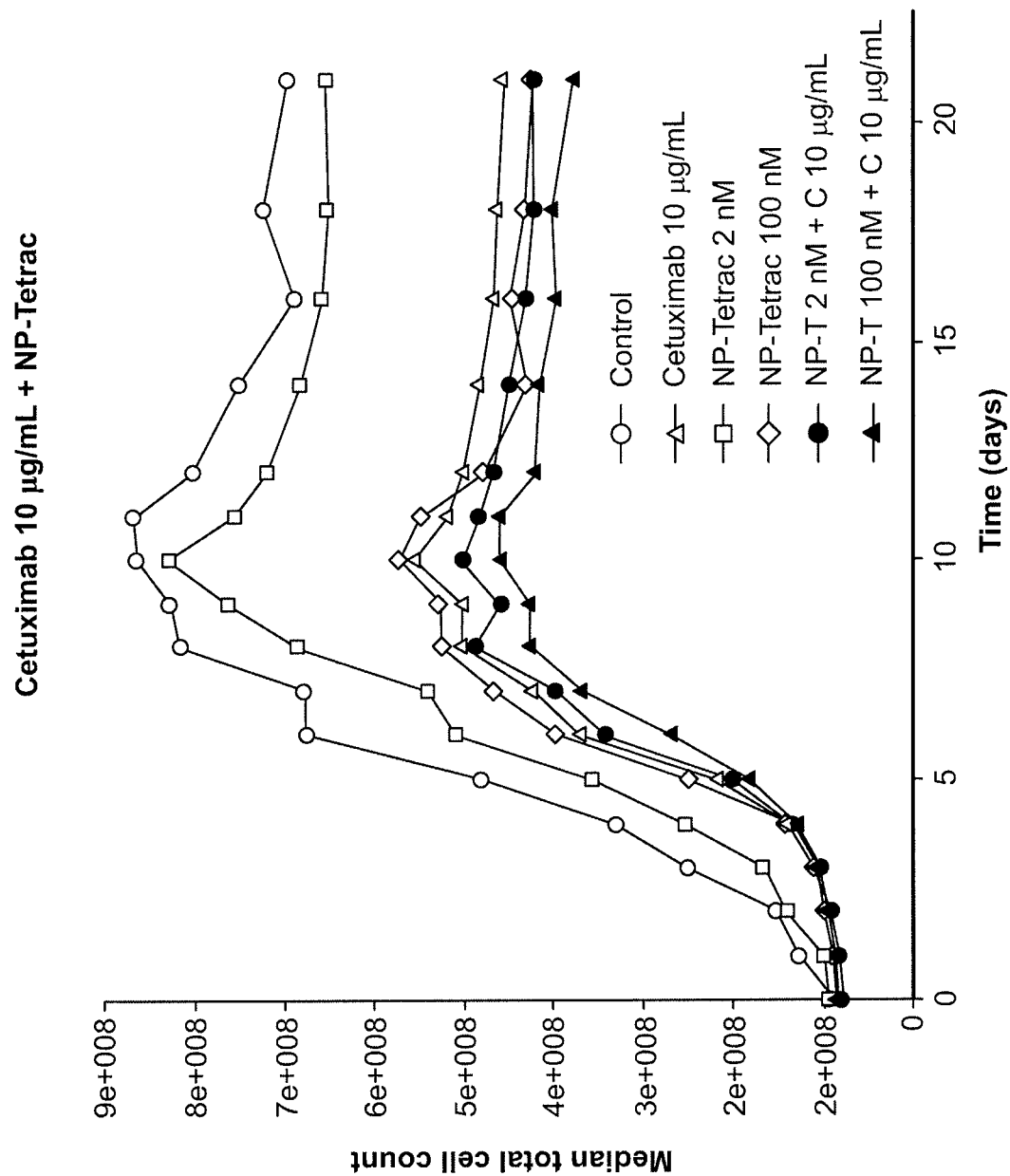
FIG. 12D is a graph showing the total cell counts for 10 µg/mL cetuximab plus varying concentrations of nano-tetrac.

Cells were grown on specially treated flakes in cell culture flasks. The cell culture medium contained 10% fetal bovine serum and various concentrations of cetuximab and NP-Tetrac. The medium was refreshed every 24 hours. The results of these studies are shown in FIG. 11, which demonstrates that the combinations of both drugs showed a larger anti-proliferative effect than each drug on its own.

Effects of NP-Tetrac Plus Cetuximab on Proliferation of Colon Cancer Cells in the Bellows Perfusion System.

Figure 13:
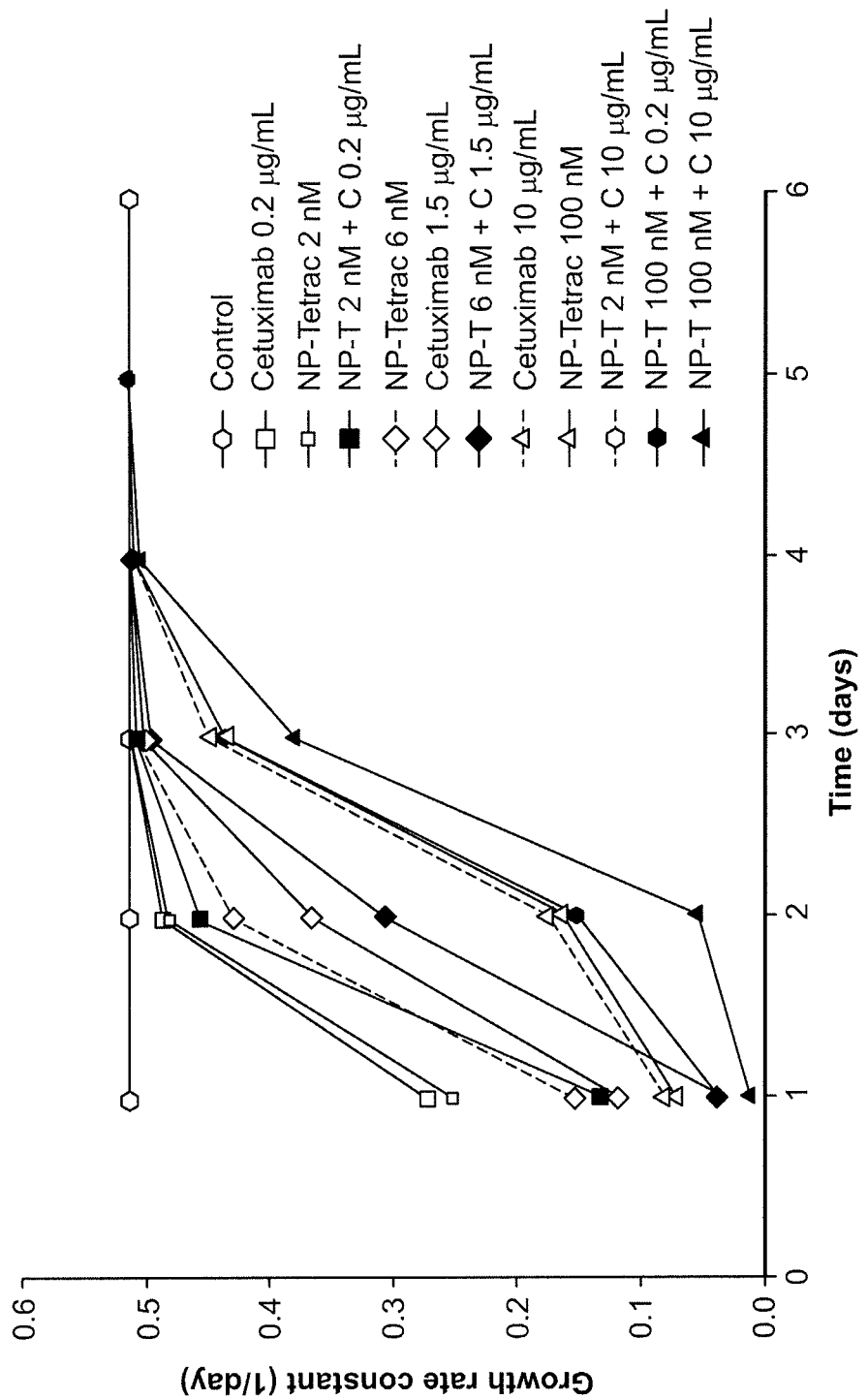
FIG. 13 is a graph showing the drug effect on growth rate constant from pharmacodynamic modeling for all treatments.

Cells were grown on specially treated flakes in the bellows perfusion cell culture system. The cell culture medium contained 10% fetal bovine serum and various constant concentrations of cetuximab and NP-Tetrac. The system was constantly perfused by fresh medium. The results are shown in FIGS. 12-13.

Results

Mathematical modeling (see FIG. 2B) suggests that the growth rate constant is decreased in a concentration-dependent manner during the first five days of treatment. Additional effects might be present but likely were not large enough to be identified in this model. The model shown in FIG. 2B, which assumes independent pathways of action for the two drugs (NP-Tetrac and cetuximab) provided adequate fits to the data.

The parameter estimates used herein are as follows:
Cetuximab: $I_{max}$ 0.86, $IC_{50}$ 0.01 µg/mL
NP-Tetrac: $I_{max}$ 0.87, $IC_{50}$ 0.08 nM Effects of NP-Tetrac Plus Cetuximab on Proliferation and Viability of K-Ras Mutant (HCT116) Cells.

Approximately 50% of colon cancer patients in a clinical trial showed resistance to cetuximab. (See Jonker et al., 2007. N Engl J Med 357:2040-48). HCT116 cells, a fast growing a malignant cancer cell, have a mutation in the K-ras protooncogene and are resistant to cetuximab.

Figure 14A:
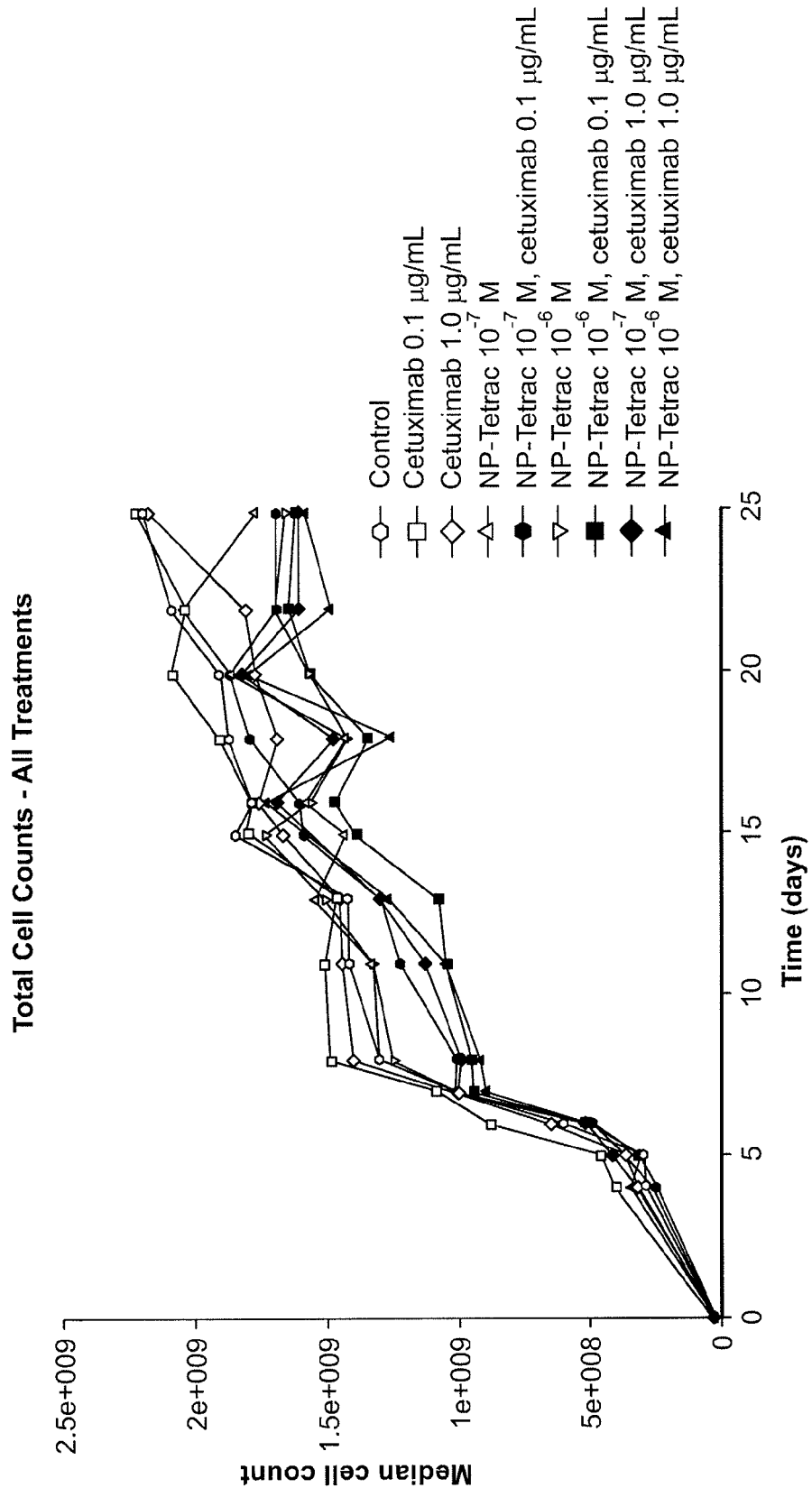
FIGS. 14A and 14B are graphs showing the effects of cetuximab or nano-tetrac individually, or in combination at varying concentrations on total cell counts for HCT116 cells.
Figure 14B:
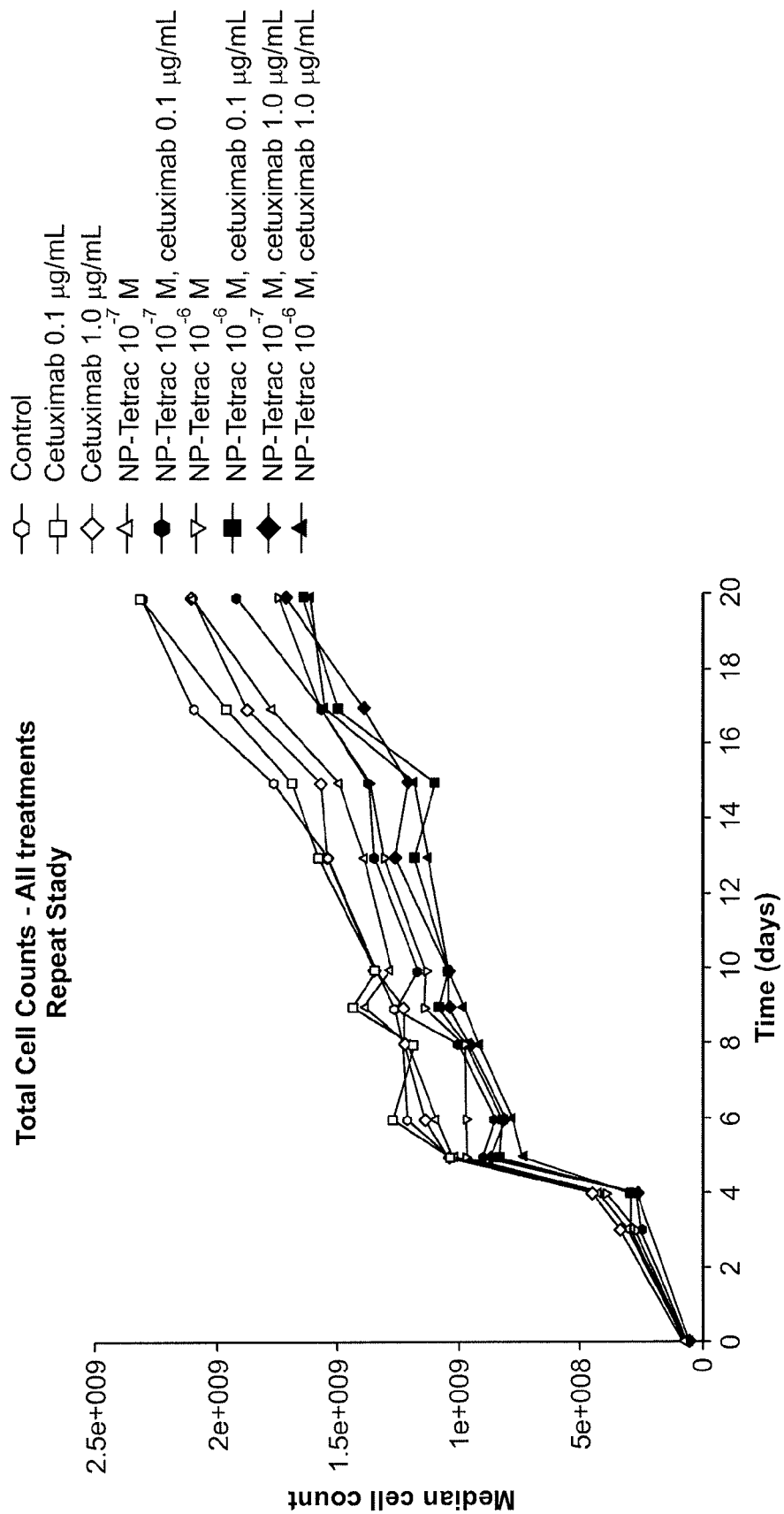

In the experiments described herein, cells were treated with constant concentration of drugs. Cetuximab alone did not show a large effect. In one experiment, between days 12 and 18, the $10^{-6}$ M NP-Tetrac+0.1 µg/mL cetuximab appeared to have a larger effect on cell counts than $10^{-6}$ M NP-Tetrac+1.0 µg/mL cetuximab. In another experiment, between days 10 and 20, $10^{-6}$ M NP-Tetrac+0.1 µg/mL cetuximab appeared to have a similar effect on cell counts as $10^{-6}$ M NP-Tetrac+1.0 µg/mL cetuximab. (See FIGS. 14A and 14B).

Figure 15B:
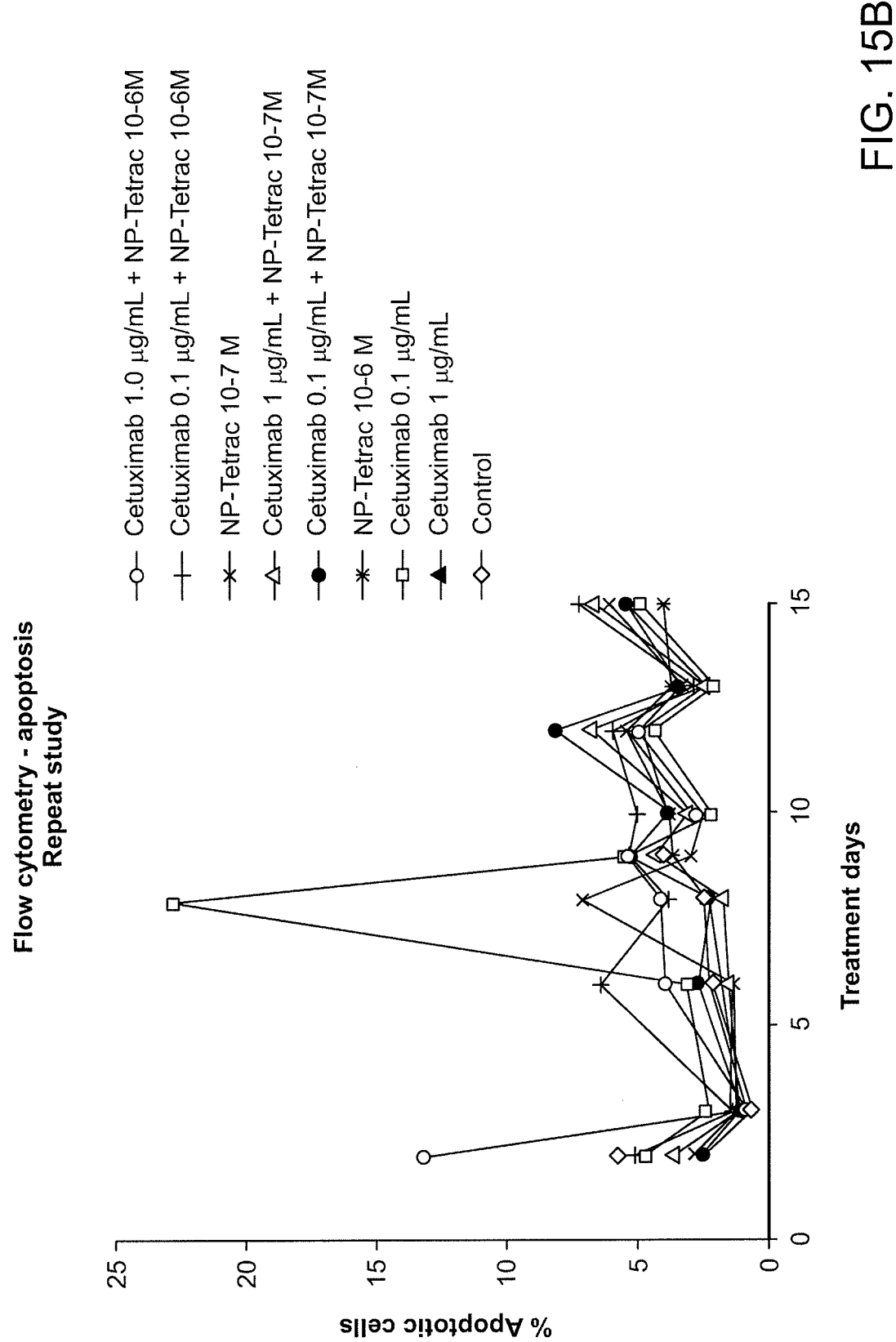
Figure 16A:
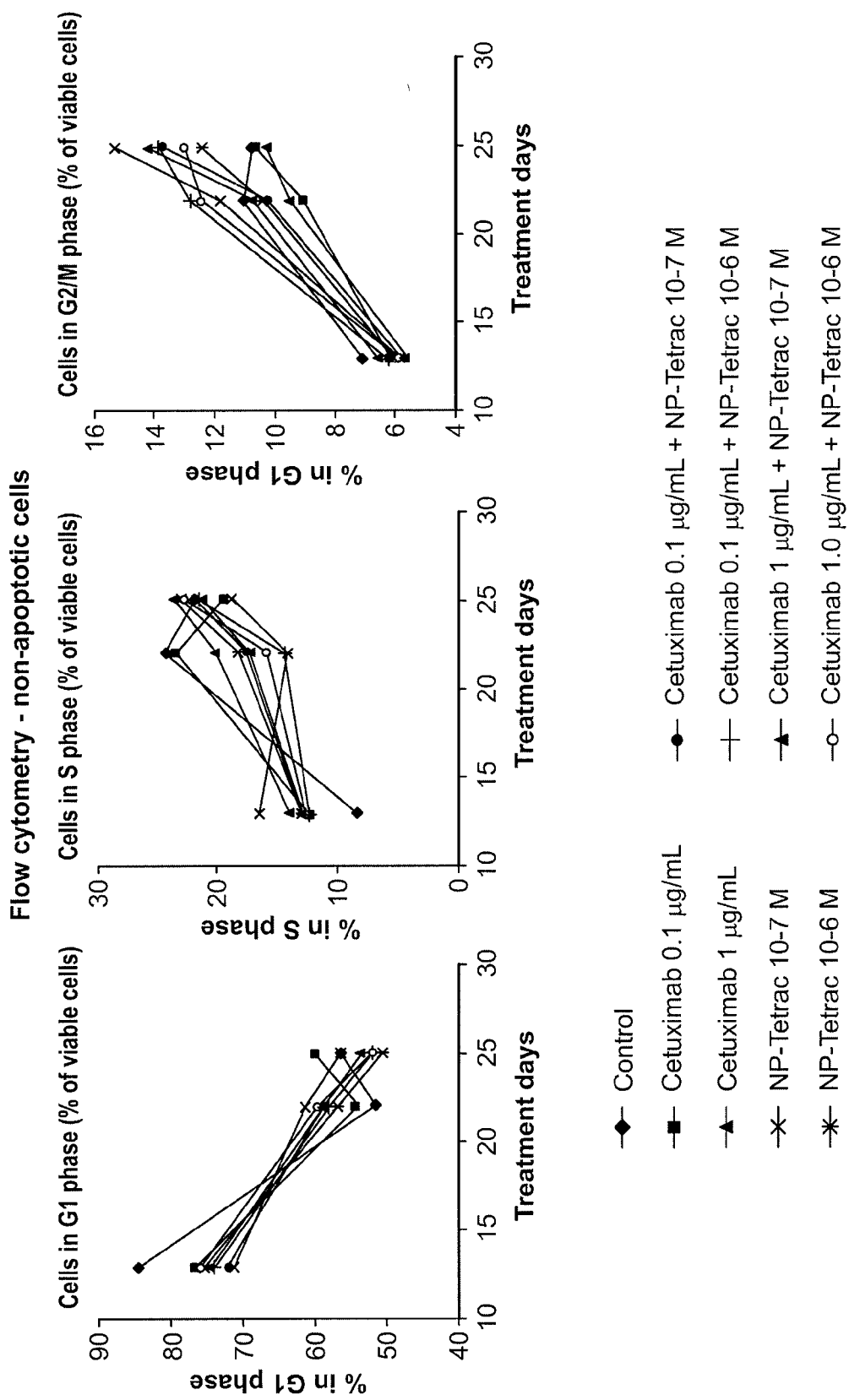
FIGS. 16A and 16B are a series of graphs showing the results of flow cytometry experiments for non-apoptotic cells.
Figure 16B:
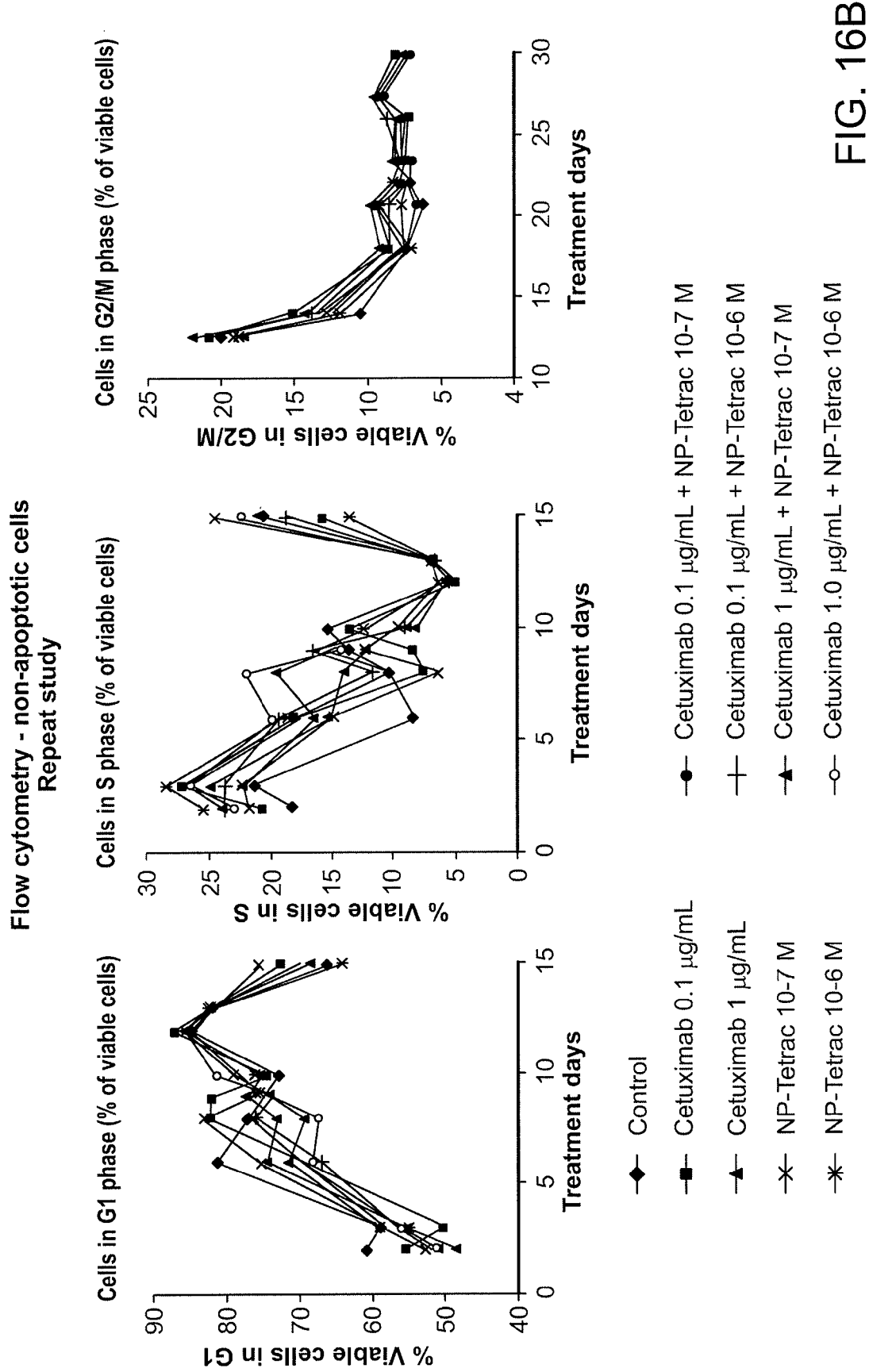

FIGS. 15A-C show the results of flow cytometry experiments on apoptosis following treatment with cetuximab, NP-Tetrac, or a combination. Cells in S phase were most sensitive to apoptosis. FIGS. 16A-B shows the results of flow cytometry experiments on non-apoptotic cells following treatment with cetuximab, NP-Tetrac, or a combination thereof.

Results

These results show that the combined treatment with NP-Tetrac and cetuximab had a larger anti-proliferative effect on K-ms mutant cancer cells than cetuximab alone. A model assuming that both drugs act by separate pathways on success of replication adequately described the total cell counts from all treatments simultaneously.

The parameter estimates used herein are as follows:
Cetuximab: $I_{max}$ 0.011, $IC_{50}$ 1.72 µg/mL
NP-Tetrac: $I_{max}$ 0.053, $IC_{50}$ 0.104×$10^{-6}$ M The fraction of apoptotic cells was increased by up to a factor of 5 with the combination treatment versus treatment with cetuximab alone.

CONCLUSION

Accordingly, based on the results presented herein, combined treatment with NP-Tetrac and cetuximab has a larger anti-proliferative effect on cancer cells than treatment with cetuximab alone. Moreover, NP-Tetrac induces apoptosis in cetuximab-resistant K-ms mutant colon cancer cells.

In combination with PD modeling, the use of the perfusion bellows cell culture system allows one to study the dose-response relationship of anti-neoplastic agents over a wide concentration rang in vitro, and can support translation from in vitro to animal models and human clinical trials.

The addition of a cytotoxic drug after pretreatment with NP-Tetrac and cetuximab may also be promising in the treatment of cancer.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A pharmaceutical composition comprising a combination of cetuximab and an anti-angiogenic thyroid hormone analog selected from the group consisting of tetrac (tetraiodothyroacetic acid), triac (triiodothyroacetic acid) and a combination thereof, wherein the thyroid hormone analog is conjugated via a covalent bond to a polymer, wherein the cetuximab is at least one of encapsulated within said polymer, conjugated via a covalent bond to the polymer and a combination thereof.

2. The pharmaceutical composition of claim 1, wherein the polymer is selected from polyvinyl alcohol, acrylic acid ethylene copolymer, methoxypolyethylene, polyethyleneglycol (PEG), polyacrylic acid, polylactic acid, agarose, polyglycolide, polylactide, PEO, m-PEG, PVA, PLLA, PGA, poly-L-Lysine, Human Serum Albumin, cellulose derivatives, carbomethoxy/ethyl/hydroxypropyl, hyaluronic acid, folate linked cyclodextrin/dextran, sarcosine/amino acid spaced polymer, alginate, carrageenan, pectin/chitosan, chitosan, dextran, collagen, polyamine, poly aniline, poly alanine, polytrytophan, poly tyrosine, polylactide-co-glycolide (PLG), poly(lactic-co-glycolic) acid (PLGA), polyglycolide, polylysyl glycolide, polylactic acid, or co-polymers thereof, wherein said polymer is formulated into a nanoparticle, wherein said nanoparticle is between 150 and 250 nanometers in size, -and wherein said tetrac binds to the cell surface receptor for thyroid hormone on integrin $\alpha v \beta 3$.

3. The pharmaceutical composition of claim 2, wherein the thyroid hormone analog is attached to the nanoparticle via a linker.

4. The pharmaceutical composition of claim 3, wherein the linker is between 4 and 15 atoms long.

5. The pharmaceutical composition of claim 1, further comprising an anti-estrogen compound.

6. The pharmaceutical composition of claim 5, wherein the anti-estrogen compound is selected from the group consisting of tamoxifen and aromatase inhibitors.

7. The pharmaceutical composition of claim 2, wherein the nanoparticles further comprise one or more additional chemotherapeutic agents.

8. The pharmaceutical composition of claim 7, wherein the one or more additional chemotherapeutic agents are targeted to the cancer cells.

9. The pharmaceutical composition of claim 1, wherein the combination inhibits PI3K-dependent HIF1α gene expression.

10. The pharmaceutical composition of claim 9, wherein the combination blocks the inhibitory action of endogenous thyroid hormone on the actions of cetuximab on HIF1α.

11. A method of treating cancer wherein the cancer is selected from the group consisting of colon cancer, breast cancer, glioblastoma, and adenoid cystic carcinoma, comprising administering a therapeutically effective amount of a combination of the pharmaceutical composition of claim 1 to a patient suffering therefrom.

12. The method of claim 11, wherein the thyroid hormone analog is tetrac.

13. The method of claim 12, wherein tetrac is conjugated via a covalent bond to a polymer selected from polyvinyl alcohol, acrylic acid ethylene co-polymer, methoxypolyethylene, polyethyleneglycol (PEO), polyacrylic acid, poly lactic acid, agarose, polyglycolide, polylactide, PEO, m-PEG, PVA, PLLA, POA, poly-L-lysine, Human Serum Albumin, cellulose derivatives, carbomethoxy/ethyl/hydroxypropyl, hyaluronic acid, folate linked cyclodextrin/dextran, sarcosine/amino acid spaced polymer, alginate, carrageenan, pectin/chitosan, chitosan, dextran, collagen, polyamine, poly aniline, poly alanine, polytrytophan, poly tyrosine, polylactide-co-glycolide (PLG), poly(lactic-co-glycolic) acid (PLGA), polylysyl glycolide, polylactic acid, polyglycolide, or co-polymers thereof, wherein said polymer is formulated into a nanoparticle, wherein said nanoparticle is between 150 and 250 nanometers in size, and wherein said tetrac binds to the cell surface receptor for thyroid hormone on integrin $\alpha v \beta 3$.

14. The method of claim 11, further comprising administering an anti-estrogen compound to the subject.

15. The method of claim 14, wherein the anti-estrogen compound is selected from the group consisting of tamoxifen and aromatase inhibitors.

16. The method of claim 13, wherein the nanoparticles further comprise one or more additional chemotherapeutic agents.

17. The method of claim 13, wherein cetuximab is encapsulated within the nanoparticle.

18. The pharmaceutical composition of claim 2, wherein the tetrac is a plasma membrane impermeable form of tetrac, wherein said nanoparticle is a non-reactive nanoparticle which is covalently bound to an outer ring hydroxyl group of the tetrac.

19. The pharmaceutical composition of claim 18 wherein the non-reactive nanoparticle is covalently bonded via a linker.

20. The pharmaceutical composition of claim 18 wherein the linker is between 4-15 atoms long.

21. A pharmaceutical composition comprising a combination of cetuximab and a thyroid hormone analog selected from the group consisting of tetraiodothyroacetic acid (tetrac), triiodothyroacetic acid (triac) and combinations thereof, wherein the cetuximab and the thyroid hormone analog are conjugated to a polymer wherein the polymer is a nanoparticle.

* * * * *

UNITED STATES PATENT AND TRADEMARK OFFICE
CERTIFICATE OF CORRECTION

PATENT NO. : 9,180,107 B2
APPLICATION NO. : 12/751375
DATED : November 10, 2015
INVENTOR(S) : Hung-Yun Lin et al.

It is certified that error appears in the above-identified patent and that said Letters Patent is hereby corrected as shown below:

<u>ON THE TITLE PAGE, ITEM 56</u>

References Cited/Other Publications, "αv" was incorrectly cited as "a□" and "αvβ3" was incorrectly cited as "a□β3". They are correct in the Specifications and Claims sections of the Patent.

Other Publications (pages 2 through 9), there are numerous typos in the cites of the publications. The typo in each reference has been corrected and underlined.

<u>Page 2</u>:
Davis et al. (2006), "Cell-<u>surface</u> receptor for thyroid hormone and tumor cell proliferation", Expert Reviews in <u>Endocrinology</u> and Metabolism, 1(6):753-761.

<u>Page 3</u>:
Kleczkowska et al., "<u>Differential</u> poly(ADP-ribose) metabolism in repair-proficient and repair-deficient murine lymphoma cells", Mut. Res., 235:93-99 (1990) 7 pages.

Lawler et al., "Cell Attachment to <u>Thrombospondin</u>: The Role of ARG-GLY-ASP, Calcium and Integrin Receptors", J. Cell Biol., 107(6 Pt. 1):2351-2361 (1988) 11 pages.

Letterio et al., "Maternal Rescue of Transforming Growth <u>Factor</u>-β1 Null Mice", Science, 264:1936-1938 (1994) 4 pages.

<u>Page 4</u>:
Mishkin et al., "Increased Survival of Rats Bearing Morris Hepatoma 7800 after Induction of <u>Hypothyroidism</u>", Cancer Res., 39:2371-2375 (1979) 5 pages.

Mousa, S.A., "Mechanisms of Angiogenesis: Potential Therapeutic Targets", in Angiogenesis <u>Inhibitors</u> and Stimulators: Potential Therapeutic Implications, Landes Bioscience, Georgetown, Texas, Chapter I, pp. 1-12 (2000) 14 pages.

Signed and Sealed this
Twelfth Day of April, 2016

Michelle K. Lee
*Director of the United States Patent and Trademark Office*

CERTIFICATE OF CORRECTION (continued)

U.S. Pat. No. 9,180,107 B2

ON THE TITLE PAGE, ITEM 56

Nehls et al., "A Novel Microcarrier-Based in Vitro Assay for Rapid and Reliable Quantification of Three-Dimensional Cell Migration and Angiogenesis", Microvasc. Res., 50(3):311-322 (1995) 12 pages.

Page 5:
Pujol et al., "Letter to the editors: Prevention of thyroid neoplasm recurrence with Triac and levothyroxine", Clin. Endocrinol., 46(1):121-122 (1997) 2 pages.

Scanlan et al., "Selective Thyromimetics: Tissue-selective thyroid hormone analogs", Curr. Opin. Drag Discov. Dev., 4(5):614-622 (2001) 9 pages.

Schreiber et al., "Hormone delivery systems to the brain-transthyretin", Exp. Clin. Endocrinol. Diabetes, 103(2):75-80 (1995) 7 pages.

Tomanek et al., "Early Coronary Angiogenesis in Response to Thyroxine: Growth Characteristics and Upregulation of Basic Fibroblast Growth Factor", Circ. Res., 82(5):587-593(1998) 8 pages.

Page 6:
Wang et al., "Integrin-associated Protein Stimulates α2β1-dependent Chemotaxis via Gi-mediated inhibition of Adenylate Cyclase and Extracellular-regulated Kinasis", J. Cell. Biol., 147:389-399 (1999) 11 pages.

Zhen et al., "Synthesis and Amyloid Binding Properties of Rhenium Complexes: Preliminary Progress Toward a Reagent for SPECT Imaging of Alzheimer's Disease Brain", J. Med. Chem., 42:2805-2815 (1999) 11 pages.

Amirkhosravi et al., "Antimetastatic effect of tinzaparin, a low-molecular-weight heparin", J. Thromb. Haemost, 1:1972-1976 (2003) 5 pages.

Page 7:
Gladson, C.L., "Expression of integrin αvβ3 in Small Blood Vessels of Glioblastoma Tumors", J. Neuropath. Exp. Neurol., 55(11):1143-1149 (1996) 7 pages.

Glinsky et al., "Gene expression profiling predicts clinical outcome of prostate cancer", J. Clin. Invest., 113(6):913-923 (2004) 11 pages.

Goldstein et al., "Influence of Lesion Size and Location on Amphetamine-Facilitated Recovery of Beam-Walking in Rats", Behav. Neurosci., 104(2):320-327 (1990) 9 pages.

Grant, D.B., "Monitoring TSH concentrations during treatment for congenital hypothyroidism", Arch. Disease Childhood, 66:669-670 (1991) 2 pages.

CERTIFICATE OF CORRECTION (continued)
U.S. Pat. No. 9,180,107 B2

ON THE TITLE PAGE, ITEM 56

Hansebout, R.R., "A Comprehensive Review of Methods of Improving Cord Recovery After Acute Spinal Cord Injury" in Early Management of Acute Spinal Cord Injury, pp. 181-196 (1982) 16 pages.

Hercbergs et al., "GL261 brain tumor cells: responses to single or fractionated x-irradiation with the αvβ3 integrin tyroxine receptor antagonist tetrac (tetraiodothyroacetic acid)", 20th EORTC-NCI-AACR Symposium on Molecular Targets and Cancer Therapeutics, Geneva, Switzerland, Oct. 2008.

Hercbergs et al., "Propylthiouracil-induced Chemical Hypothyroidism with High-Dose Tamoxifen Prolongs Survival in Recurrent High Grade Glioma: A Phase I/II Study", Anticancer Res., 23:617-626 (2003) 10 pages.

Page 8:
Kim et al., "Regulation of Angiogenesis in Vivo, by Ligation of Integrin α5β1 with the Central Cell-Binding Domain of Fibronectin", Am. J. Pathol., 156(4):1345-1362 (2000) 18 pages.

Brooks et al., "Antiintegrin αvβ3 blocks human breast cancer growth and angiogenesis in human skin", J. Clin. Invest., 96(4):1815-1822 (1995) 8 pages.

Burgman et al., "Effect of Inhibitors of Poly(ADP-Ribose)Polymerase on the Radiation Response of HeLa S3 Cells", Radiat. Res., 119:380-386 (1989) 7 pages.

Chanoine et al., "The role of transthyretin in the transport of thyroid hormone to cerebrospinal fluid and brain", Acta Medica Austriaca, 19(Suppl. 1):25-28 (1992) 5 pages.

Charness et al., "Ethanol Increases the Expression of Functional Delta-Opioid Receptors in Neuroblastoma x Glioma NG108-15 Hybrid Cells", J. Biol. Chem., 261(7):3164-3169 (1986) 6 pages.

Cody et al., "Molecular modeling of the thyroid hormone interactions with αvβ3 integrin", Steroids, 72:165-170 (2007) 6 pages.

Page 9:
Ding et al., "Radioprotection of Hematopoietic Tissue by Fibroblast Growth Factors in Fractionated Radiation Experiments", Acta Oncol., 36(3):337-340 (1997) 4 pages.

SPECIFICATION

Column 6, Lines 55-67, the published formula is incorrect and must be replaced with the correct formula:

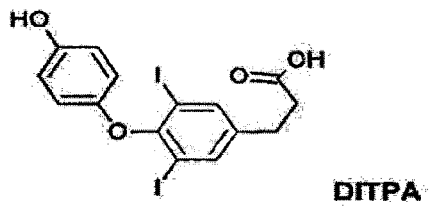

DITPA

SPECIFICATION
Column 7, Lines 1-13, the published formula is incorrect and must be replaced with the correct formula, as submitted on the Application:
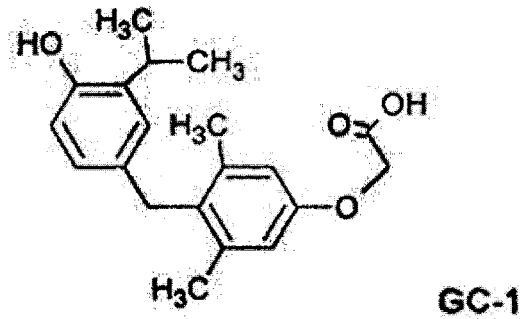
Column 24, Line 65, after "either alone or" add --in--.
Column 26, Line 8, after "fast growing" delete "a".
Column 26, Lines 30 and 49, replace "K-ms" with --K-ras--.
Column 26, Line 53, delete "rang" and insert --range--.

SEQUENCE LISTING

<160> NUMBER OF SEQ ID NOS: 10

<210> SEQ ID NO 1
<211> LENGTH: 29
<212> TYPE: DNA
<213> ORGANISM: Artificial Sequence
<220> FEATURE:
<223> OTHER INFORMATION: Chemically Synthesized Primer Sequence

<400> SEQUENCE: 1
aagaagatgc ggctgactgt cgagccaca                                29

<210> SEQ ID NO 2
<211> LENGTH: 29
<212> TYPE: DNA
<213> ORGANISM: Artificial Sequence
<220> FEATURE:
<223> OTHER INFORMATION: Chemically Synthesized Primer Sequence

<400> SEQUENCE: 2
tctcatggtt cacacccatg acgaacatg                                29

<210> SEQ ID NO 3
<211> LENGTH: 30
<212> TYPE: DNA
<213> ORGANISM: Artificial Sequence
<220> FEATURE:
<223> OTHER INFORMATION: Chemically Synthesized Primer Sequence

<400> SEQUENCE: 3
gaataagatg gctgcagcca aatgccgcaa                               30

<210> SEQ ID NO 4
<211> LENGTH: 29
<212> TYPE: DNA
<213> ORGANISM: Artificial Sequence
<220> FEATURE:
<223> OTHER INFORMATION: Chemically Synthesized Primer Sequence

<400> SEQUENCE: 4
cagtcagatc aagggaagca cagacatct                                29

<210> SEQ ID NO 5
<211> LENGTH: 22
<212> TYPE: DNA
<213> ORGANISM: Artificial Sequence
<220> FEATURE:
<223> OTHER INFORMATION: Chemically Synthesized Primer Sequence

<400> SEQUENCE: 5
tggtcacagc tggctcccag aa                                       22

<210> SEQ ID NO 6
<211> LENGTH: 24
<212> TYPE: DNA
<213> ORGANISM: Artificial Sequence
<220> FEATURE:
<223> OTHER INFORMATION: Chemically Synthesized Primer Sequence

<400> SEQUENCE: 6
ccgtggagaa gtgaggcaga attt                                     24

<210> SEQ ID NO 7
<211> LENGTH: 30
<212> TYPE: DNA
<213> ORGANISM: Artificial Sequence

```
<220> FEATURE:
<223> OTHER INFORMATION: Chemically Synthesized Primer Sequence

<400> SEQUENCE: 7
ggaaacgacc ttctatgacg atgccctcaa                               30

<210> SEQ ID NO 8
<211> LENGTH: 30
<212> TYPE: DNA
<213> ORGANISM: Artificial Sequence
<220> FEATURE:
<223> OTHER INFORMATION: Chemically Synthesized Primer Sequence

<400> SEQUENCE: 8
gaacccctcc tgctcatctg tcacgttctt                               30

<210> SEQ ID NO 9
<211> LENGTH: 20
<212> TYPE: DNA
<213> ORGANISM: Artificial Sequence
<220> FEATURE:
<223> OTHER INFORMATION: Chemically Synthesized Primer Sequence

<400> SEQUENCE: 9
gtttgagccg agtgagcagg                                          20

<210> SEQ ID NO 10
<211> LENGTH: 20
<212> TYPE: DNA
<213> ORGANISM: Artificial Sequence
<220> FEATURE:
<223> OTHER INFORMATION: Chemically Synthesized Primer Sequence

<400> SEQUENCE: 10
atagcgctgt gctgcccaga                                          20
```